US012698477B2

(12) United States Patent

Flugelman

(10) Patent No.: US 12,698,477 B2
(45) Date of Patent: Aug. 4, 2026

(54) METHODS OF PRECONDITIONING VASCULAR CELLS FOR TRANSDUCTION, METHODS OF TRANSDUCTION AND METHODS OF PRESERVING TRANSDUCED CELLS

(71) Applicant: Vessl Therapeutics Ltd, Haifa (IL)

(72) Inventor: Moshe Y. Flugelman, Haifa (IL)

(73) Assignee: Vessi Therapeutics Ltd, Haifa (IL)

(*) Notice: Subject to any disclaimer, the term of this patent is extended or adjusted under 35 U.S.C. 154(b) by 822 days.

(21) Appl. No.: 17/523,041

(22) Filed: Nov. 10, 2021

(65) Prior Publication Data

US 2022/0145258 A1 May 12, 2022

Related U.S. Application Data

(60) Provisional application No. 63/111,693, filed on Nov. 10, 2020, provisional application No. 63/111,682, filed on Nov. 10, 2020, provisional application No. 63/111,696, filed on Nov. 10, 2020, provisional application No. 63/111,661, filed on Nov. 10, 2020.

(51) Int. Cl.
| | |
|---|---|
| *C12N 5/077* | (2010.01) |
| *C12N 5/071* | (2010.01) |
| *C12N 15/86* | (2006.01) |
| *C12N 5/00* | (2006.01) |

(52) U.S. Cl.
CPC ........... *C12N 5/0661* (2013.01); *C12N 5/069* (2013.01); *C12N 15/86* (2013.01); *C12N 5/0031* (2013.01); *C12N 2500/32* (2013.01); *C12N 2500/34* (2013.01); *C12N 2501/165* (2013.01); *C12N 2510/00* (2013.01)

(58) Field of Classification Search
CPC ...... A61K 35/44; C12N 5/0661; C12N 15/86; C12N 2740/10043; C12N 2740/15043
See application file for complete search history.

(56) References Cited

U.S. PATENT DOCUMENTS

| | | | |
|---|---|---|---|
| 5,405,742 A | 4/1995 | Taylor | |
| 5,514,536 A | 5/1996 | Taylor | |
| 6,492,103 B1 | 12/2002 | Taylor | |
| 6,790,657 B1 | 9/2004 | Arya | |
| 7,524,493 B2 | 4/2009 | Flugelman et al. | |
| 2003/0073237 A1 | 4/2003 | Roks et al. | |
| 2004/0053207 A1 | 3/2004 | Griffiths et al. | |
| 2004/0116343 A1* | 6/2004 | Flugelman | A61K 38/1866 514/8.1 |
| 2004/0147026 A1 | 7/2004 | Arya | |
| 2004/0151707 A1* | 8/2004 | Gluzman | A61K 49/0056 424/93.21 |
| 2004/0170962 A1 | 9/2004 | Kafri et al. | |
| 2006/0275338 A1* | 12/2006 | Flugelman | C07K 14/52 514/8.1 |
| 2009/0209630 A1 | 8/2009 | Coleman et al. | |
| 2010/0105133 A1 | 4/2010 | Kanias et al. | |
| 2011/0177488 A1 | 7/2011 | Natan et al. | |
| 2012/0015343 A1 | 1/2012 | Taylor et al. | |
| 2015/0203869 A1* | 7/2015 | Baker | A61P 9/08 435/456 |
| 2015/0274779 A1* | 10/2015 | Gaston | C07K 16/00 424/139.1 |
| 2016/0046685 A1 | 2/2016 | Nolta et al. | |

FOREIGN PATENT DOCUMENTS

| | | |
|---|---|---|
| EP | 2163642 | 3/2010 |
| WO | WO 02/12539 | 2/2002 |

OTHER PUBLICATIONS

Meng et al., Ectopic expression of human angiopoietin-1 promotes functional recovery and neurogenesis after focal cerebral ischemia. Neuroscience (2014), 267: 135-146 (Year: 2014).*
An et al., Engineering of Corpus Cavernosum Using Vascular Endothelial Growth Factor-expressing Muscle-derived Stem Cells Seeded on Acellular Corporal Collagen Matrices. Urology (2013), 81: 424-431 (Year: 2013).*
Pagano and Vaheri, Enhancement of infectivity of poliovirus RNA with diethylaminoethyl-dextran (DEAE-D). Arch. Gesamte Virusforsch. (1965), 17: 456-464 (Year: 1965).*
McCutchan and Pagano, Enhancement of the Infectivity of Simian Virus 40 Deoxyribonucleic Acid With Dlethylaminoethyl-DextranJ . . . Natl. Cancer Inst. (1968), 41: 351-357 (Year: 1968).*
Meghan Rego, Getting the Most from Your Lentiviral Transduction, Addgene Blog, posted Apr. 7, 2016, https://blog.addgene.org/getting-the-most-from-your-lentiviral-transduction [retrieved Oct. 17, 2024] (Year: 2016).*
Kumar et al., DEAE-Dextran Transfection. Cold Spring Harb Protoc (2018); doi: 10.1101/pdb.top096263 (Year: 2018).*
Holter et al., Efficient gene transfer by sequential treatment of mammalian cells with DEAE-dextran and deoxyribonucleic acid. Experimental Cell Research (1989), 184: 546-551 (Year: 1989).*
Al-Moslih and Dubes, The Kinetics of DEAE-Dextran-induced Cell Sensitization to Transfection. J. Gen. Virol. (1973), 18: 189-193 ( Year: 1973).*
Kahn et al., Optimization of retroviral vector-mediated gene transfer into endothelial cells in vitro. Circulation Research (1992), 71: 1508-1517 (Year: 1992).*
Benoit Giquel, Quick Guide to All Things Lentivirus, Addgene Blog, posted Mar. 21, 2017, https://blog.addgene.org/quick-guide-to-all-things-lentivirus [retrieved Oct. 17, 2024] (Year: 2017).*
SmGM®-2 Supplements and Growth Factors, https://bioscience.lonza.com/lonza_bs/CH/en/Primary-and-Stem-Cells/p/000000000000185378/ SmGM -- 2-Smooth-Muscle-Cell-Growth-Medium-2-SingleQuots-Supplements-and-Growth-Factors, [retrieved May 1, 2025] (Year: 2025).*
PLXSN Retroviral Vector Information, PT3134-5 (Year: 2000).*
GenBank X62568.1, https://www.ncbi.nlm.nih.gov/nuccore/X62568.1, available Jul. 30, 1996, [retrieved May 2, 2025] (Year: 1996).*

(Continued)

*Primary Examiner* — Catherine Konopka

(57) ABSTRACT

Methods and compositions for pre-conditioning, transduction and/or hypothermic preservation of vascular cells transduced with nucleic acid constructs for expressing pro-angiogenic factors are provided. Also provided are uses of such cells in therapy.

13 Claims, 17 Drawing Sheets

Figure 1:
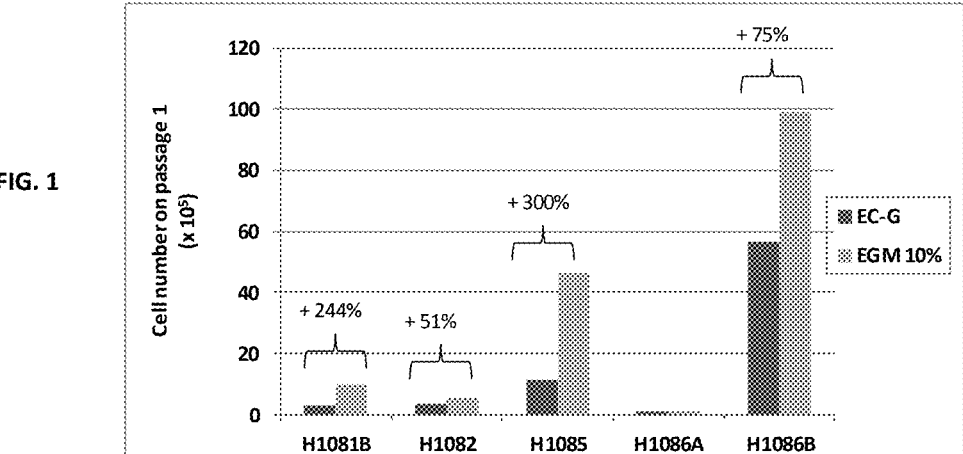

Specification includes a Sequence Listing.

(56) References Cited

OTHER PUBLICATIONS

Xuechong Hong, Thesis: Derivation of Functional Endothelial Cells from Human Vascular Smooth Muscle Cells through Reprogramming, Aug. 2017 (Year: 2017).*
Daria Love, The effect of DEAE-dextran on the infectivity of a feline calicivirus and its RNA. Archiv für die gesamte Virusforschung (1973), 41: 52-58 (Year: 1973).*
Schwartz et al., A microtransfection method using the luciferase-encoding reporter gene for the assay of human immunodeficiency virus LTR promoter activity. Gene (1990), 88: 197-205; p. 199, ¶2-3 (Year: 1990).*
Laithier and Sheldrick, "Influence of DEAE-dextran treatment and cellular" age"on infection by herpes simplex virus DNA". IARC Scientific Publications (1975), 11 Pt 1: 85-90 (Year: 1975).*
European Search Report and the European Search Opinion Dated Mar. 18, 2022 From the European Patent Office Re. Application No. 21207428.0. (12 Pages).
Adams et al. "Roles of EphrinB Ligands and EphB Receptors in Cardiovascular Development: Demarcation of Arterial/Venous Domains, Vascular Morphogenesis, and Sprouting Angiogenesis", Genes & Development, 13(3): 295-306, Feb. 1, 1999.
Anderson "Prospects for Human Gene Therapy", Science, 226(4673): 401-409, Oct. 26, 1984.
Asahara et al. "Synergistic Effect of Vascular Endothelial Growth Factor and Basic Fibroblast Growth Factor on Angiogenesis In Vivo", Circulation, 92(9): 365-371, Nov. 1, 1995.
Baust et al. "Cryopreservation: Evolution of Molecular Based Strategies", Advances in Experimental Medicine and Biology, 951: 13-29, Jan. 2016.
Braunwald "Shattuck Lecture—Cardiovascular Medicine at the Turn of the Millenium: Triumphs, Concerns, and Opportunities", The New England Journal of Medicine, 337(19): 1360-1369, Nov. 6, 1997.
Cao et al. "Leptin Induces Vascular Permeability and Synergistically Stimulates Angiogenesis With FGF-1 and VEGF", Proc. Natl. Acad. Sci. USA, PNAS, 98(11): 6390-6395, May 22, 2001.
Carmeliet et al. "Role of Tissue Factor in Embryonic Blood Vessel Development", Nature, 383(6595): 73-75, Sep. 5, 1996.
Carmeliet et al. "Targeted Deficiency or Cytosolic Truncation of the VE-Cadherin Gene in Mice Impairs VEGF-Mediated Endothelial Survival and Angiogenesis", Cell, 98(2): 147-157, Jul. 23, 1999.
Chae et al. "Coadministration of Angiopoietin-1 and Vascular Endothelial Growth Factor Enhances Collateral Vascularization", Arteriosclerosis, Thrombosis, and Vascular Biology, 20(12): 2573-2578, Dec. 2000.
Chen et al. "Upstream Stimulatory Factors Regulate Aortic Preferentially Expressed Gene-1 Expression in Vascular Smooth Muscle Cells", The Journal of Biological Chemistry, 276(50): 47658-47663, Published Online Oct. 17, 2001.
Collins et al. "Molecular Cloning of the Human Gene for Von Willebrand Factor and Identification of the Transcription Initiation Site", Proc. Natl. Acad. Sci. USA, 84(13): 4393-4397, Jul. 1987.
Collins et al. "Structure and Chromosomal Location of the Gene for Endothelial-Leukocyte Adhesion Molecule 1", The Journal of Biological Chemistry, 266(4): 2466-2473, Feb. 5, 1991.
Dull et al. "Kinetics of Placenta Growth Factor/Vascular Endothelial Growth Factor Synergy in Endothelial Hydraulic Conductivity and Proliferation", Microvascular Research, 61(2): 203-210, Mar. 2001.
Dumont et al. "Dominant-Negative and Targeted Null Mutations in the Endothelial Receptor Tyrosine Kinase, Tek, Reveal a Critical Role in Vasculogenesis of the Embryo", Genes & Development, 8(16): 1897-1909, Aug. 15, 1994.
Ferrara et al. "Heterozygous Embryonic Lethality Induced by Targeted Inactivation of the VEGF Gene", Nature, 380(6573): 439-442, Apr. 4, 1996.
Flugelman et al. "Genetically Engineered Endothelial Cells Remain Adherent and Viable After Stent Deployment and Exposure to Flow In Vitro", Circulation Research, 70(2): 348-354, Feb. 1992.

Folkman et al "Long-Term Culture of Capillary Endothelial Cells", Proc. Natl. Acad. Sci. USA, 76(10): 5217-5221, Oct. 1979.
Folkman et al. "Blood Vessel Formation: What Is Its Molecular Basis?", Cell, 87(7): 1153-1155, Dec. 27, 1996.
Fong et al. "Role of the Flt-1 Receptor Tyrosine Kinase in Regulating the Assembly of Vascular Endothelium", Nature, 376(6535): 66-70, Jul. 6, 1995.
Hanahan "Signaling Vascular Morphogenesis and Maintenance", Science, 277(5322): 48-50, Jul. 4, 1997.
Harats et al. "Targeting Gene Expression to the Vascular Wall in Transgenic Mice Using the Murine Preproendothelin-1 Promoter", The Journal of Clinical Investigation, 95(3): 1335-1344, Mar. 1995.
Hendel et al. "Effect of Intracoronary Recombinant Human Vascular Endothelial Growth Factor on Myocardial Perfusion", Circulation, 101(2): 118-121, Jan. 18, 2000.
Horley et al. "Molecular Cloning of Murine Intercellular Adhesion Molecule (ICAM-1)", The EMBO Journal, 8(10): 2889-2896, Oct. 1989.
Hsieh et al. "Genomic Cloning and Promoter Analysis of Aortic Preferentially Expressed Gene-1. Identification of a Vascular Smooth Muscle-Specific Promoter Mediated by an E Box Motif ", The Journal of Biological Chemistry, 274(20): 14344-14351, May 14, 1999.
Iademarco et al. "Characterization of the Promoter for Vascular Cell Adhesion Molecule-1 (VCAM-1)", The Journal of Biological Chemistry, 267(23): 16323-16329, Aug. 15, 1992.
Isner et al. "Clinical Evidence of Angiogenesis After Arterial Gene Transfer of PhVEGF 165 in Patient With Ischaemic Limb", The Lancet, 348(9024): 270-374, Aug. 10, 1996.
Ito et al. "Monocyte Chemotactic Protein-1 Increases Collateral and Peripheral Conductance After Femoral Artery Occlusion", Circulation Research, 80(6): 829-837, Jun. 1, 1996.
Jain et al. "Leaky Vessels? Call Ang1!", Nature Medicine, 6(2): 131-132, Feb. 2000.
Kern et al. "Isolation and Culture of Microvascular Endothelium From Human Adipose Tissue", The Journal of Clinical Investigation, 71(6): 1822-1829, Jun. 1983.
Korpelainen et al. "Signaling Angiogenesis and Lymphoangiogenesis", Current Opinion in Cell Biology, 10(2): 159-164, Apr. 1998.
Kullo et al. "Vascular Gene Transfer: From Bench to Bedside", Arteriosclerosis, Thrombosis, and Vascular Biology, 19(2): 196-207, Feb. 1999.
Latchana et al. "Preservation Solutions for Cardiac and Pulmonary Donor Grafts: A Review of the Current Literature", Journal of Thoracic Disease, 6(8): 1143-1149, Aug. 2014.
Layne et al. "Characterization of the Mouse Aortic Carboxypeptidase-Like Protein Promoter Reveals Activity in Differentiated and Dedifferentiatid Vascular Smooth Muscle Cells", Circulation Research, 90(6): 728-736, Apr. 5, 2002.
Leveen et al. "Mice Deficient for PDGF B Show Renal, Cardiovascular, and Hematological Abnormalities", Genes & Development, 8(16): 1875-1887, Aug. 15, 1994.
Lewis et al. "Angiogenesis by Gene Therapy: A New Horizon for Myocardial Revascularization?", Cardiovascular Research, 35(3): 490-497, Sep. 1997.
Lindahl et al. "Pericyte Loss and Microaneurysm Formation in PDGF-B-Deficient Mice", Science, 277(5323): 242-245, Jul. 11, 1997.
Lindahl et al. "Role of Platelet-Derived Growth Factors in Angiogenesis and Alveogenesis", Current Topics in Pathology, 93: 27-33, 1999.
Maisonpierre et al. "Angiopoietin-2, A Natural Antagonist for Tie2 That Disrupts In Vivo Angiogenesis", Science, 277(5322): 55-60, Jul. 4, 1997.
Morishita et al. "A Novel Promoter for Vascular Endothelial Growth Factor Receptor (Flt-1) That Confers Endothelial-Specific Gene Expression", The Journal of Biological Chemistry, 270(46): 27948-27953, Nov. 17, 1995.
Mulligan "The Basic Science of Gene Therapy", Science, 260(5110): 926-932, May 14, 1993.
Newman et al. "PECAM-1 (CD31) Cloning and Relation to Adhesion Molecules of the Immunoglobulin Gene Superfamily", Science, New Series, 247(4947): 1219-1222, Mar. 9, 1990.

(56)        References Cited

OTHER PUBLICATIONS

Nikitenko et al. "Transcriptional Regulation of the CRLR Gene in Human Microvascular Endothelial Cells by Hypoxia", The FASEB Journal, 17(11): 1499-1501, Published Online Jun. 17, 2003.

Ouma et al. "Targets and Delivery Methods for Therapeutic Angiogenesis in Peripheral Artery Disease", Vascular Medicine, 17(3): 174-192, Published Online Apr. 11, 2012.

Pepper "Transforming Growth Factor-Beta: Vasculogenesis, Angiogenesis, and Vessel Wall Integrity", Cytokine & Growth Factor Reviews, 8(1): 21-43, Mar. 1997.

Pepper et al. "Vascular Endothelial Growth Factor (VEGF)-C Synergizes With Basic Fibroblast Growth Factor and VEGF in the Induction of Angiogenesis In Vitro and Alters Endothelial Cell Extracellular Proteolytic Activity", Journal of Cellular Physiology, 177(3): 439-452, Dec. 1998.

Rajantie et al. "Bmx Tyrosine Kinase Has a Redundant Function Downstream of Angiopoietin and Vascular Endothelial Growth Factor Receptors in Arterial Endothelium", Molecular and Cellular Biology, 21(14): 4647-4655, Jul. 2001.

Risau "Mechanisms of Angiogenesis", Nature, 386(6626): 671-674, Apr. 17, 1997.

Rius et al. "Cloning of the Promoter Region of Human Endoglin, the Target Gene for Hereditary Hemorrhagic Telangiectasia Type 1", Blood, 92(12): 4677-4690, Dec. 15, 1998.

Roenicke et al. "Characterization of the Endothelium-Specific Murine Vascular Endothelial Growth Factor Receptor-2 (Flk-1) Promoter", Circulation Research, 79(2): 277-285, Aug. 1, 1996.

Salani et al. "Endothelin-1 Induces An Angiogenic Phenotype in Cultured Endothelial Cells and Stimulates Neovascularization In Vivo", American Journal of Pathology, 157(5): 1703-1711, Nov. 2000.

Sato et al. "Distinct Roles of the Receptor Tyrosine Kinases Tie-1 and Tie-2 in Blood Vessel Formation", Nature, 376(6535): 70-74, Jul. 6, 1995.

Sato et al. "Tie-1 and Tie-2 Define Another Class of Putative Receptor Tyrosine Kinase Genes Expressed in Early Embryonic Vascular System", Proc. Natl. Acad. Sci. USA, 90(20): 9355-9358, Oct. 15, 1993.

Schaper et al. "Molecular Mechanisms of Coronary Collateral Vessel Growth", Circulation Research, 79(5): 911-919, Nov. 1, 1996.

Shalaby et al. "Failure of Blood-Island Formation and Vasculogenesis in Flk-1-Deficient Mice", Nature, 376(6535): 62-66, Jul. 6, 1995.

Sterpetti et al. "Comparison of Two Techniques to Isolate Microvascular Endothelial Cells From the Omentum", Journal of Surgical Research, 48(2): 101-106, Feb. 1990.

Sukhatme et al. "A Novel Early Growth Response Gene Rapidly Induced by Fibroblast, Epithelial Cell and Lymphocyte Mitogens", Oncogene Research, 1(4): 343-355, Sep./Oct. 1987.

Suri et al. "Requisite Role of Angiopoietin-1, A Ligand for the TIE2 Receptor, During Embryonic Angiogenesis", Cell, 87(7): 1171-1180, Dec. 27, 1996.

Thurston et al. "Angiopoietin-1 Protects the Adult Vasculature Against Plasma Leakage", Nature Medicine, 6(4): 460-463, Apr. 2000.

Varda-Bloom et al. "Tissue-Specific Gene Therapy Directed to Tumor Angiogenesis", Gene Therapy, XP002349279, 8(11): 819-827, Jun. 2001.

Vikkula et al. "Vascular Sysmorphogenesis Caused by an Activating Mutation in the Receptor Tyrosine Kinase TIE2", Cell, 87(7): 1181-1190, Dec. 27, 1996.

Vo et al. "Venographic Changes Associated With Seeded and Nonseeded Vena Cava Grafting", Vascular Surgery, 22(6): 393-397, Nov./ Dec. 1988.

Ware et al. "Angiogenesis in Ischemic Heart Disease: Inducing the Formation of New Blood Vessels—A Novel Approach to Treating Myocardial Ischemia", Nature Medicine, 3(2): 158-164, Feb. 1997.

Weisz et al. "Increased Vascular Endothelial Growth Factor 165 Bindinbg to Kinase Insert Domain-Containing Receptor After Infection of Human Endothelial Cells by Recombinant Adenovirus Encoding the Vegf 165 Gene", Circulation, XP055899528, 103(14): 1887-1892, Apr. 10, 2001.

Office Action Dated Jun. 4, 2025 From the Israel Patent Office Re. Application No. 287999. (4 Pages).

* cited by examiner

FIG. 7
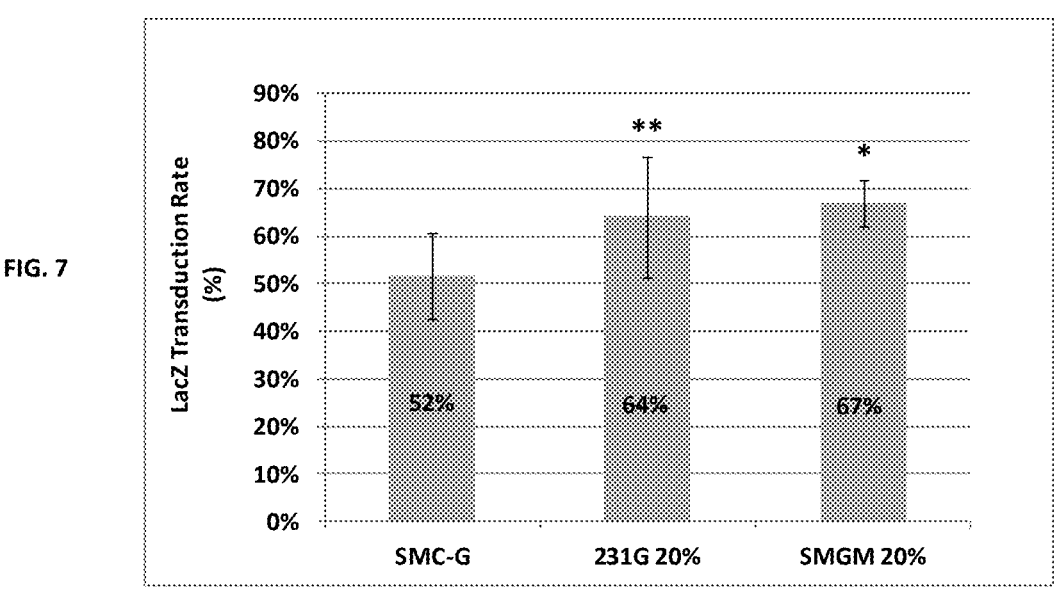
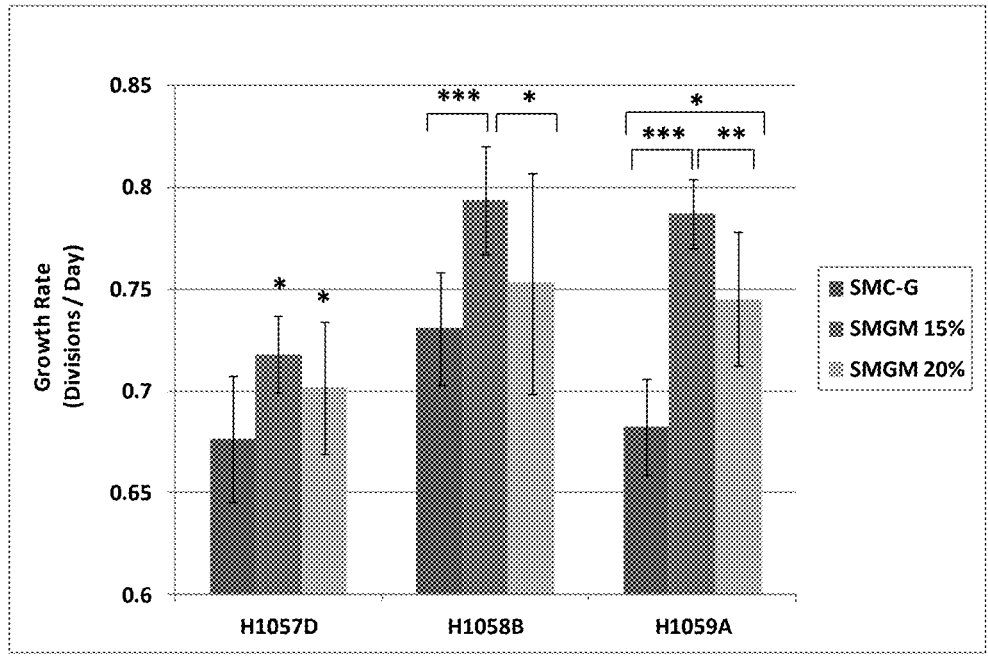
FIG. 8A

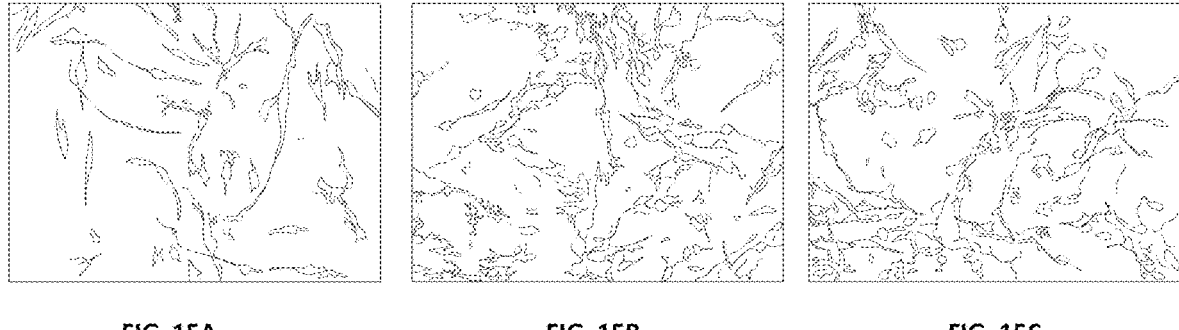
FIG. 15A                    FIG. 15B                    FIG. 15C
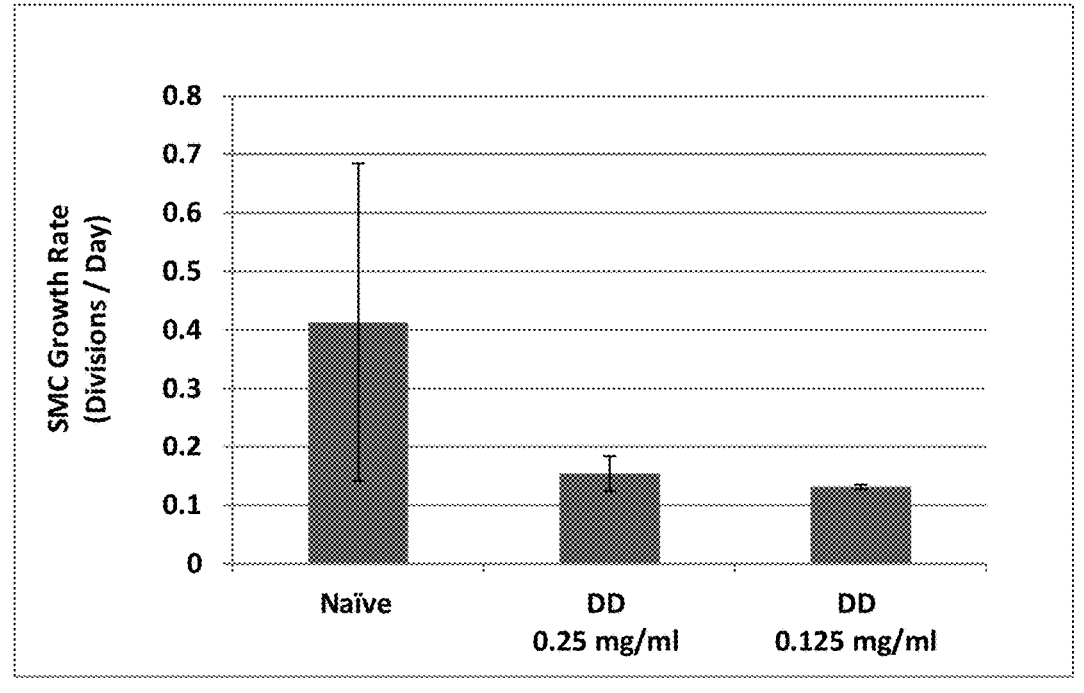
FIG. 16

FIG. 23A   FIG. 23B
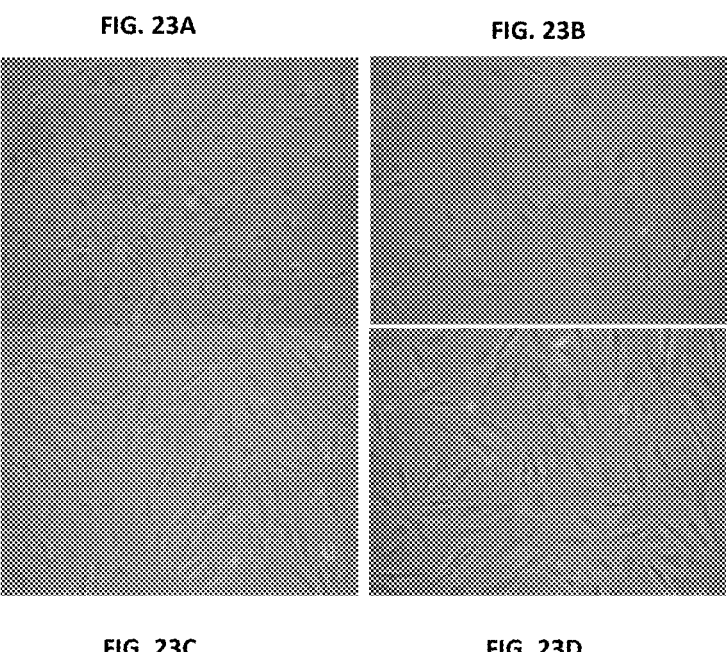
FIG. 23C   FIG. 23D
FIG. 24A   FIG. 24B
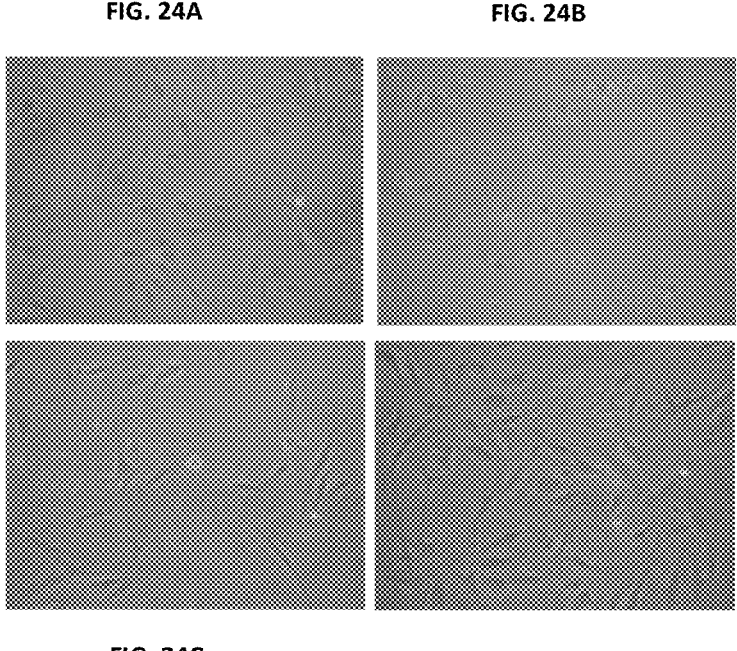
FIG. 24C   FIG. 24D

SEQUENCE LISTING

<160> NUMBER OF SEQ ID NOS: 2

<210> SEQ ID NO 1
<211> LENGTH: 6453
<212> TYPE: DNA
<213> ORGANISM: Artificial Sequence
<220> FEATURE:
<223> OTHER INFORMATION: VEGF 165 nucleic acid construct

<400> SEQUENCE: 1
tttgaaagac cccacccgta ggtggcaagc tagcttaagt aacgccactt tgcaaggcat          60
ggaaaaatac ataactgaga atagaaaagt tcagatcaag gtcaggaaca aagaaacagc         120

-continued

```
tgaataccaa acaggatatc tgtggtaagc ggttcctgcc ccggctcagg gccaagaaca    180
gatgagacag ctgagtgatg ggccaaacag gatatctgtg gtaagcagtt cctgccccgg    240
ctcggggcca agaacagatg gtccccagat gcggtccagc cctcagcagt ttctagtgaa    300
tcatcagatg tttccagggt gccccaagga cctgaaaatg accctgtacc ttatttgaac    360
taaccaatca gttcgcttct cgcttctgtt cgcgcgcttc cgctctccga gctcaataaa    420
agagcccaca acccctcact cggcgcgcca gtcttccgat agactgcgtc gcccgggtac    480
ccgtattccc aataaagcct cttgctgttt gcatccgaat cgtggtctcg ctgttccttg    540
ggagggtctc ctctgagtga ttgactaccc acgacggggg tctttcattt gggggctcgt    600
ccgggatttg agaccccctg cccagggacc accgaccac caccgggagg taagctggcc    660
agcaacttat ctgtgtctgt ccgattgtct agtgtctatg tttgatgtta tgcgcctgcg    720
tctgtactag ttagctaact agctctgtat ctggcggacc cgtggtggaa ctgacgagtt    780
ctgaacaccc ggccgcaacc ctgggagacg tcccagggac tttgggggcc gttttttgtgg   840 cccgacctga ggaagggagt cgatgtggaa tccgaccccg tcaggatatg tggttctggt    900
aggagacgag aacctaaaac agttcccgcc tccgtctgaa tttttgcttt cggtttggaa    960
ccgaagccgc gcgtcttgtc tgctgcagcg ctgcagcatc gttctgtgtt gtctctgtct   1020
gactgtgttt ctgtatttgt ctgaaaatta gggccagact gttaccactc ccttaagttt   1080
gaccttaggt cactggaaag atgtcgagcg gatcgctcac aaccagtcgg tagatgtcaa   1140
gaagagacgt tgggttacct tctgctctgc agaatggcca acctttaacg tcggatggcc   1200
gcgagacggc acctttaacc gagacctcat cacccaggtt aagatcaagg tcttttcacc   1260
tggcccgcat ggacacccag accaggtccc ctacatcgtg acctgggaag ccttggcttt   1320 tgaccccct ccctgggtca agccctttgt acaccctaag cctccgcctc ctcttcctcc   1380 atccgcccccg tctctccccc ttgaacctcc tcgttcgacc ccgcctcgat cctcccttta   1440
tccagccctc actccttctc taggcgccgg aattcgttaa ctcgaggatc cgaaaccatg   1500
aactttctgc tgtcttgggt gcattggagc cttgccttgc tgctctacct ccaccatgcc   1560
aagtggtccc aggctgcacc catggcagaa ggaggagggc agaatcatca cgaagtggtg   1620
aagttcatgg atgtctatca gcgcagctac tgccatccaa tcgagaccct ggtggacatc   1680
ttccaggagt accctgatga gatcgagtac atcttcaagc catcctgtgt gcccctgatg   1740
cgatgcgggg gctgctgcaa tgacgagggc ctggagtgtg tgcccactga ggagtccaac   1800
atcaccatgc agattatgcg gatcaaacct caccaaggcc agcacatagg agagatgagc   1860
ttcctacagc acaacaaatg tgaatgcaga ccaaagaaag atagagcaag acaagaaaat   1920
ccctgtgggc cttgctcaga gcggagaaag catttgtttg tacaagatcc gcagacgtgt   1980
aaatgttcct gcaaaaacac agactcgcgt tgcaaggcga ggcagcttga gttaaacgaa   2040
cgtacttgca gatgtgacaa gccgaggcgg tgatgaatga atgaggatcc ggctgtggaa   2100
tgtgtgtcag ttagggtgtg aaagtcccca ggctcccca gcaggcagaa gtatgcaaag   2160
catgcatctc aattagtcag caaccaggtg tggaaagtcc ccaggctccc cagcaggcag   2220
aagtatgcaa agcatgcatc tcaattagtc agcaaccata gtcccgcccc taactccgcc   2280
catcccgccc ctaactccgc ccagttccgc ccattctccg ccccatggct gactaatttt   2340
ttttatttat gcagaggccg aggccgcctc ggcctctgag ctattccaga agtagtgagg   2400
aggctttttt ggaggcctag gcttttgcaa aaagcttggg ctgcaggtcg aggcggatct   2460
```

```
gatcaagaga caggatgagg atcgtttcgc atgattgaac aagatggatt gcacgcaggt    2520
tctccggccg cttgggtgga gaggctattc ggctatgact gggcacaaca gacaatcggc    2580
tgctctgatg ccgccgtgtt ccggctgtca gcgcaggggc gcccggttct ttttgtcaag    2640
accgacctgt ccggtgccct gaatgaactg caggacgagg cagcgcggct atcgtggctg    2700
gccacgacgg gcgttccttg cgcagctgtg ctcgacgttg tcactgaagc gggaagggac    2760
tggctgctat tgggcgaagt gccgggggcag gatctcctgt catctcacct tgctcctgcc    2820
gagaaagtat ccatcatggc tgatgcaatg cggcggctgc atacgcttga tccggctacc    2880
tgcccattcg accaccaagc gaaacatcgc atcgagcgag cacgtactcg gatggaagcc    2940
ggtcttgtcg atcaggatga tctggacgaa gagcatcagg ggctcgcgcc agccgaactg    3000
ttcgccaggc tcaaggcgcg catgcccgac ggcgaggatc tcgtcgtgac ccatggcgat    3060
gcctgcttgc cgaatatcat ggtggaaaat ggccgctttt ctggattcat cgactgtggc    3120
cggctgggtg tggcggaccg ctatcaggac atagcgttgg ctacccgtga tattgctgaa    3180
gagcttggcg gcgaatgggc tgaccgcttc ctcgtgcttt acggtatcgc cgctcccgat    3240
tcgcagcgca tcgccttcta tcgccttctt gacgagttct tctgagcggg actctggggt    3300
tcgataaaat aaaagatttt atttagtctc cagaaaaagg gggaatgaa agaccccacc      3360 tgtaggtttg gcaagctagc ttaagtaacg ccattttgca aggcatggaa aaatacataa    3420
ctgagaatag agaagttcag atcaaggtca ggaacagatg gaacagctga atatgggcca    3480
aacaggatat ctgtggtaag cagttcctgc cccggctcag ggccaagaac agatggaaca    3540
gctgaatatg ggccaaacag gatatctgtg gtaagcagtt cctgccccgg ctcagggcca    3600
agaacagatg gtccccagat gcggtccagc cctcagcagt ttctagagaa ccatcagatg    3660
tttccagggt gccccaagga cctgaaatga ccctgtgcct tatttgaact aaccaatcag    3720
ttcgcttctc gcttctgttc gcgcgcttct gctccccgag ctcaataaaa gagcccacaa    3780
cccctcactc ggggcgccag tcctccgatt gactgagtcg cccgggtacc cgtgtatcca    3840
ataaaccctc ttgcagttgc atccgacttg tggtctcgct gttccttggg agggtctcct    3900
ctgagtgatt gactacccgt cagcgggggt ctttcatttg gggctcgtc cgggatcggg     3960 agacccctgc ccagggacca ccgacccacc accgggaggt aagctggctg cctcgcgcgt    4020
ttcggtgatg acggtgaaaa cctctgacac atgcagctcc cggagacggt cacagcttgt    4080
ctgtaagcgg atgccgggag cagacaagcc cgtcagggcg cgtcagcggg tgttggcggg    4140
tgtcggggcg cagccatgac ccagtcacgt agcgatagcg gagtgtatac tggcttaact    4200
atgcggcatc agagcagatt gtactgagag tgcaccatat gcggtgtgaa ataccgcaca    4260
gatgcgtaag gagaaaatac cgcatcaggc gctcttccgc ttcctcgctc actgactcgc    4320
tgcgctcggt cgttcggctg cggcgagcgg tatcagctca ctcaaaggcg gtaatacggt    4380
tatccacaga atcaggggat aacgcaggaa agaacatgtg agcaaaaggc cagcaaaagg    4440
ccaggaaccg taaaaaggcc gcgttgctgg cgtttttcca taggctccgc ccccctgacg    4500
agcatcacaa aaatcgacgc tcaagtcaga ggtggcgaaa cccgacagga ctataaagat    4560
accaggcgtt tccccctgga agctccctcg tgcgctctcc tgttccgacc ctgccgctta    4620
ccggatacct gtccgccttt ctcccttcgg gaagcgtggc gctttctcat agctcacgct    4680
gtaggtatct cagttcggtg taggtcgttc gctccaagct gggctgtgtg cacgaacccc    4740
ccgttcagcc cgaccgctgc gccttatccg gtaactatcg tcttgagtcc aacccggtaa    4800
gacacgactt atcgccactg gcagcagcca ctggtaacag gattagcaga gcgaggtatg    4860
```

-continued

```
taggcggtgc tacagagttc ttgaagtggt ggcctaacta cggctacact agaaggacag      4920
tatttggtat ctgcgctctg ctgaagccag ttaccttcgg aaaaagagtt ggtagctctt      4980
gatccggcaa acaaaccacc gctggtagcg gtggtttttt tgtttgcaag cagcagatta      5040
cgcgcagaaa aaaaggatct caagaagatc ctttgatctt ttctacgggg tctgacgctc      5100
agtggaacga aaactcacgt taagggattt tggtcatgag attatcaaaa aggatcttca      5160
cctagatcct tttaaattaa aaatgaagtt ttaaatcaat ctaaagtata tatgagtaaa      5220
cttggtctga cagttaccaa tgcttaatca gtgaggcacc tatctcagcg atctgtctat      5280
ttcgttcatc catagttgcc tgactccccg tcgtgtagat aactacgata cgggagggct      5340
taccatctgg ccccagtgct gcaatgatac cgcgagaccc acgctcaccg gctccagatt      5400
tatcagcaat aaaccagcca gccggaaggg ccgagcgcag aagtggtcct gcaactttat      5460
ccgcctccat ccagtctatt aattgttgcc gggaagctag agtaagtagt tcgccagtta      5520
atagtttgcg caacgttgtt gccattgctg caggcatcgt ggtgtcacgc tcgtcgtttg      5580
gtatggcttc attcagctcc ggttcccaac gatcaaggcg agttacatga tcccccatgt      5640
tgtgcaaaaa agcggttagc tccttcggtc ctccgatcgt tgtcagaagt aagttggccg      5700
cagtgttatc actcatggtt atggcagcac tgcataattc tcttactgtc atgccatccg      5760
taagatgctt ttctgtgact ggtgagtact caaccaagtc attctgagaa tagtgtatgc      5820
ggcgaccgag ttgctcttgc ccggcgtcaa cacgggataa taccgcgcca catagcagaa      5880
ctttaaaagt gctcatcatt ggaaaacgtt cttcggggcg aaaactctca aggatcttac      5940
cgctgttgag atccagttcg atgtaaccca ctcgtgcacc caactgatct tcagcatctt      6000
ttactttcac cagcgtttct gggtgagcaa aaacaggaag gcaaaatgcc gcaaaaaagg      6060
gaataagggc gacacggaaa tgttgaatac tcatactctt cctttttcaa tattattgaa      6120
gcatttatca gggttattgt ctcatgagcg gatacatatt tgaatgtatt tagaaaaata      6180
aacaaatagg ggttccgcgc acatttcccc gaaaagtgcc acctgacgtc taagaaacca      6240
ttattatcat gacattaacc tataaaaata ggcgtatcac gaggcccttt cgtcttcaag      6300
aattgctagc aattcatacc agatcaccga aaactgtcct ccaaatgtgt ccccctcaca      6360
ctcccaaatt cgcgggcttc tgcctcttag accactctac cctattcccc acactcaccg      6420
gagccaaagc cgcggccctt ccgtttcttt gct                                   6453
```

```
<210> SEQ ID NO 2
<211> LENGTH: 7389
<212> TYPE: DNA
<213> ORGANISM: Artificial Sequence
<220> FEATURE:
<223> OTHER INFORMATION: Angiopoietin nucleic acid construct

<400> SEQUENCE: 2
tttgaaagac cccacccgta ggtggcaagc tagcttaagt aacgccactt tgcaaggcat        60
ggaaaaatac ataactgaga atagaaaagt tcagatcaag gtcaggaaca agaaacagc        120 tgaataccaa acaggatatc tgtggtaagc ggttcctgcc ccggctcagg gccaagaaca       180
gatgagacag ctgagtgatg gccaaacag atatctgtg gtaagcagtt cctgccccgg        240
ctcggggcca agaacagatg gtccccagat gcggtccagc cctcagcagt ttctagtgaa       300
tcatcagatg tttccagggt gccccaagga cctgaaaatg accctgtacc ttatttgaac       360
taaccaatca gttcgcttct cgcttctgtt cgcgcgcttc cgctctccga gctcaataaa       420
```

```
agagcccaca accectcact cggcgcgcca gtcttccgat agactgcgtc gcccgggtac      480
ccgtattccc aataaagcct cttgctgttt gcatccgaat cgtggtctcg ctgttccttg      540
ggagggtctc ctctgagtga ttgactaccc acgacggggg tctttcattt gggggctcgt      600
ccgggatttg gagaccccctg cccagggacc accgacccac caccgggagg taagctggcc      660
agcaacttat ctgtgtctgt ccgattgtct agtgtctatg tttgatgtta tgcgcctgcg      720
tctgtactag ttagctaact agctctgtat ctggcggacc cgtggtggaa ctgacgagtt      780
ctgaacaccc ggccgcaacc ctgggagacg tcccagggac tttggggggcc gttttttgtgg      840 cccgacctga ggaagggagt cgatgtggaa tccgaccccg tcaggatatg tggttctggt      900
aggagacgag aacctaaaac agttcccgcc tccgtctgaa tttttgcttt cggtttggaa      960
ccgaagccgc gcgtcttgtc tgctgcagcg ctgcagcatc gttctgtgtt gtctctgtct     1020
gactgtgttt ctgtatttgt ctgaaaatta gggccagact gttaccactc ccttaagttt     1080
gaccttaggt cactggaaag atgtcgagcg gatcgctcac aaccagtcgg tagatgtcaa     1140
gaagagacgt tgggttacct tctgctctgc agaatggcca acctttaacg tcggatggcc     1200
gcgagacggc acctttaacc gagacctcat cacccaggtt aagatcaagg tcttttcacc     1260
tggcccgcat ggacacccag accaggtccc ctacatcgtg acctgggaag ccttggcttt     1320
tgacccccct ccctgggtca agcccttttgt cacccctaag cctccgcctc ctcttcctcc     1380
atccgccccg tctctccccc ttgaacctcc tcgttcgacc ccgcctcgat cctcccttta     1440
tccagccctc actccttctc taggcgccgg aattcgttaa ctcgaggatc tgctggcagt     1500
acaatgacag tttttccttttc ctttgctttc ctcgctgcca ttctgactca cataggggtgc     1560 agcaatcagc gccgaagtcc agaaaacagt gggagaagat ataaccggat tcaacatggg     1620
caatgtgcct acactttcat tcttccagaa cacgatggca actgtcgtga gagtacgaca     1680
gaccagtaca acacaaacgc tctgcagaga gatgctccac acgtggaacc ggatttctct     1740
tcccagaaac ttcaacatct ggaacatgtg atggaaaatt atactcagtg gctgcaaaaa     1800
cttgagaatt acattgtgga aaacatgaag tcggagatgg cccagataca gcagaatgca     1860
gttcagaacc acacggctac catgctggag ataggaacca gcctcctctc tcagactgca     1920
gagcagacca gaaagctgac agatgttgag acccaggtac taaatcaaac ttctcgactt     1980
gagatacagc tgctggagaa ttcattatcc acctacaagc tagagaagca acttcttcaa     2040
cagacaaatg aaatcttgaa gatccatgaa aaaaacagtt tattagaaca taaaatctta     2100
gaaatggaag aaaacacaa ggaagagttg gacaccttaa aggaagagaa agagaacctt     2160
caaggcttgg ttactcgtca aacgtatata atccaggagc tggaaaagca attaaacaga     2220
gctaccacca caacagtgt ccttcagaag cagcaactgg agctgatgga cacagtccac     2280
aaccttgtca atctttgcac taaagaaggt gtttttactaa agggaggaaa aagagaggaa     2340
gagaaaccat ttagagactg tgcagatgta tatcaagctg gttttaataa aagtggaatc     2400
tacactattt atattaataa tatgccagaa cccaaaaagg tgttttgcaa tatggatgtc     2460
aatgggggag gttggactgt aatacaacat cgtgaagatg gaagtctaga tttccaaaga     2520
ggctggaagg aatataaaat gggttttgga aatcccctccg gtgaatattg gctggggaat     2580
gagtttattt ttgccattac cagtcagagg cagtacatgc taagaattga gttaatggac     2640
tgggaaggga accgagccta ttcacagtat gacagattcc acatagggaaa tgaaaagcaa     2700 aactataggt tgtatttaaa aggtcacact gggacagcag gaaaacagag cagcctgatc     2760
ttacacggtg ctgatttcag cactaaagat gctgataatg acaactgtat gtgcaaatgt     2820
```

-continued

```
gccctcatgt taacaggagg atggtggttt gatgcttgtg gcccctccaa tctaaatgga      2880
atgttctata ctgcgggaca aaaccatgga aaactgaatg ggataaagtg gcactacttc      2940
aaagggccca gttactcctt acgttccaca actatgatga ttcgaccttt agatttttga      3000
agatccggct gtggaatgtg tgtcagttag ggtgtggaaa gtccccaggc tccccagcag      3060
gcagaagtat gcaaagcatg catctcaatt agtcagcaac caggtgtgga aagtccccag      3120
gctccccagc aggcagaagt atgcaaagca tgcatctcaa ttagtcagca accatagtcc      3180
cgcccctaac tccgcccatc ccgcccctaa ctccgcccag ttccgcccat tctccgcccc      3240
atggctgact aattttttttt atttatgcag aggccgaggc cgcctcggcc tctgagctat      3300
tccagaagta gtgaggaggc ttttttggag gcctaggctt ttgcaaaaag cttgggctgc      3360
aggtcgaggc ggatctgatc aagagacagg atgaggatcg tttcgcatga ttgaacaaga      3420
tggattgcac gcaggttctc cggccgcttg ggtggagagg ctattcggct atgactgggc      3480
acaacagaca atcggctgct ctgatgccgc cgtgttccgg ctgtcagcgc aggggcgccc      3540
ggttcttttt gtcaagaccg acctgtccgg tgccctgaat gaactgcagg acgaggcagc      3600
gcggctatcg tggctggcca cgacgggcgt tccttgcgca gctgtgctcg acgttgtcac      3660
tgaagcggga agggactggc tgctattggg cgaagtgccg gggcaggatc tcctgtcatc      3720
tcaccttgct cctgccgaga aagtatccat catggctgat gcaatgcggc ggctgcatac      3780
gcttgatccg gctacctgcc cattcgacca ccaagcgaaa catcgcatcg agcgagcacg      3840
tactcggatg gaagccggtc ttgtcgatca ggatgatctg gacgaagagc atcagggggct      3900 cgcgccagcc gaactgttcg ccaggctcaa ggcgcgcatg cccgacggcg aggatctcgt      3960
cgtgacccat ggcgatgcct gcttgccgaa tatcatggtg gaaaatggcc gcttttctgg      4020
attcatcgac tgtggccggc tgggtgtggc ggaccgctat caggacatag cgttggctac      4080
ccgtgatatt gctgaagagc ttggcggcga atgggctgac cgcttcctcg tgctttacgg      4140
tatcgccgct cccgattcgc agcgcatcgc cttctatcgc cttcttgacg agttcttctg      4200
agcgggactc tggggttcga taaaataaaa gattttattt agtctccaga aaaaggggg      4260 aatgaaagac cccacctgta ggtttggcaa gctagcttaa gtaacgccat tttgcaaggc      4320
atggaaaaat acataactga gaatagagaa gttcagatca aggtcaggaa cagatggaac      4380
agctgaatat gggccaaaca ggatatctgt ggtaagcagt tcctgccccg gctcagggcc      4440
aagaacagat ggaacagctg aatatgggcc aaacaggata tctgtggtaa gcagttcctg      4500
ccccggctca gggccaagaa cagatggtcc ccagatgcgg tccagccctc agcagtttct      4560
agagaaccat cagatgtttc cagggtgccc caaggacctg aaatgaccct gtgccttatt      4620
tgaactaacc aatcagttcg cttctcgctt ctgttcgcgc gcttctgctc ccgagctca      4680 ataaaagagc ccacaacccc tcactcgggg cgccagtcct ccgattgact gagtcgcccg      4740
ggtacccgtg tatccaataa accctcttgc agttgcatcc gacttgtggt ctcgctgttc      4800
cttgggaggg tctcctctga gtgattgact acccgtcagc gggggtcttt catttggggg      4860
ctcgtccggg atcgggagac ccctgcccag ggaccaccga cccaccaccg ggaggtaagc      4920
tggctgcctc gcgcgtttcg gtgatgacgg tgaaaacctc tgacacatgc agctcccgga      4980
gacggtcaca gcttgtctgt aagcggatgc cgggagcaga caagcccgtc agggcgcgtc      5040
agcgggtgtt ggcgggtgtc ggggcgcagc catgacccag tcacgtagcg atagcggagt      5100
gtatactggc ttaactatgc ggcatcagag cagattgtac tgagagtgca ccatatgcgg      5160
```

```
tgtgaaatac cgcacagatg cgtaaggaga aaataccgca tcaggcgctc ttccgcttcc   5220
tcgctcactg actcgctgcg ctcggtcgtt cggctgcggc gagcggtatc agctcactca   5280
aaggcggtaa tacggttatc cacagaatca ggggataacg caggaaagaa catgtgagca   5340
aaaggccagc aaaaggccag gaaccgtaaa aaggccgcgt tgctggcgtt tttccatagg   5400
ctccgccccc ctgacgagca tcacaaaaat cgacgctcaa gtcagaggtg gcgaaacccg   5460
acaggactat aaagatacca ggcgtttccc cctggaagct ccctcgtgcg ctctcctgtt   5520
ccgaccctgc cgcttaccgg atacctgtcc gcctttctcc cttcgggaag cgtggcgctt   5580
tctcatagct cacgctgtag gtatctcagt tcggtgtagg tcgttcgctc caagctgggc   5640
tgtgtgcacg aaccccccgt tcagcccgac cgctgcgcct tatccggtaa ctatcgtctt   5700
gagtccaacc cggtaagaca cgacttatcg ccactggcag cagccactgg taacaggatt   5760
agcagagcga ggtatgtagg cggtgctaca gagttcttga agtggtggcc taactacggc   5820
tacactagaa ggacagtatt tggtatctgc gctctgctga agccagttac cttcggaaaa   5880
agagttggta gctcttgatc cggcaaacaa accaccgctg gtagcggtgg tttttttgtt   5940
tgcaagcagc agattacgcg cagaaaaaaa ggatctcaag aagatccttt gatcttttct   6000
acggggtctg acgctcagtg gaacgaaaac tcacgttaag ggattttggt catgagatta   6060
tcaaaaagga tcttcaccta gatcctttta aattaaaaat gaagttttaa atcaatctaa   6120
agtatatatg agtaaacttg gtctgacagt taccaatgct taatcagtga ggcacctatc   6180
tcagcgatct gtctatttcg ttcatccata gttgcctgac tccccgtcgt gtagataact   6240
acgatacggg agggcttacc atctggcccc agtgctgcaa tgataccgcg agacccacgc   6300
tcaccggctc cagatttatc agcaataaac cagccagccg gaagggccga gcgcagaagt   6360
ggtcctgcaa ctttatccgc ctccatccag tctattaatt gttgccggga gctagagta    6420 agtagttcgc cagttaatag tttgcgcaac gttgttgcca ttgctgcagg catcgtggtg   6480
tcacgctcgt cgtttggtat ggcttcattc agctccggtt cccaacgatc aaggcgagtt   6540
acatgatccc ccatgttgtg caaaaaagcg gttagctcct tcggtcctcc gatcgttgtc   6600
agaagtaagt tggccgcagt gttatcactc atggttatgg cagcactgca taattctctt   6660
actgtcatgc catccgtaag atgcttttct gtgactggtg agtactcaac caagtcattc   6720
tgagaatagt gtatgcggcg accgagttgc tcttgcccgg cgtcaacacg ggataatacc   6780
gcgccacata gcagaacttt aaaagtgctc atcattggaa aacgttcttc ggggcgaaaa   6840
ctctcaagga tcttaccgct gttgagatcc agttcgatgt aacccactcg tgcacccaac   6900
tgatcttcag catcttttac tttcaccagc gtttctgggt gagcaaaaac aggaaggcaa   6960
aatgccgcaa aaaagggaat aagggcgaca cggaaatgtt gaatactcat actcttcctt   7020
tttcaatatt attgaagcat ttatcagggt tattgtctca tgagcggata catatttgaa   7080
tgtatttaga aaaataaaca aataggggtt ccgcgcacat ttccccgaaa agtgccacct   7140
gacgtctaag aaaccattat tatcatgaca ttaacctata aaaataggcg tatcacgagg   7200
ccctttcgtc ttcaagaatt gctagcaatt gctagcaatt gctagcaatt cataccagat   7260
caccgaaaac tgtcctccaa atgtgtcccc ctcacactcc caaattcgcg ggcttctgcc   7320
tcttagacca ctctacccta ttccccacac tcaccggagc caaagccgcg gcccttccgt   7380
ttctttgct                                                           7389
```

METHODS OF PRECONDITIONING VASCULAR CELLS FOR TRANSDUCTION, METHODS OF TRANSDUCTION AND METHODS OF PRESERVING TRANSDUCED CELLS

RELATED APPLICATIONS

This application claims the benefit of priority from U.S. Provisionals Patent Application Nos. 63/111,661, 63/111,682, 63/111,693 and 63/111,696, all filed on Nov. 10, 2020 and each of which is incorporated by reference in its entirety.

SEQUENCE LISTING STATEMENT

The ASCII file, entitled 89918SequenceListing.txt, created on Nov. 10, 2021, comprising 18,849 bytes, submitted concurrently with the filing of this application is incorporated herein by reference.

FIELD AND BACKGROUND OF THE INVENTION

The present invention relates to the fields of chemistry, biochemistry, cellular biology, genetic engineering and medicine. In particular, it relates to methods for preparation of transduced cells for storage prior to use. Specifically, it relates to methods of preconditioning vascular cells for transduction, methods of transduction, methods of preserving transduced cells and the use of the preserved transduced cells in the clinic.

Peripheral artery disease (PAD), and its advanced stage, critical limb ischemia affects some 200 million people worldwide. Symptoms associated with lower-extremity PAD include claudication and even more severe manifestations such as rest pain, ischemic ulcers and tissue loss. Percutaneous revascularization or surgical bypass is reserved for patients with severe, lifestyle-limiting claudication, however below the inguinal ligament percutaneous revascularization is limited by high rates of restenosis and surgical revascularization is limited by possible graft failure, and the risk associated with vascular surgery. Hence, alternative treatment strategies are needed for lifestyle-limiting claudication.

Angiogenesis or remodeling of collaterals is a complex process that requires the timely participation of progenitor cell, resident endothelial cells, smooth muscle cells and growth factors (including VEGF, FGF, placental growth factor and Ang-1) that can act in a coordinated manner, through many steps, to result in blood vessel formation. Theoretically, this can be achieved through administration of (recombinant) proteins, gene transfer or cell therapy approaches. However, clinical experience with systemic administration of growth factors (e.g. VEGF, bFGF) or related transcription factors (e.g. HIF-1 alpha) and local expression of single growth factors by gene transfer has failed to provide any significant therapeutic benefit (Ouma et al, Vase Med 2012, 17:174-92).

Angiogenic cell transfer therapy not only offers a self-replenishing source of growth factors, but also active participation in blood vessel development and expansion through the vascular cell engraftment.

Additional Related Background Art

Chae et al, Arterioscler Thromb Vasc Biol, 2000, 20:2573-78;
Ouma et al, Vasc Med 2012, 17:174-92;
Latchana et al, J Thorac Disease, 2014; 6:1143-49;
US Patent Application 20120015343;
Baust et al Adv Exp Med Biol 2016; 951:13-29;
U.S. Pat. No. 5,405,742;
U.S. Pat. No. 5,514,536;
U.S. Pat. No. 6,492,103;
US Patent Application No. 20040053207;
US Patent Application No. 20110177488;
US Patent Application No. 20100105133
US Patent Application No. 20160046685;
US Patent Application No. 2003/0073237;
US Patent Application No. 2009/0209630;
WO2002/12539.

SUMMARY OF THE INVENTION

According to an aspect of the invention there is provided human smooth muscle (SM) cells preconditioned for transduction with a retroviral nucleic acid construct or lentivirus nucleic acid construct comprising a polynucleotide sequence encoding a $VEGF_{165}$ polypeptide, wherein the preconditioning comprises contacting the SM cells with between 0.125 and 0.9 mg/ml DEAE-Dextran, the SM cells characterized by at least one of increased transduction rate and increased proliferation following transduction, as compared to similar SM cells preconditioned with 1.0 mg/ml DEAE-Dextran or greater.

According to some embodiments of the invention, the retroviral nucleic acid construct or lentivirus nucleic acid construct comprises the polynucleotide sequence as set forth in SEQ ID NO: 1.

According to some embodiments of the invention, the preconditioning is performed with 0.125 mg/ml-0.5 mg/ml DEAE-Dextran and for between 1 and 4 minutes.

According to some embodiments of the invention, the preconditioning is performed with 0.125 mg/ml DEAE-Dextran and for 1 minute.

According to some embodiments of the invention, the contacting is performed in a transduction medium comprising M199 medium.

According to some embodiments of the invention, the transduction medium further comprises 2 mM Glutamine.

According to some embodiments of the invention, the transduction medium is a serum-free medium.

According to some embodiments of the invention, the human smooth muscle cells are selected from the group consisting of freshly isolated smooth muscle cells from venous tissue, cryopreserved and thawed smooth muscle cells from venous tissue and cultured human smooth muscle cells.

According to some embodiments of the invention, the human smooth muscle cells are cultured in medium comprising Smooth muscle Growth Medium (SmGM)-2 Bullet Kit medium prior to and following the transduction.

According to some embodiments of the invention, the growth medium further comprises 5-25% fetal bovine serum (FBS).

According to some embodiments of the invention, the growth medium further comprises 10-20% fetal bovine serum (FBS).

According to some embodiments of the invention, the growth medium further comprises 15% fetal bovine serum (FBS).

According to some embodiments of the invention, the human smooth muscle cells are smooth muscle cells isolated from venous tissue in isolation medium comprising Smooth muscle Growth Medium (SmGM)-2 Bullet Kit medium and 20% fetal bovine serum.

According to an aspect of the invention there is provided human endothelial (EC) cells preconditioned for transduction with a retroviral nucleic acid construct or lentivirus nucleic acid construct comprising a polynucleotide sequence encoding an Angiopoietin-1 (Ang-1) polypeptide, wherein the preconditioning comprises:

(a) isolating the EC cells from venous tissue with an isolation medium comprising Endothelial Growth Medium (EGM)™-2 Bullet Kit medium and 10% Fetal Bovine Serum;

(b) culturing the isolated EC cells with an EC culture medium comprising Endothelial Growth Medium (EGM)™-2 Bullet Kit medium, and (c) preconditioning the human vascular endothelial cells with 1.0 mg/ml DEAE-Dextran, wherein the EC cells are characterized by at least one of increased transduction rate and increased proliferation following transduction, as compared to $(EGM)^T$-2 Bullet Kit medium.

According to some embodiments of the invention, the retroviral nucleic acid construct comprises the nucleic acid sequence as set forth in SEQ ID NO: 1.

According to some embodiments of the invention, the human endothelial cells are freshly isolated endothelial cells from venous tissue.

According to some embodiments of the invention, the human endothelial cells are isolated in step (a) in an isolation medium comprising Endothelial Growth Medium (EGM)™-2 Bullet Kit medium and 10% Fetal Bovine Serum.

According to some embodiments of the invention, the human endothelial cells are cultured in step (b) in growth medium comprising Endothelial Growth Medium (EGM)™-2 Bullet Kit medium and 5-25% Fetal Bovine Serum.

According to some embodiments of the invention, the growth medium of step (b) further comprises 10-20% fetal bovine serum (FBS).

According to some embodiments of the invention, the growth medium further comprises 10% fetal bovine serum (FBS).

According to some embodiments of the invention, the contacting is performed in a transduction medium comprising M199 medium.

According to some embodiments of the invention, the transduction medium further comprises 1-10 mM Glutamine.

According to some embodiments of the invention, the transduction medium further comprises 2 mM Glutamine.

According to some embodiments of the invention, the transduction medium is a serum-free medium.

According to an aspect of the invention there is provided a method for transducing human smooth muscle cells with a retroviral nucleic acid construct or lentivirus nucleic acid construct comprising a polynucleotide sequence encoding a $VEGF_{165}$ polypeptide, the method comprising:

(a) preconditioning the human smooth muscle cells with between 0.125 mg/ml and 0.9 mg/ml DEAE-Dextran, and (b) contacting the human smooth muscle cells with the retroviral nucleic acid construct or lentivirus nucleic acid construct in a transduction medium comprising the nucleic acid construct.

According to some embodiments of the invention, the retroviral nucleic acid construct or lentivirus nucleic acid construct comprises the nucleic acid sequence of SEQ ID NO: 1.

According to some embodiments of the invention, the preconditioning is performed with 0.125 mg/ml-0.5 mg/ml DEAE-Dextran.

According to some embodiments of the invention, the preconditioning is performed with 0.125 mg/ml DEAE-Dextran.

According to some embodiments of the invention, the preconditioning is performed for between 1 and 4 minutes.

According to some embodiments of the invention, the preconditioning is performed for between 2 and 3 minutes.

According to some embodiments of the invention, the preconditioning is performed for 1 minute.

According to some embodiments of the invention, the human smooth muscle cells are freshly isolated smooth muscle cells from venous tissue.

According to some embodiments of the invention, the human smooth muscle cells are isolated in an isolation medium comprising Smooth muscle Growth Medium (SmGM)-2 Bullet Kit medium and 20% Fetal Bovine Serum.

According to some embodiments of the invention, the human smooth muscle cells are cryopreserved and thawed smooth muscle cells from venous tissue.

According to some embodiments of the invention, the human smooth muscle cells are cultured prior to transduction.

According to some embodiments of the invention, the contacting of step (b) is performed in a volume of 1 ml transduction medium.

According to some embodiments of the invention, the human smooth muscle cells are cultured in medium comprising Smooth muscle Growth Medium (SmGM)-2 Bullet Kit medium prior to and following the transduction.

According to some embodiments of the invention, the growth medium further comprises 5-25% fetal bovine serum (FBS).

According to some embodiments of the invention, the growth medium further comprises 10-20% fetal bovine serum (FBS).

According to some embodiments of the invention, the growth medium further comprises 15% fetal bovine serum (FBS).

According to an aspect of the invention there is provided a method for transducing human endothelial cells with a retroviral nucleic acid construct or lentivirus nucleic acid construct comprising a polynucleotide sequence encoding an Angiopoietin-1 (Ang-1) polypeptide, the method comprising:

(a) preconditioning the human vascular endothelial cells with 1.0 mg/ml DEAE-Dextran, and (b) contacting the human endothelial cells in a transduction medium comprising the nucleic acid construct for a duration of at least 2.5 and no more than 3.5 contiguous hours.

According to some embodiments of the invention, the nucleic acid construct comprises the nucleic acid sequence of SEQ ID NO: 2.

According to some embodiments of the invention, the duration is 2.8-3.2 contiguous hours.

According to some embodiments of the invention, the duration is 2.5-3.0 contiguous hours.

According to some embodiments of the invention, the duration is 2.5 contiguous hours.

According to some embodiments of the invention, the human endothelial cells are freshly isolated endothelial cells from venous tissue.

According to some embodiments of the invention, the human endothelial cells are isolated in an isolation medium comprising Endothelial Growth Medium (EGM)™-2 Bullet Kit medium and 10% Fetal Bovine Serum.

According to some embodiments of the invention, the human endothelial cells are cryopreserved and thawed endothelial cells from venous tissue.

According to some embodiments of the invention, the human endothelial cells are cultured prior to transduction.

According to some embodiments of the invention, the human endothelial cells are cultured in growth medium comprising Endothelial Growth Medium (EGM)™-2 Bullet Kit medium prior to and following the transduction.

According to some embodiments of the invention, the growth medium further comprises 5-25% fetal bovine serum (FBS).

According to some embodiments of the invention, the growth medium further comprises 10-20% fetal bovine serum (FBS).

According to some embodiments of the invention, the growth medium further comprises 10% fetal bovine serum (FBS).

According to some embodiments of the invention, the transduction medium comprises M199 medium.

According to some embodiments of the invention, the transduction medium further comprises 1-10 mM Glutamine.

According to some embodiments of the invention, the transduction medium further comprises 2-8 mM Glutamine.

According to some embodiments of the invention, the transduction medium further comprises 2 mM Glutamine.

According to some embodiments of the invention, the transduction medium is a serum-free medium.

According to an aspect of the invention there is provided a method for hypothermal preservation of human smooth muscle cells transduced with a retroviral nucleic acid construct or lentivirus nucleic acid construct comprising a polynucleotide sequence encoding a $VEGF_{165}$ polypeptide, the method comprising incubating the transduced human smooth muscle cells in an intracellular-type hypothermic preservation solution at between 2° C. and 8° C.

According to some embodiments of the invention, the retroviral nucleic acid construct or lentivirus nucleic acid construct comprises the nucleic acid sequence of SEQ ID NO: 1.

According to some embodiments of the invention, the intracellular-type hypothermic preservation solution comprising lactobionate, sucrose, dextran, glucose, mannitol, HEPES buffer and energy substrates.

According to some embodiments of the invention, the hypothermic preservation solution further comprises Trolox, Na ions, K ions, calcium ions and Mg ions.

According to some embodiments of the invention, the energy substrates comprise adenosine and glutathione.

According to some embodiments of the invention, the hypothermic preservation solution comprises lactobionate, sucrose, dextran-40, glucose, mannitol, HEPES buffer, Trolox, Na ions, K ions, calcium ions, Mg ions, adenosine and glutathione.

According to some embodiments of the invention, the hypothermic preservation solution is HypoThermosol® FRS.

According to some embodiments of the invention, the human smooth muscle cells are freshly isolated smooth muscle cells from venous tissue.

According to some embodiments of the invention, the transduced human smooth muscle cells are cultured in medium comprising Smooth muscle Growth Medium (SmGM)-2 Bullet Kit medium prior to the hypothermic preservation.

According to some embodiments of the invention, the growth medium further comprises 15% fetal bovine serum (FBS).

According to some embodiments of the invention, the transduced smooth muscle cells are characterized by at least one of enhanced viability after hypothermic preservation, enhanced cell proliferation after hypothermic preservation or enhanced transgene expression following hypothermic preservation, as compared to identical transduced smooth muscle cells preserved in an isotonic multiple electrolytes solution.

According to an aspect of the invention there is provided a method for hypothermal preservation of human endothelial cells transduced with a retroviral nucleic acid construct or lentivirus nucleic acid construct comprising a polynucleotide sequence encoding a Angiopoietin-1 (Ang-1) polypeptide, the method comprising incubating the transduced human endothelial cells in an isotonic-type hypothermic preservation solution comprising an isotonic multiple electrolytes solution at between 2° C. and 8° C.

According to some embodiments of the invention, the retroviral nucleic acid construct or lentivirus nucleic acid construct comprises the nucleic acid sequence of SEQ ID NO: 2.

According to some embodiments of the invention, the isotonic multiple electrolytes solution is supplemented with dextrose, heparin and albumin.

According to some embodiments of the invention, the isotonic multiple electrolytes solution comprises Na ions, K ions, Mg ions, acetate ions and gluconate ions.

According to some embodiments of the invention, the pH of the isotonic-type hypothermic preservation solution is adjusted to 7.4-7.7 with sodium bicarbonate.

According to some embodiment, the isotonic hypothermic preservation solution comprises Na ions, K ions, Mg ions, acetate ions, gluconate ions, dextrose, heparin.

According to some embodiments of the invention, the hypothermic preservation solution comprises Plasma-Lyte A® supplemented with 0.1% dextrose, 100 U/ml heparin and 1% human albumin and is adjusted to pH 7.4-7.7 with sodium bicarbonate.

According to some embodiments of the invention, the human endothelial cells are freshly isolated endothelial cells from venous tissue.

According to some embodiments of the invention, the transduced human endothelial cells are cultured in medium comprising Endothelial Growth Medium (EGM)™-2 Bullet Kit medium and 10% Fetal Bovine Serum prior to the hypothermic preservation.

According to some embodiments of the invention, the transduced endothelial cells are characterized by at least one of enhanced viability after hypothermic preservation, enhanced cell proliferation after hypothermic preservation or enhanced transgene expression following hypothermic preservation, as compared to identical transduced endothelial cells preserved in an intracellular-type hypothermic preservation solution.

According to some embodiments of the invention, the incubation is performed for up to 96 hours.

According to some embodiments of the invention, the incubation is performed for 12-72 hours.

According to some embodiments of the invention, the incubation is performed for 24-48 hours.

According to some embodiments of the invention, the incubation is performed between 4° C. and 6° C.

According to some embodiments of the invention, the incubation is performed at 4° C.

According to an aspect of the invention there is provided an injectable composition comprising human smooth muscle (SM) cells transduced with a retroviral nucleic acid construct or lentivirus nucleic acid construct comprising a polynucleotide sequence encoding a $VEGF_{165}$ polypeptide suspended in an intracellular-type hypothermic preservation solution.

According to some embodiments of the invention, the polynucleotide sequence encoding a $VEGF_{165}$ polypeptide is as set forth in SEQ ID NO: 1.

According to some embodiments of the invention, the intracellular-type hypothermic preservation solution comprising lactobionate, sucrose, dextran, glucose, mannitol, HEPES buffer and energy substrates.

According to some embodiments of the invention, the hypothermic preservation solution further comprises Trolox, Na ions, K ions, calcium ions and Mg ions.

According to some embodiments of the invention, the energy substrates comprise adenosine and glutathione.

According to some embodiments of the invention, the hypothermic preservation solution comprises lactobionate, sucrose, dextran-40, glucose, mannitol, HEPES buffer, Trolox, Na ions, K ions, calcium ions, Mg ions, adenosine and glutathione.

According to some embodiments of the invention, the hypothermic preservation solution is HypoThermosol® FRS.

According to some embodiments of the invention, the human smooth muscle cells are freshly isolated smooth muscle cells from venous tissue.

According to some embodiments of the invention, the transduced human smooth muscle cells are cultured in medium comprising Smooth muscle Growth Medium (SmGM)-2 Bullet Kit medium prior to suspension in the hypothermic preservation solution.

According to some embodiments of the invention, the growth medium further comprises 15% fetal bovine serum (FBS).

According to an aspect of the invention there is provided an injectable composition comprising human endothelial cells transduced with a retroviral nucleic acid construct or lentivirus nucleic acid construct comprising a polynucleotide sequence encoding a Angiopoietin-1 (Ang-1) polypeptide, suspended in an isotonic-type hypothermic preservation solution comprising an isotonic multiple electrolytes solution.

According to some embodiments of the invention, the polynucleotide sequence encoding the Angiopoietin-1 (Ang-1) polypeptide is as set forth in SEQ ID NO: 2.

According to some embodiments of the invention, the isotonic-type hypothermic preservation solution is further supplemented with dextrose, heparin and albumin.

According to some embodiments of the invention, the isotonic multiple electrolytes solution comprises Na ions, K ions, Mg ions, acetate ions and gluconate ions.

According to some embodiments of the invention, the pH of the isotonic-type hypothermic preservation solution is adjusted to 7.4-7.7 with sodium bicarbonate.

According to some embodiments of the invention, the isotonic hypothermic preservation solution comprises Na ions, K ions, Mg ions, acetate ions, gluconate ions, dextrose, heparin and human albumin, and is adjusted to pH 7.4-7.7 with sodium bicarbonate.

According to some embodiments of the invention, the hypothermic preservation solution comprises Plasma-Lyte A® supplemented with 0.1% dextrose, 100 U/ml heparin and 1% human albumin and is adjusted to pH 7.4-7.7 with sodium bicarbonate.

According to some embodiments of the invention, the human endothelial cells are freshly isolated endothelial cells from venous tissue.

According to some embodiments of the invention, the transduced human endothelial cells are cultured in medium comprising Endothelial Growth Medium (EGM)™-2 Bullet Kit medium and 10% Fetal Bovine Serum prior to the hypothermic preservation.

According to an aspect of the invention there is provided a hypothermically preserved injectable transduced human vascular cell composition comprising the injectable composition described above at between 2° C. and 8° C.

According to some embodiments of the invention, the hypothermically preserved injectable transduced human vascular cell composition comprising transduced smooth muscle cells characterized by at least one of enhanced viability, enhanced cell proliferation after hypothermic preservation or enhanced transgene expression, as compared to identical transduced smooth muscle cells hypothermically preserved in an isotonic multiple electrolytes solution.

According to an aspect of the invention there is provided a hypothermically preserved injectable transduced human vascular cell composition comprising the injectable composition described above at between 2° C. and 8° C.

According to some embodiments of the invention, the hypothermically preserved injectable transduced human vascular cell composition comprising transduced endothelial cells characterized by at least one of enhanced viability after hypothermic preservation, enhanced cell proliferation after hypothermic preservation or enhanced transgene expression following hypothermic preservation, as compared to identical transduced endothelial cells preserved in an intracellular-type hypothermic preservation solution.

According to an aspect of the invention there is provided a kit comprising a first container comprising the injectable composition comprising human smooth muscle cells and a separate second container comprising the injectable composition comprising human endothelial cells.

According to some embodiments of the invention, the kit is at between 2° C. and 8° C.

According to some embodiments of the invention, the injectable composition is between 2° C. and 4° C.

According to some embodiments of the invention, the hypothermically preserved injectable human vascular cell composition following hypothermic preservation at the temperature for between 6 and 96 hours.

According to some embodiments of the invention, the hypothermically preserved injectable human vascular cell composition following hypothermic preservation at the temperature for between 12 and 48 hours.

According to some embodiments of the invention, the hypothermically preserved injectable human vascular cell composition following hypothermic preservation at the temperature for 24 or 48 hours.

According to some embodiments of the invention, the hypothermically preserved injectable human vascular cell composition or the kit for use in angiogenic cell therapy.

According to some embodiments of the invention, the hypothermically preserved injectable human vascular cell composition or the kit for use in treatment of a vascular condition or disease in a subject in need thereof.

According to some embodiments of the invention, the vascular condition or disease is selected from the group consisting of atherosclerosis, peripheral artery disease, a vascular complication of diabetes, ischemia and chronic renal failure.

According to some embodiments of the invention, the hypothermically preserved injectable human vascular cell composition or the kit for use in neovascularization in a subject in need thereof.

According to an aspect of the invention there is provided a method of angiogenic cell therapy comprising administering to a subject in need thereof the injectable composition or the hypothermically preserved injectable human vascular cell composition or the kit described above.

According to an aspect of the invention there is provided a method of treating a vascular condition or disease in a subject in need thereof, comprising administering to the subject the injectable composition or the hypothermically preserved injectable human vascular cell composition or the kit described above.

According to some embodiments of the invention, the vascular condition or disease is selected from the group consisting of atherosclerosis, peripheral artery disease, a vascular complication of diabetes, ischemia and chronic renal failure.

According to an aspect of the invention there is provided a method of affecting neovascularization in a subject in need thereof comprising administering the injectable composition, the hypothermally preserved injectable human vascular cell composition or the kit described above.

According to some embodiments of the invention, the neovascularization is affected by direct administration of the injectable composition to an affected blood vessel of the subject.

BRIEF DESCRIPTION OF THE SEVERAL
VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 2:
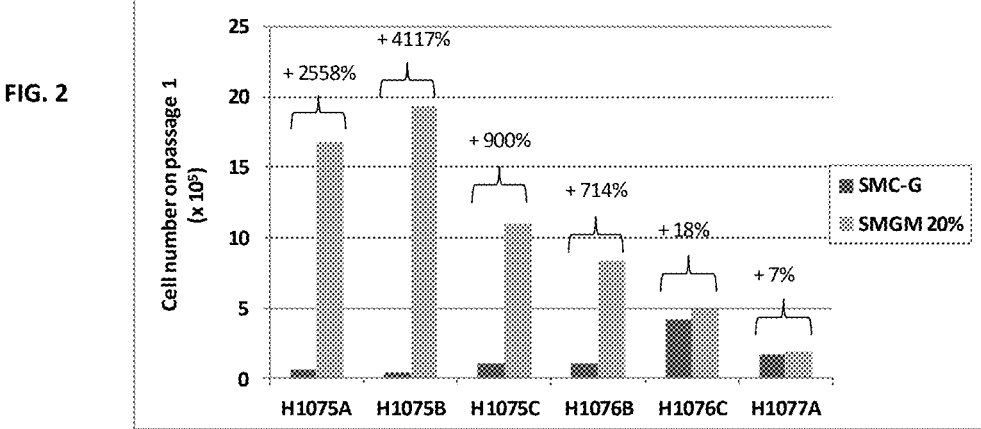
Figure 3:
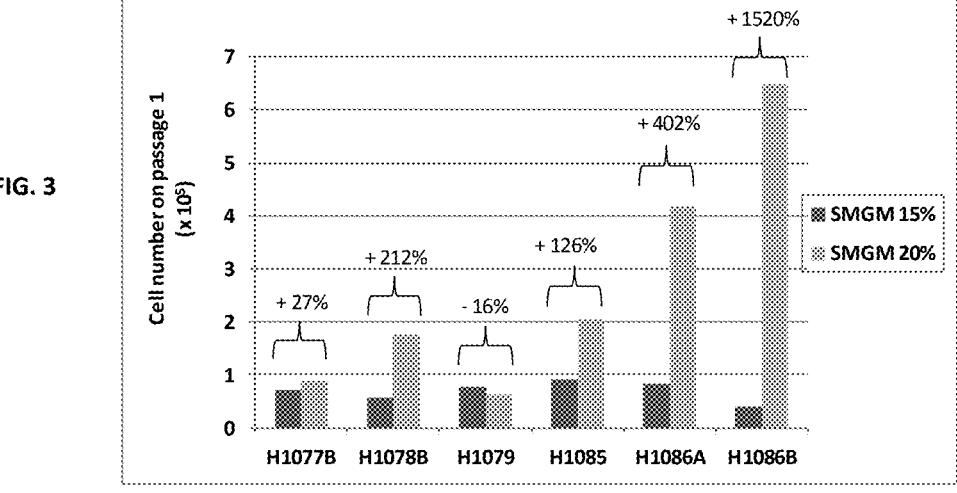
Figure 4:
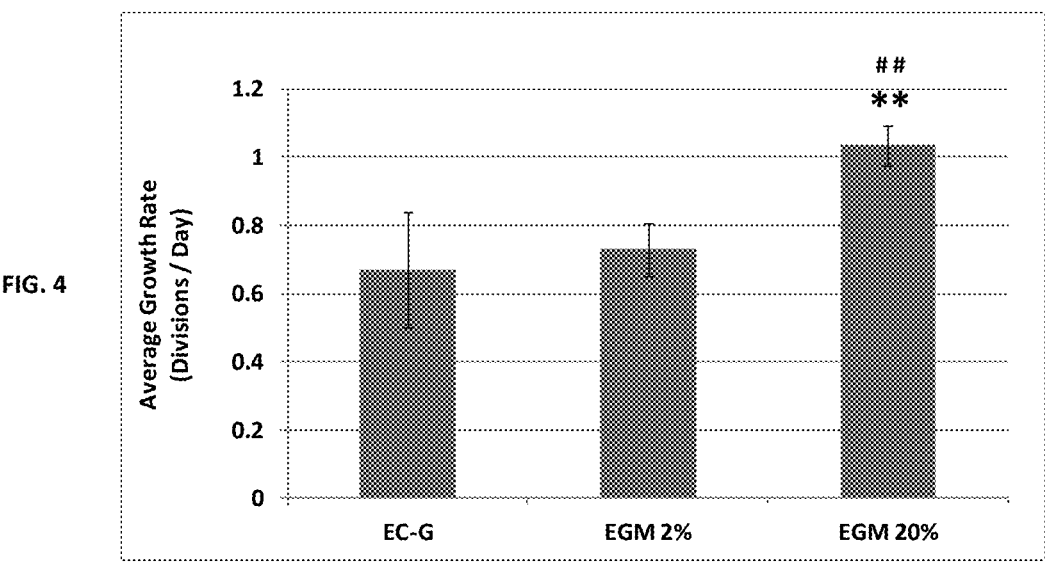
Figures 5, 6:
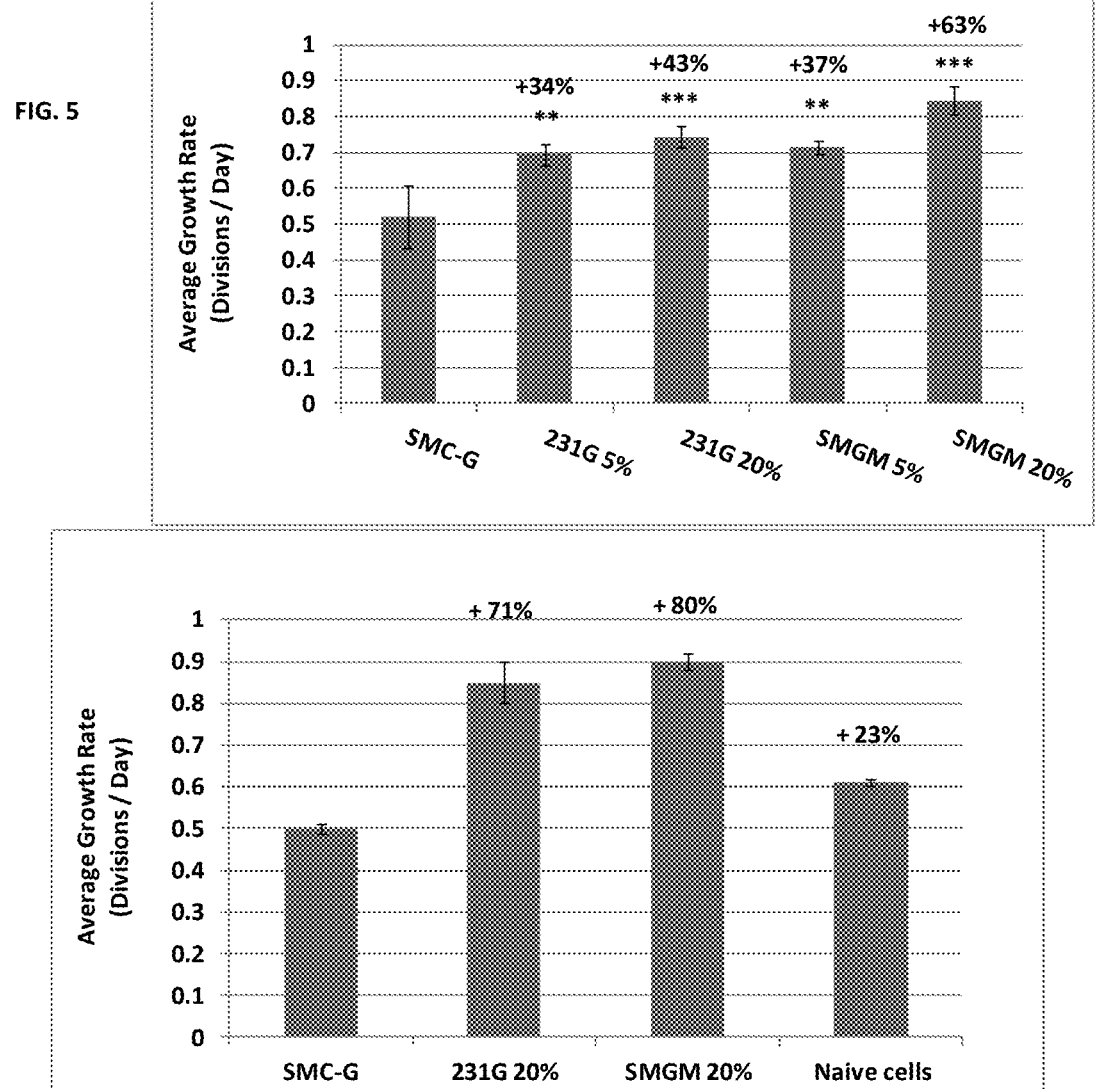
Figure 8B:
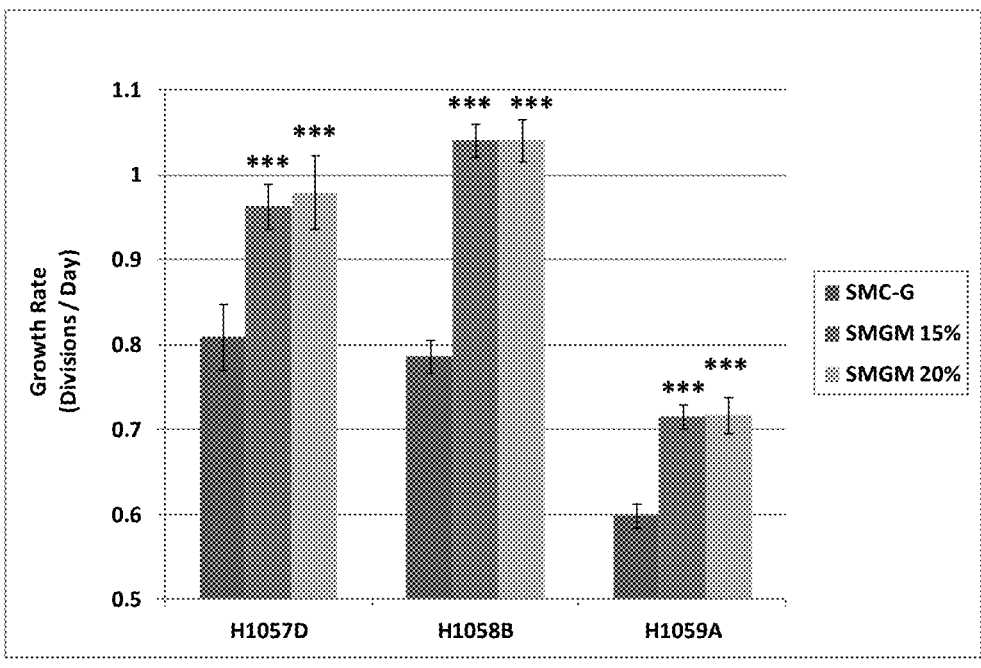
Figure 9:
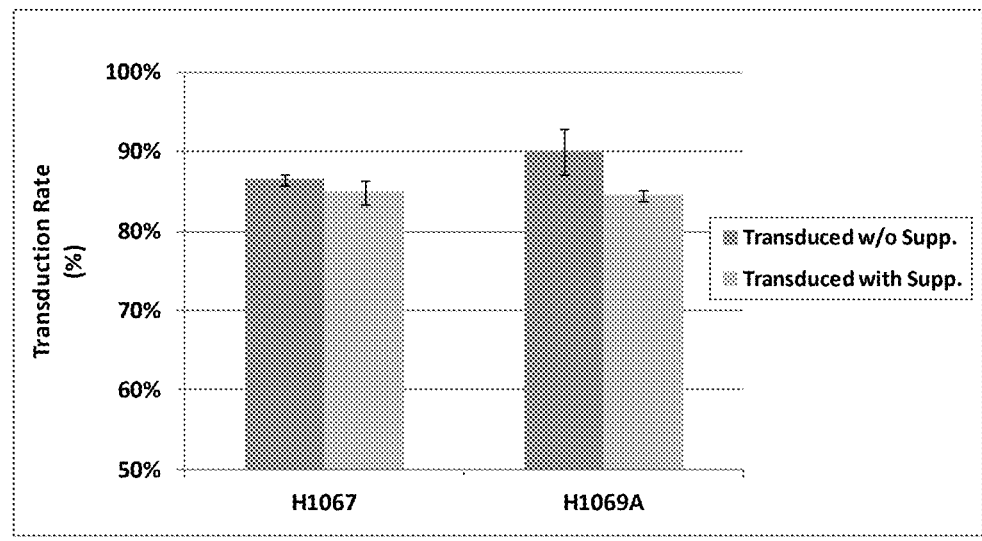
Figure 10:
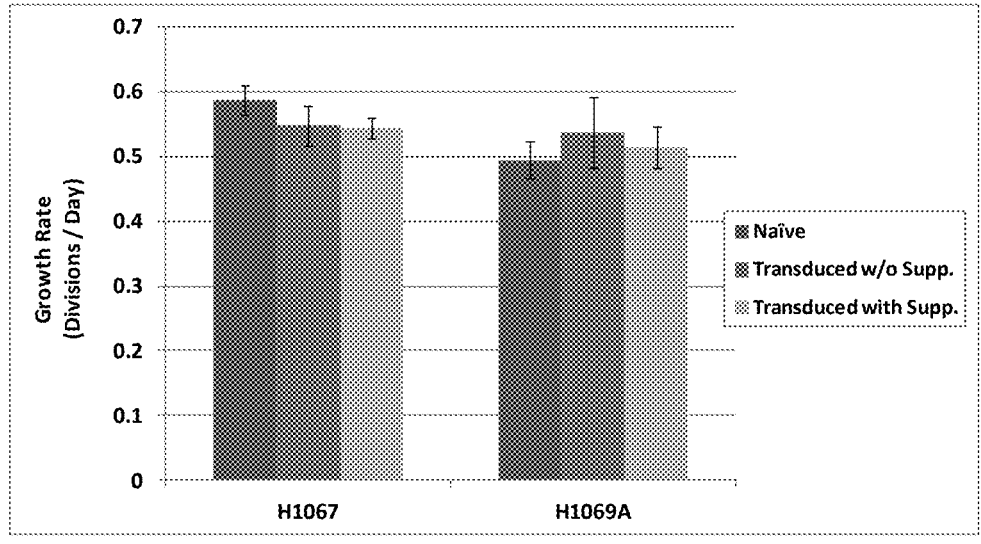
Figure 11:
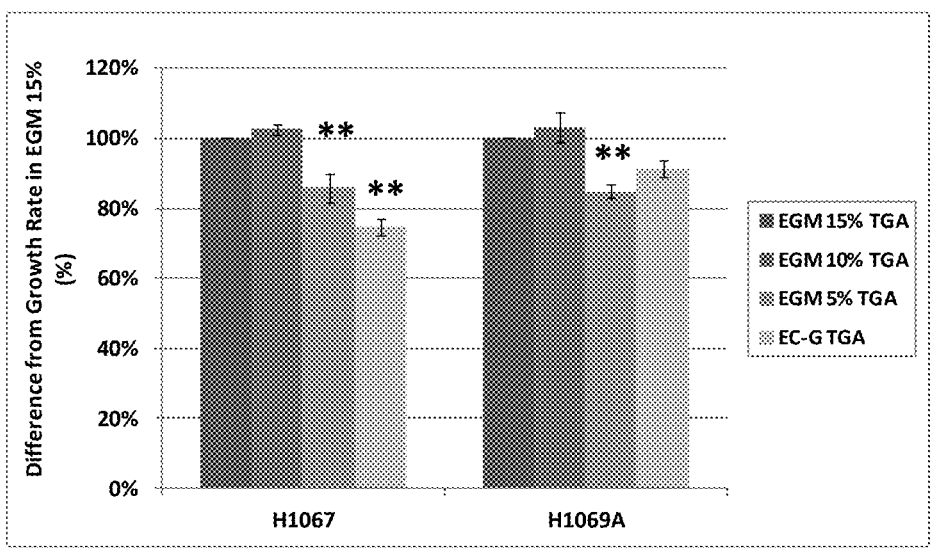
Figure 12:
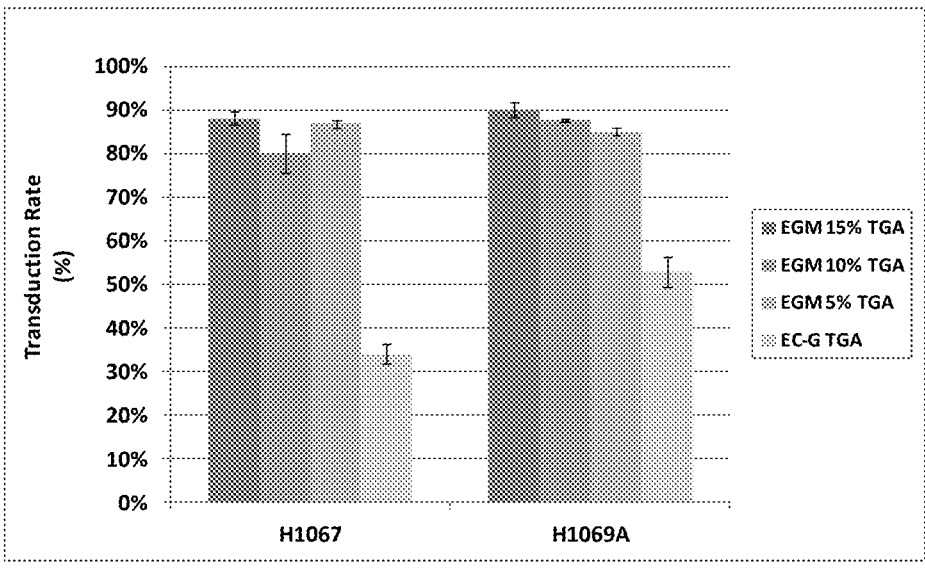
Figure 13:
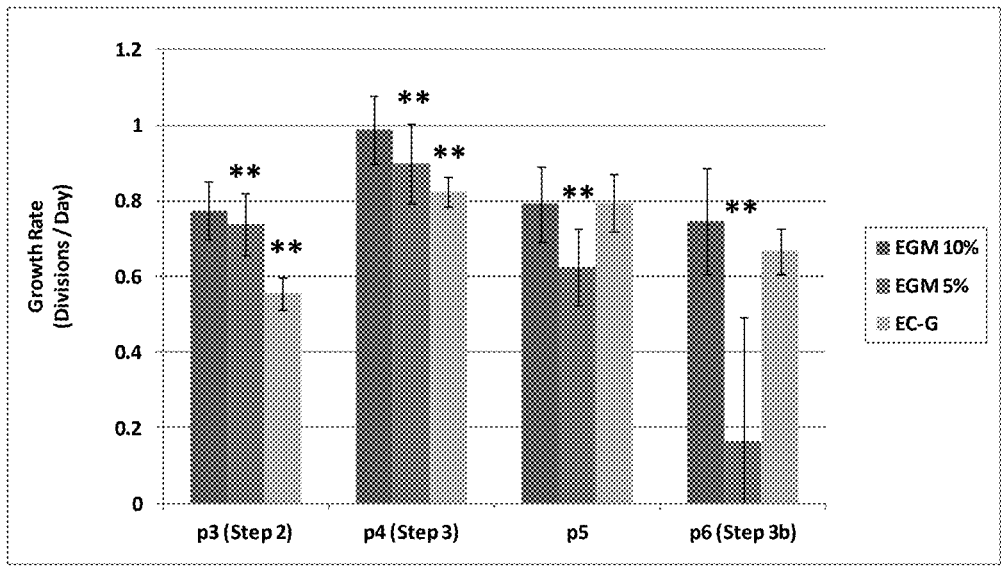
Figure 17:
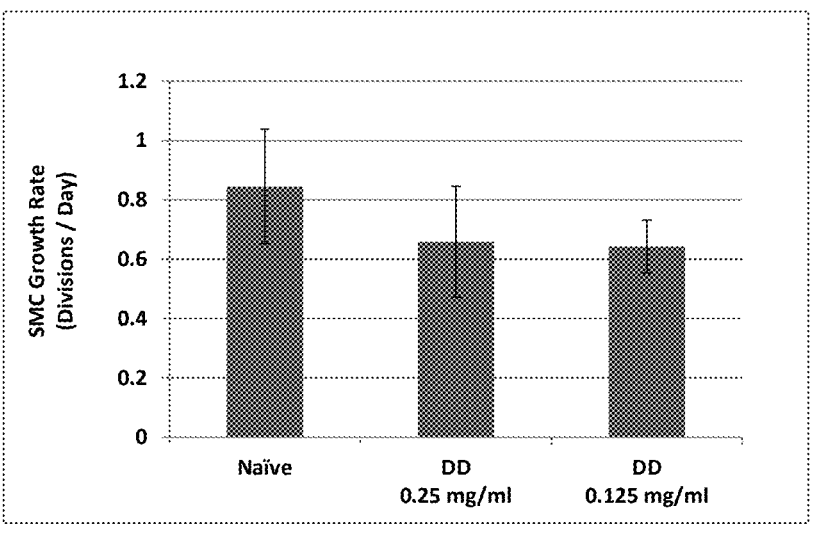
Figure 18:
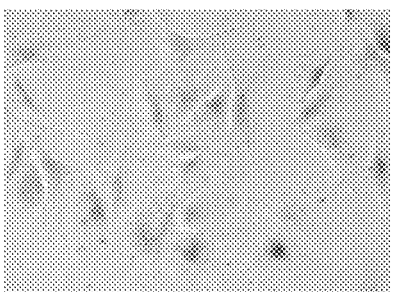
Figure 19:
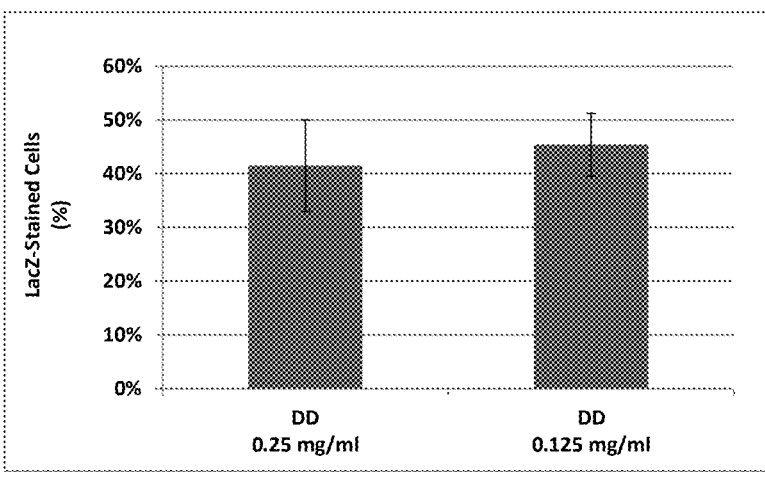
Figure 20A:
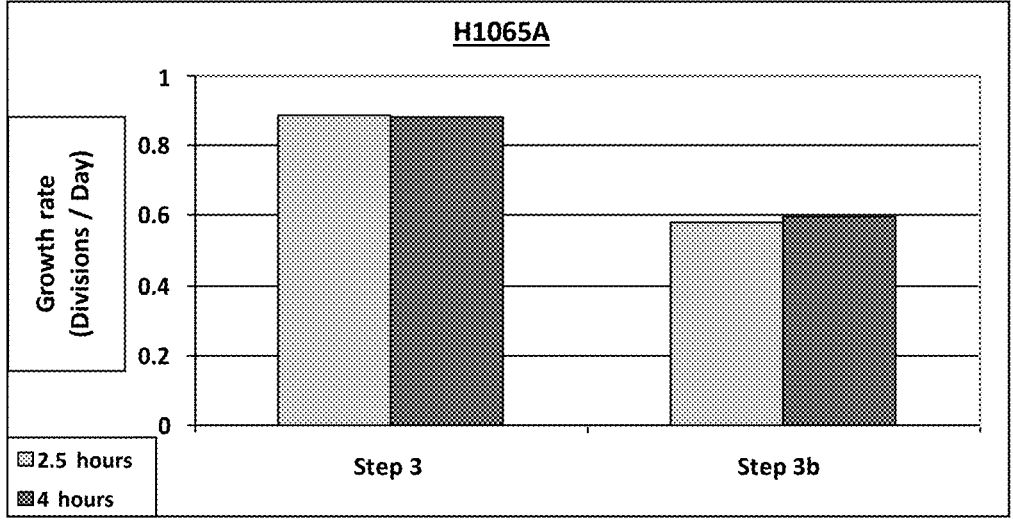
Figure 20B:
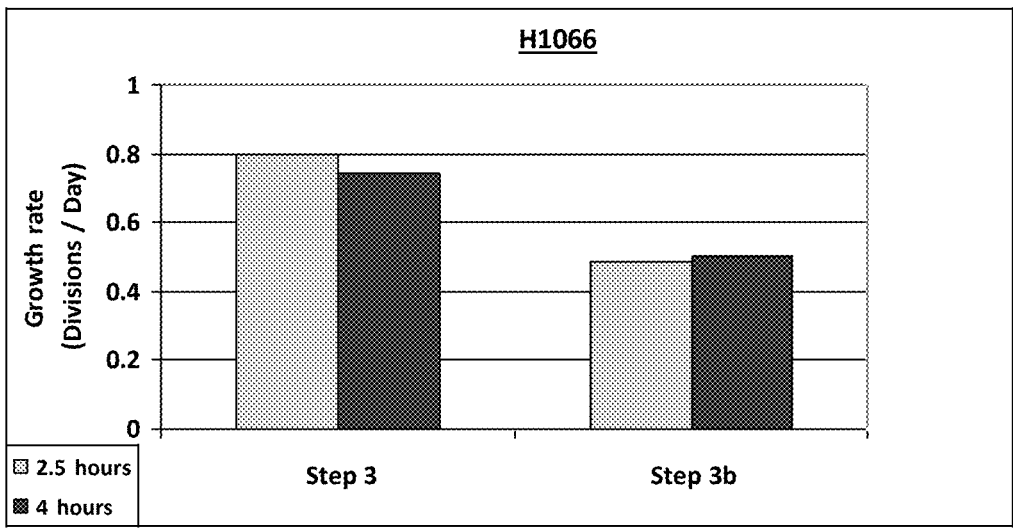
Figure 21A:
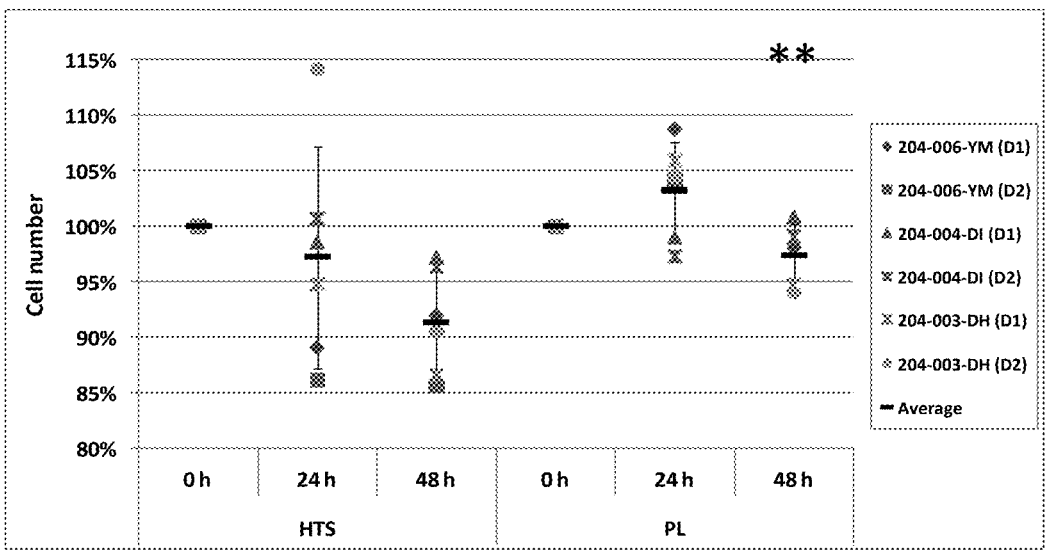
Figure 21B:
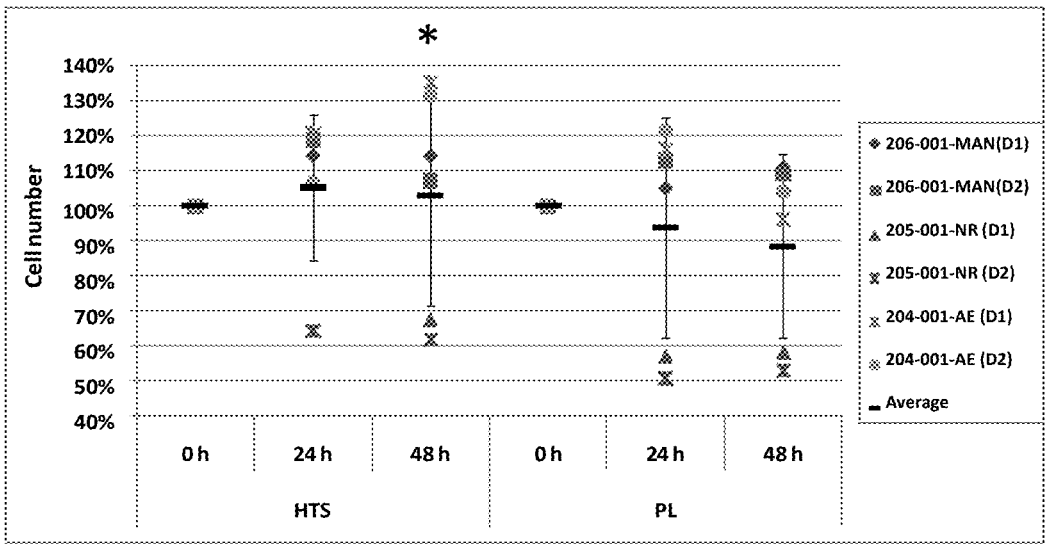
Figure 22A:
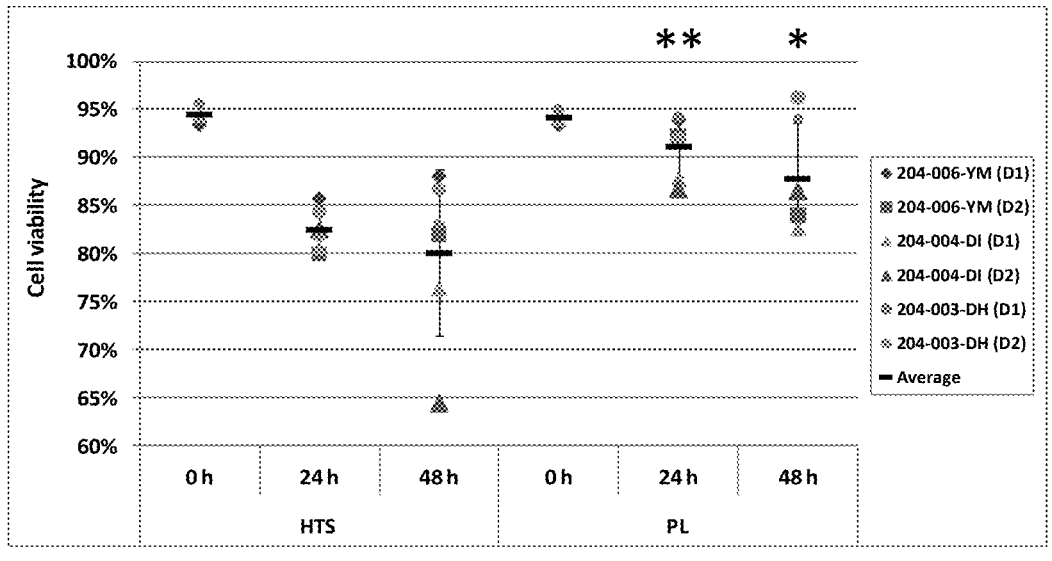
Figure 22B:
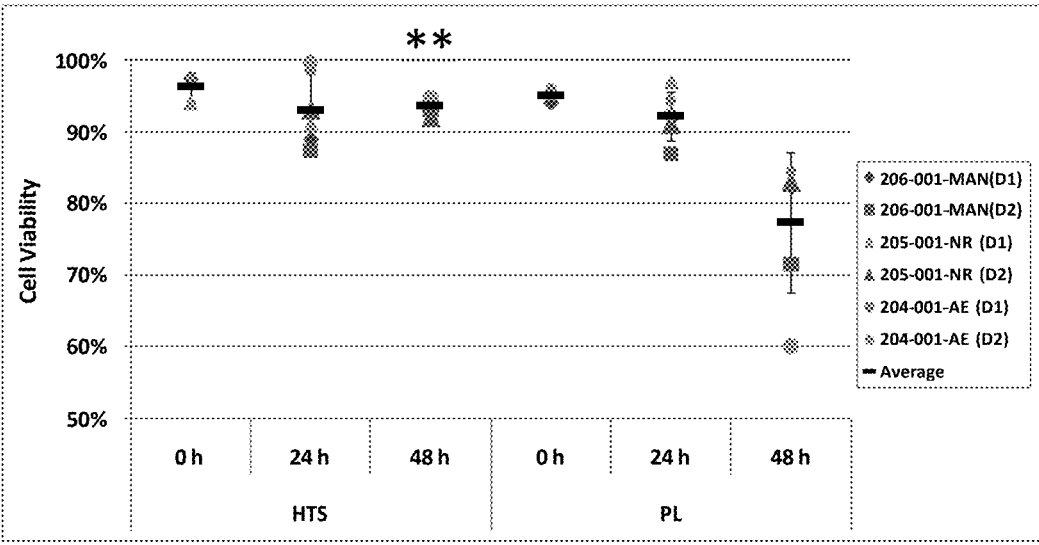
Figure 25A:
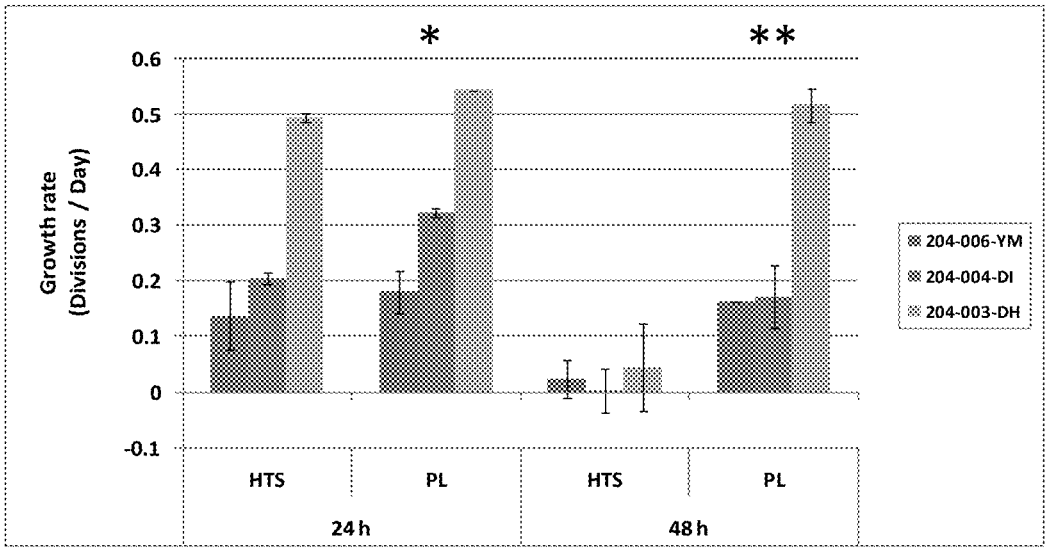
Figure 25B:
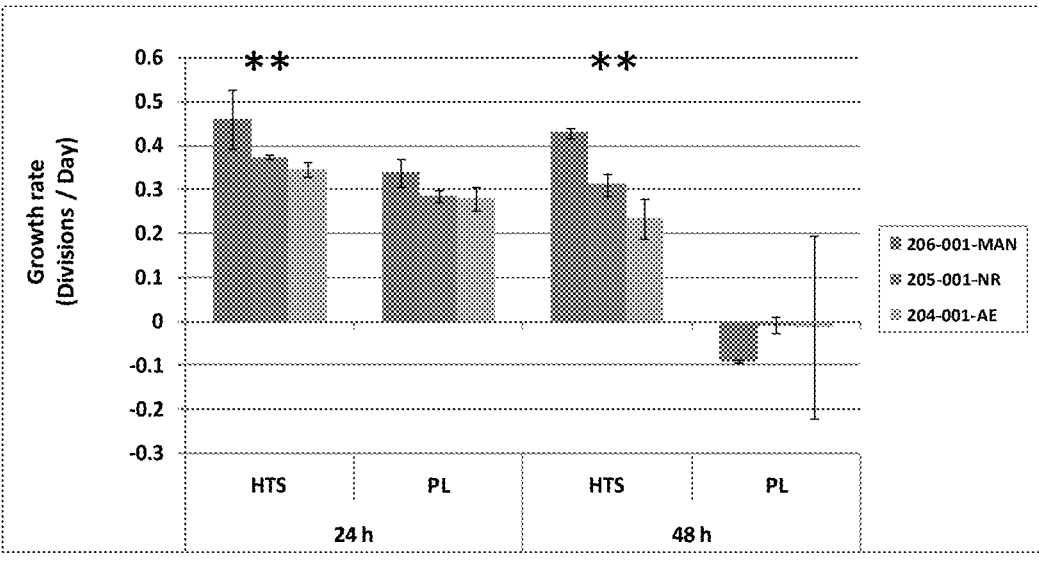

FIG. 1 is a histogram showing the effect of EC medium on growth rate of isolated endothelial cells (EC). EC isolated from five vein segments from 4 human donors (H1081B, H1082, H1085, H1086A and H1086B) were cultured in 6-well plates in either EC-G (black columns) or EGM medium supplemented with 10% Fetal Bovine Serum (FBS) (EGM10%, gray columns)), with medium change every 48-72 hours, until ready for harvest (¼-½ of culture plate surface covered) by trypsinization. Cells were counted by Coulter counter. Cell numbers represent two combined wells after the first post-isolation harvest (passage 1). Note the consistent, dramatic effect of EGM 10% on the growing cells;

FIG. 2 is a histogram showing the effect of SMC medium on growth rate of isolated smooth muscle cells (SMC). SMC isolated from six vein segments from 3 human donors (H1075A, H1075B, H1075C, H1076B, H1076C and H1077A) were cultured in 6-well plates in either SMC-G (black columns) or SMGM medium supplemented with 20% Fetal Bovine Serum (FBS) (SMGM20%, gray columns)), with medium change every 48-72 hours, until ready for harvest (¼-½ of culture plate surface covered) by trypsinization. Cells were counted by Coulter counter. Cell numbers represent two combined wells after the first post-isolation harvest (passage 1). H1076C and H1077A cells from SMGM 20% were harvested 7 days following isolation, while cells grown in SMC-G were harvested 10 days post-isolation. Note the consistent, dramatic effect of SMGM 20% on the growing cells;

FIG. 3 is a histogram showing the effect of FBS concentration of SMC medium on growth rate of isolated smooth muscle cells (SMC). SMC isolated from six vein segments from 4 donors (H1077B, H1078B, H1079, H1085, H1086A and H1086B) were cultured in 6-well plates in either SMGM supplemented with 15% FBS (SMGM 15%, black columns) or SMGM medium supplemented with 20% FBS (SMGM20%, gray columns), with medium change every 48-72 hours, until ready for harvest (¼-½ of culture plate surface covered) by trypsinization. Cells were counted by Coulter counter. Cell numbers represent two combined wells after the first post-isolation harvest (passage 1). Note the dramatic effect of SMGM20% on the growing cells;

FIG. 4 is a histogram showing the effect of EGM culture media, compared to EC-G medium, on the growth rate of endothelial cells (EC). EC cells were seeded and grown in different media, harvested, counted and reseeded at Day 4 and grown for 3 more days, then reharvested and counted. Columns represent the average growth rate over 7 days in all three donors+/−SD. Note the significant acceleration of growth rate with EGM medium+10% FBS;

FIG. 5 is a histogram showing the effect of SMGM and 231G culture media, compared to SMC-G medium, on the growth rate of smooth muscle cells (SMC). SMC cells were seeded and grown in different media, harvested, counted and reseeded at Day 4 and grown for 4 more days, then reharvested and counted. Columns represent the average growth rate over 8 days in all three donors+/−SD. Note the significant acceleration of growth rate with SMGM medium+20% FBS;

FIG. 6 is a histogram showing the effect of SMGM and 231G culture media, compared to SMC-G medium, on the growth rate of smooth muscle cells (SMC) following transduction. SMC cells were transduced with TGA-Lac Z, seeded and grown in different media, harvested, counted and reseeded at Day 4 and grown for 4 more days, then reharvested and counted. Columns represent the average growth rate over 8 days in both of the donors+/−SD. Note the significant acceleration of growth rate with SMGM medium+20% FBS;

FIG. 7 is a histogram showing the effect of SMGM and 231G culture media, compared to SMC-G medium, on the transduction rate of smooth muscle cells (SMC) following transduction. SMC cells were transduced with TGA-Lac Z, seeded and grown in different media for three days, then stained with X-Gal to monitor transduction rate. Columns represent the average transduction rate of SMC cells three days post-transduction, expressed as % LacZ positive cells out of total cell counts+/−SD;

FIGS. 8A-8B are histograms showing the average daily growth rate of SMC cells from 3 donors four days after transduction with TGA-LacZ (step 3, FIG. 8A), and after G418 selection (step 3b, FIG. 8B), indicating a clear advantage of SMGM 20% and 15% FBS over SMC-G medium for growth rate following SMC transduction;

FIG. 9 is a histogram showing the transduction rate of EC cells transduced in serum-free transduction medium with and without added growth factors. EC cells were transduced with TGA-Lac Z, seeded and grown in EGM medium+2% FBS for four days, then stained with X-Gal to monitor transduction rate;

FIG. 10 is a histogram showing the growth rate of EC cells transduced in serum-free transduction medium with and without added growth factors. Transduced EC cells from three donors were seeded and grown for four days in EMG medium+2% FBS, harvested and counted. Columns represent the average growth rate over 4 days in all three donors+/−SD;

FIG. 11 is a histogram showing the effect of EGM culture medium, supplemented with different amounts of FBS, compared to EC-G medium, on the growth rate of endothelial cells (EC) following transduction. EC cells were transduced with TGA-Lac Z, seeded and grown in the different media for four days, harvested and counted. Columns represent the average growth rate over 4 days in both donors, expressed as the percentage of TGA LacZ transduced EC growth rate at EGM medium+15% FBS, +/−SD;

FIG. 12 is a histogram showing the effect of EGM culture medium, supplemented with different amounts of FBS, compared to EC-G medium, on the transduction rate of endothelial cells (EC) with TGA LacZ. Transduced EC cells from two donors were seeded and grown in the different media for three days, then stained with X-Gal to monitor transduction rate;

FIG. 13 is a histogram showing the effect of EGM culture medium, supplemented with different amounts of FBS, compared to EC-G medium, on the growth rate of endothelial cells (EC) following transduction, at different stages of the culture process. EC cells were transduced with TGA-Lac Z, seeded and grown, in the presence of a selection agent (neomycin), in the different media, harvested, reseeded and counted at early (p3, p4) passages, passage 5 and step 3b (passage 6, end of selection). Columns represent the average growth rate over the duration, expressed as the growth rate (divisions/day)+/−SD for all three donors;

FIGS. 14A-14D are histograms showing the effect of EGM culture medium supplemented with different amounts of FBS, compared to EC-G medium, on the transduction rate and secretion of Ang-1 by endothelial cells (EC) following transduction with Ang-1, at different stages of the culture process. EC cells from three donors were grown in EC-G medium or EGM medium+10% FBS, transduced with retroviral Ang-1 vector, and cultured in EC-G medium or EGM medium+10% FBS prior to (FIGS. 14A and 14C) and following (14B and 14D) 10 days selection with G418. Immunohistochemical assessment of Ang-1 expression in the transduced cells before (FIG. 14A) and after (FIG. 14B) selection reveals a clear advantage in transduction rate for cells cultured in EMG+10% FBS. ELISA assay of Ang-1 secreted by the transduced cells before (FIG. 14C) and after (FIG. 14D) selection reveals a strong dependence of the EC-G medium-grown cells on G418 selection, but none of the same effect with cells cultured in EMG+10% FBS;

FIGS. 15A-15C are photographs of SMC during and immediately following transduction with TGA-LacZ vector showing the positive effect of pretreatment with 0.125 mg/ml DEAE Dextran (DD). SMC were incubated for 1 minute with either 0.25 mg/ml DD (FIG. 15B), or 0.125 mg/ml DD (FIG. 15C), prior to 2.5 hours transduction with TGA-LacZ vector, and then cultured as described. FIG. 15A shows naïve cells, unexposed to either the viral vector or the DD;

FIG. 16 is a histogram showing the effectiveness of pre-treatment of the SMCs with 0.125 mg/ml DD, compared to pretreatment with 0.25 mg/ml DD, on early post-transduction proliferation. SMC of two human donors (H1058B and H1071A) were seeded for transduction on 6-well plates ($1.3 \times 10^5$ cells/well) in duplicates. The cells were transduced the next day with TGA retrovirus following treatment with either 0.25 mg/ml or 0.125 mg/ml DEAE Dextran. Transduced cells were harvested and counted 2 days after transduction. Results are average of cells from 2 donors, seeded and counted in duplicates ±SD. "Naïve cells" are SMCs unexposed to either the viral vector or the DD;

FIG. 17 is a histogram showing the effectiveness of pre-treatment of the SMCs with 0.125 mg/ml DD, compared to pretreatment with 0.25 mg/ml DD, on late post-transduction proliferation. SMC of two human donors (H1058B and H1071A) were seeded for transduction and transduced as described for FIG. 15A-C. Transduced cells were seeded onto 12-well plates (6,000-10,000 cells/well) in triplicates. Medium was changed every 2 days. After five days, cells were harvested and counted. Results are average of cells from 2 donors, transduced in duplicates, seeded and counted in triplicates±SD. "Naïve cells" as in FIG. 16;

FIG. 18 is a photograph showing transduced SMC fixed and stained for Lac-Z with X-gal, two days following transduction. SMC were pretreated, seeded for transduction and transduced as described for FIG. 16. Lac-Z-positive cells stain blue;

FIG. 19 is a histogram showing the effect of pre-treatment of the SMCs with 0.125 mg/ml DD, compared to pretreatment with 0.25 mg/ml DD, on SMC transduction rate with a viral vector. SMC were pretreated, seeded for transduction and transduced as described for FIG. 16, and stained for LacZ expression with X-gal. 10-15 representative fields were photographed and cells were counted by Coulter counter. Cells were stained and counted in duplicates. Results are shown here as percentage of TGA-positive cells (stained blue) out of total number of cells. Average of results from 2 donors ±SD;

FIGS. 20A and 20B are a histograms showing the growth rate of endothelial cells from two separate donors, when transduced with an angiopoietin-1 retroviral vector for different transduction times (white columns=2.5 hours transduction, black columns=4 hours transduction), at 2 days (step 3) and 13 days (step 3a) after transduction (step 3b includes 10 days of G418 selection). Note the similarity of growth rates between the two transduction regimens;

FIGS. 21A-21B are graphs showing the effect of different hypothermic preservative solutions on the survival of transduced vascular cells in hypothermic conditions. Primary isolated vascular (saphenous vein) cells were transduced with retroviral vectors encoding angiogenic factors (endothelial cells, "EC", FIG. 21A transduced with Ang-1, and smooth muscle cells, "SMC", FIG. 21B, transduced with VEGF$_{165}$), washed and suspended in either an intracellular-type, HEPES-buffered hypothermic preservation solution (HTS) or in an isotonic, bicarbonate-buffered hypothermic preservation solution with albumin (PL). The cells were counted by Coulter counter (0 hrs), transferred to 4-8° C. and recounted at 24 and 48 hours. Results ("Cell number") are expressed as a percentage of the initial cell number at 0 hrs (100%) in an average of duplicate samples from three human donors. Note the differential effect of the hypothermal preservation solutions on EC and SMC cells;

FIGS. 22A-22B are graphs showing the effect of different hypothermic preservative solutions on the viability of transduced vascular cells in hypothermic conditions. Primary isolated vascular (saphenous vein) cells were transduced with retroviral vectors encoding angiogenic factors (endothelial cells, "EC", FIG. 22A transduced with Ang-1, and smooth muscle cells, "SMC", FIG. 22B, transduced with $VEGF_{165}$), washed and suspended in either an intracellular-type, HEPES-buffered hypothermic preservation solution (HTS) or in an isotonic, bicarbonate-buffered hypothermic preservation solution with albumin (PL). The cell suspensions were sampled for assessment (microscopic) of viability with trypan blue at 0 hrs, then transferred to 4-8° C. and reassessed at 24 and 48 hours. Results ("Cell viability") are expressed as a percentage of live cells/total number of cells (100%) in an average of duplicate samples from three human donors. Note the differential effect of the hypothermal preservation solutions on EC and SMC cells;

FIGS. 23A-23D are photographs showing the effect of different hypothermic preservative solutions on the condition of transduced vascular cells cultured following incubation in hypothermic conditions. Primary isolated vascular (saphenous vein) cells were transduced with retroviral vectors encoding angiogenic factors (endothelial cells, "EC", FIGS. 23A and 23B transduced with Ang-1, and smooth muscle cells, "SMC", FIGS. 23C and 23D, transduced with $VEGF_{165}$), washed and suspended in either an intracellular-type, HEPES-buffered hypothermic preservation solution (HTS)(FIGS. 23B and 23D) or in an isotonic, bicarbonate-buffered hypothermic preservation solution with albumin (PL) (FIGS. 23A and 23C) for 24 hours at 4-8° C. Following the hypothermic incubation, cells were seeded onto 6-well plates or flasks in growth medium, cultured for 24 hours and photographed. Note the differential effect of the hypothermal preservation solutions on the density and adherence to the culture plate surface of the EC and SMC cells;

FIGS. 24A-24D are photographs showing the effect of different hypothermic preservative solutions on the condition of transduced vascular cells cultured 24 hours following incubation in hypothermic conditions. Primary isolated vascular (saphenous vein) cells were transduced with retroviral vectors encoding angiogenic factors (endothelial cells, "EC", FIGS. 24A and 24B transduced with Ang-1, and smooth muscle cells, "SMC", FIGS. 24C and 24D, transduced with $VEGF_{165}$), washed and suspended in either an intracellular-type, HEPES-buffered hypothermic preservation solution (HTS)(FIGS. 24B and 24D) or in an isotonic, bicarbonate-buffered hypothermic preservation solution with albumin (PL) (FIGS. 24A and 24C) for 48 hours at 4-8° C. Following the hypothermic incubation, cells were seeded onto 6-well plates or flasks in growth medium, cultured for 24 hours and photographed. Note the differential effect of the hypothermal preservation solutions on the density and adherence to the culture plate surface of the EC and SMC cells;

FIGS. 25A-25B are graphs showing the effect of different hypothermic preservative solutions on cell proliferation rate of transduced vascular cells cultured for 72 hours following incubation in hypothermic conditions. Primary isolated vascular (saphenous vein) cells were transduced with retroviral vectors encoding angiogenic factors (endothelial cells, "EC", FIG. 25A transduced with Ang-1, and smooth muscle cells, "SMC", FIG. 25B, transduced with $VEGF_{165}$), washed and suspended in either an intracellular-type, HEPES-buffered hypothermic preservation solution (HTS) or in an isotonic, bicarbonate-buffered hypothermic preservation solution with albumin (PL) for 24 or 48 hours at 4-8° C. Following the hypothermic incubation, cells were seeded onto 6-well plates or flasks in growth medium, cultured for 72 hours, harvested and counted by Coulter counter. Cell growth rate is expressed as the average number of cell divisions in 24 hours of duplicate samples from three human donors. Note the striking differential effect of the hypothermal preservation solutions on EC and SMC cell growth rate following 48 hours hypothermic incubation.

Figure 26:
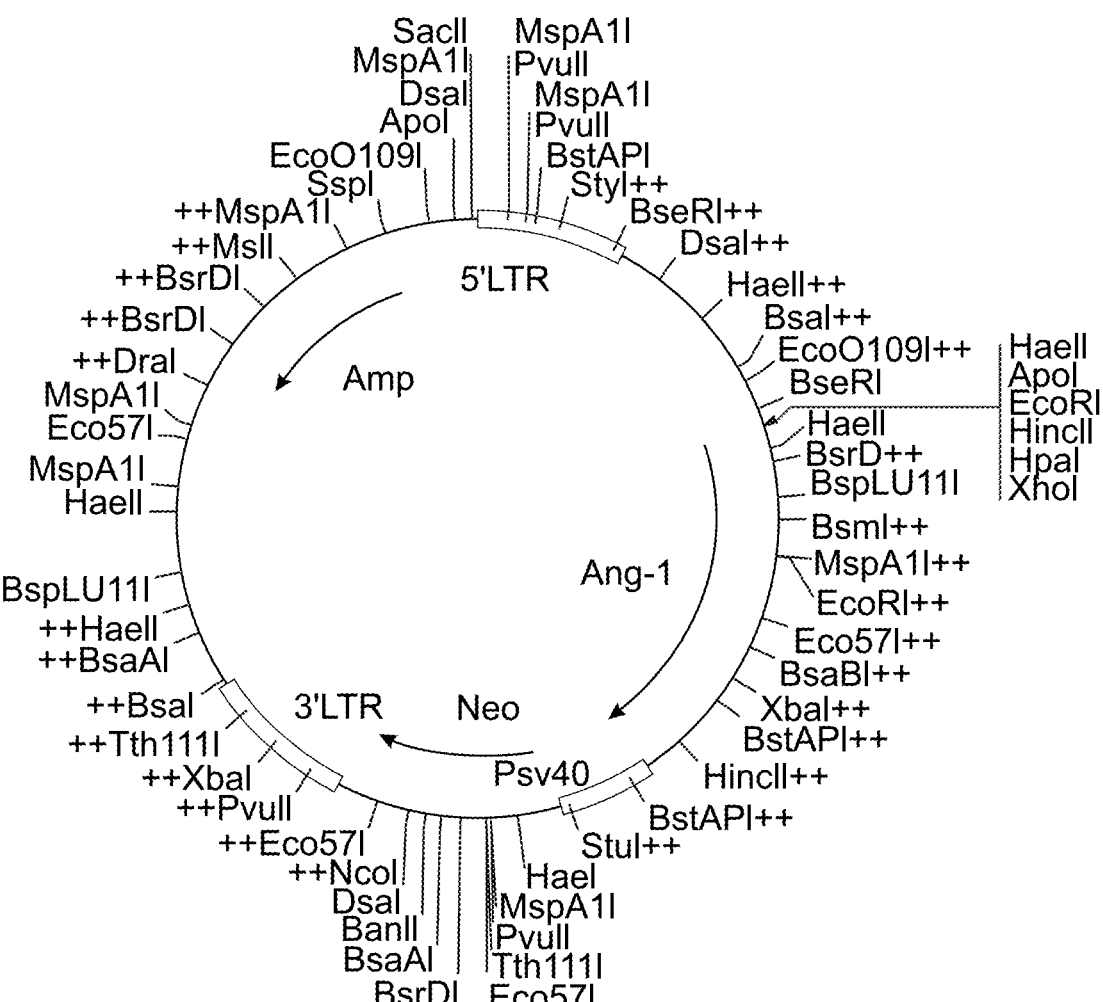

FIG. 26 shows nucleic acid constructs and sequences of Angiopoietin-1 and VEGF 165.

DESCRIPTION OF SPECIFIC EMBODIMENTS OF THE INVENTION

The present invention relates to fields of chemistry, biochemistry, cellular biology, genetic engineering and medicine. In particular, it relates to methods for preparation of transduced cells for storage prior to use. Specifically, it relates to methods of preconditioning vascular cells for transduction, methods of transduction, methods of preserving transduced cells and the use of the preserved transduced cells in the clinic.

Aspects of the invention are concerned with:
(i) transducable vascular cell compositions;
(ii) methods for cell transduction;
(iii) methods for hypothermal preservation of transduced cells;
(iv) hypothermally preserved transduced vascular cells;

All or embodiments thereof are described herein in order to generate cells for use in therapy or related disorders.

It will be appreciated that the instant invention can be directed to i+ii+iii+iv; i+ii+iii; i+ii; ii+iii+iv; ii+iii; or iii−iv.

I. Transducable Vascular Cell Compositions

The instant inventors have uncovered methods enabling effective preparation of vascular tissue cells (e.g. SM and EC cells) for retroviral transduction with constructs encoding pro-angiogenic factors. Vascular tissue cells prepared according to these methods are characterized by enhanced proliferation and rates of transduction and secretion of the recombinant pro-angiogenic factors, and can be prepared for use, inter alia, in transplantation for inducing neovascularization to treat vascular diseases.

The inventors have shown that combinations of specific vascular cell isolation procedures, culture conditions (see Example 1) and pre-conditioning of the vascular cells (see Example 2) results in vascular endothelial and smooth muscle cells having greater viability prior to and following retroviral transduction. In particular, the inventors have uncovered that reduction of the DEAE Dextran concentration in Smooth Muscle cell preconditioning provides enhanced transduction rates and viability/growth rate of the transduced cells (see Example 2, below). Further, the inventors have uncovered that use of EGM medium (Endothelial Growth Medium (EGM)™-2 Bullet Kit medium) and SMGM (SmGM-2™ Bulletkit™ (Lonza, Ltd., Basel, Switzerland Cat #CC-3182)), before and following transduction results in greater transduction rates and growth rates of the isolated vascular cells (see Example 1).

Thus, according to one aspect, the present invention relates to human smooth muscle (SM) cells preconditioned for transduction with a retroviral nucleic acid construct or lentivirus nucleic acid construct comprising a polynucleotide sequence encoding a $VEGF_{165}$ polypeptide, wherein the preconditioning comprises contacting the SM cells with between 0.125 and 0.9 mg/ml DEAE-Dextran, and wherein the SM cells are characterized by at least one of increased transduction rate and increased proliferation following transduction, as compared to similar SM cells preconditioned with 1.0 mg/ml DEAE-Dextran or greater.

According to another aspect, the present invention relates to human endothelial (EC) cells preconditioned for transduction with a retroviral nucleic acid construct or lentivirus nucleic acid construct comprising a polynucleotide sequence encoding an Angiopoietin-1 (Ang-1) polypeptide, wherein the preconditioning comprises:

(a) isolating the EC cells from venous tissue with an isolation medium comprising Endothelial Growth Medium (EGM)™-2 Bullet Kit medium and 10% Fetal Bovine Serum;

(b) culturing the isolated EC cells with an EC culture medium comprising Endothelial Growth Medium (EGM)™-2 Bullet Kit medium, and (c) preconditioning the human vascular endothelial cells with 1.0 mg/ml DEAE-Dextran, wherein the EC cells are characterized by at least one of increased transduction rate and increased proliferation following transduction, as compared to similar EC cells isolated and/or preconditioned without Endothelial Growth Medium (EGM)™-2 Bullet Kit medium.

Vascular cells (SM and EC) suitable for use with the methods of the present invention include vascular cells freshly isolated from vascular tissue as well as preserved vascular cells and cultured vascular cells. Methods for smooth muscle cell isolation from vascular tissue are well known in the art.

According to the present invention, vascular endothelial cells and smooth muscle cells are removed from an individual for transduction according to the methods of the invention. The vascular endothelial cells and smooth muscle cells need not be from the same blood vessel, although most conveniently they are isolated from the same segment of vascular tissue that is removed from the patient. The vascular tissue can be removed from any of several sites, but should be from a site that causes the least amount of discomfort and potential harm to the patient, e.g., superficial veins such as the lesser saphenous vein, greater saphenous vein, cephalic vein, and other similar veins. The amount of vessel which is removed should be sufficient to supply endothelial and smooth muscle cells for transduction and propagation at a low passage number, e.g., typically at least approximately 2 cm and up to 10 cm or more in length, although this may vary widely depending on the vessel, the condition of the patient, etc.

Endothelial cells can be selectively removed from the excised blood vessel or other micro- or macrovascular tissue according to techniques known to those in the art. See, e.g., Vohra et al., Vasc. Surg. 22: 393-397 (1989); Folkman et al., Proc. Natl. Acad. Sci. USA 76: 5217-5221 (1979); Kern et al., J. Clin. Invest. 71: 1822-1829 (1983) and Sterpetti et al., J. Surg. Res. 48:101-106 (1990), and in particular, WO 02/12539, which are incorporated herein by reference. For example, a solution of collagenase can be introduced into an excised vessel up to approximately 48 hours after vein stripping, which is then incubated for a short period and the cells then flushed from the vein. Endothelial cells are then collected and can be expanded by cultivation in an appropriate culture medium.

In some embodiments, the vascular cells are isolated from vascular tissue in an isolation medium similar to growth medium, and in other embodiments the isolation medium differs from growth medium in at least one component. In specific embodiments, vascular endothelial cells are isolated in EGM medium (EGM-2™ BulletKit™ medium (Lonza, Ltd., Basel, Switzerland, Cat #CC-3162)) supplemented with 10% fetal bovine serum (FBS). Endothelial cell isolation can be performed under standard conditions (e.g, humidified incubator with 5% $CO_2$/95% air at 37° C.). Following isolation, when the isolated EC form large colonies that cover ¼-½ of the plate surface the cells can be harvested (e.g. enzymatically: trypsinized) and transferred to a tissue culture plate (passage 1, p1). In some embodiments, the tissue culture plate is pre-coated with gelatin or fibronectin.

After the endothelial cells are harvested from the excised vessel the smooth muscle cells can be removed using established techniques, e.g., enzyme digestion and/or outgrowth from cultured pieces of vessel. For enzyme digests the de-endothelialized vessel segments can be treated with an appropriate enzyme solution, e.g., collagenase. To isolate smooth muscle cells from cultured explants, small pieces of enzyme treated vessel (e.g., 1-2 mm$^2$) are plated in an appropriate isolation medium. In specific embodiments, the SMC isolation medium comprises SMGM (SmGM-2™ Bulletkit™ (Lonza, Ltd., Basel, Switzerland, Cat #CC-3182)) supplemented with 20% serum (e.g. FBS). Isolated SMC cells can then be incubated at 5% $CO_2$/95% air at 37° C. When outgrowth of smooth muscle cells is attained tissue fragments are removed and the smooth muscle cells harvested and expanded.

According to some embodiments, the human SM and EC cells can be freshly isolated cells, cryopreserved and thawed SM and EC cells and/or cultured SM and EC cells, or any combination thereof.

As used herein, the term "fresh" or "freshly isolated" SM or EC cells refers to cells that have been isolated from the tissue, and have not been cultured or preserved. Such freshly isolated SM cells or EC may differ in the composition of the cell populations. In general, vascular smooth muscle cells may be divided into contractile and synthetic smooth muscle cells, and are characterized by expression of smooth muscle cell markers such as, but not limited to alpha-SM actin, Smooth muscle myosin heavy chain, SM22alpha, Smoothelin, Telokin, Desmin CRBP-1, Smemb, Meta-vinculin, VE-cadherin, Caldesmon/CALD1, Calponin 1, Hexim 1, Histamine H2 R, Motilin R/GPR38 and Transgelin/TAGLN. Vascular endothelial cells are characterized by expression of markers such as, but not limited to Factor VIII-related antigen, CD31/PECAM-1, Angiotensin-converting enzyme, Type-1 scavenger receptor, Vascular endothelial cadherin, CD34, CD102/ICAM-2, CD51/61 (vitronectin receptor), CD105/endoglin, CD36, CD73/VAP-1, S-endo-1/MUC18, HEMCAM, Sca-1, AAMP, CD106NCAM-1, CD54/CAM-1, CD62E, CD62P, VEGFR-1, VEGFR-2, Tie-1, Tie-2, FB5, Fibronectin ED-B. "Freshly isolated" SM or EC cells can be SM or EC cells isolated within minutes, an hour, 1-5 hours or up to 24 hours from harvesting the vascular tissue for cell isolation.

Following isolation, the vascular cells can be characterized according to morphology, FACS and/or immunohistochemistry and purity of the isolated cell populations assessed. In some embodiments, EC cells are identified and assessed by staining with anti-human CD31 for positive identification and with anti-alpha-human smooth muscle actin (α-SMA) for identification of smooth muscle cells and fibroblasts within the EC population. In some embodiments, SMC cells can be identified and purity assessed with anti-alpha-human smooth muscle actin ($\alpha$-SMA). Criteria for purity of the vascular cell cultures can be expressed in terms of positive identification of designated markers. In some embodiments, SMC cell cultures are at least 50%, at least 55%, at least 60%, at least 65%, at least 70%, at least 75%, at least 80%, at least 85%, at least 90%, at least 95% $\alpha$-SMA positive staining.

In some specific embodiments, the EC cell cultures are at least 65% CD31-positive and less than 15% $\alpha$-SMA positive. In some embodiments, the SMC cell cultures are at least 60% $\alpha$-SMA positive.

In some embodiments, SMC cell cultures are at least 50%, at least 55%, at least 60%, at least 65%, at least 70%, at least 75%, at least 80%, at least 85%, at least 90%, at least 95% CD31 positive staining and less than 30%, less than 25%, less than 20%, less than 15%, less than 10%, less than 5% positive staining for $\alpha$-SMA.

In some specific embodiments, the EC cell cultures are at least 65% CD31-positive and less than 15% $\alpha$-SMA positive. In some embodiments, the SMC cell cultures are at least 60% $\alpha$-SMA positive.

In some cases, the vascular tissue is preserved (e.g. cryopreserved) vascular tissue.

As used herein, the term "cryopreserved" SM or EC cells refers to cells that have been preserved in ultra-low temperatures, within a special buffer, and which can be revived by thawing, according to well known protocols. The cryopreserved SM or EC cells can be cells that were preserved when "freshly isolated", or cells that were cultured prior to cryopreservation.

As used herein, the term "cultured vascular cells", "cultured SM" or "cultured EC cells" refers to cells which have been transferred to a culture medium for propagation. In some embodiments, the vascular cells (e.g. EC and SM cells) are cultured prior to transduction, e.g. before being prepared for transduction. SM and EC cells can be cultured from either freshly isolated or cryopreserved cells, can be primary cell cultures (cultured from fresh tissue) or cultured from an existing cell culture, or can be cultured cells originating from a cell culture line.

Suitable culture media and conditions for culturing vascular cells prior to, during or after transduction are well known in the art. Such media include, but are not limited to, MCBD 131®, Dulbecco's Modified Eagle's Medium® (DMEM), DMEM F12 Medium®, Eagle's Minimum Essential Medium®, F-12K Medium®, Iscove's Modified Dulbecco's Medium®, RPMI-1640 Medium®, M-199 and serum-free media. In specific embodiments endothelial cells may be cultured in EGM-2™ BulletKit™ medium (Lonza, Ltd., Basel, Switzerland, Cat #CC-3162) and smooth muscle cells may be cultured in SmGM-2™ Bulletkit™ (Lonza, Ltd., Basel, Switzerland Cat #CC-3182). Many media are also available as low-glucose formulations, with or without sodium pyruvate.

In some embodiments the growth medium comprises serum, for example, fetal bovine serum (FBS). In some embodiments, the medium comprises serum (e.g. FBS) in a range between 5 and 25%, 10 and 20% and 10-15%. In some embodiments the growth medium comprises 5%, 8%, 10%, 12%, 15%, 18%, 20%, 22% or 25% serum. In particular embodiments, endothelial cell growth medium comprises 10% FBS. In particular embodiments, smooth muscle cell growth medium comprises 15% FBS.

Additional supplements also can be used advantageously to supply the cells with the necessary trace elements for optimal growth and expansion. Such supplements include insulin, transferrin, sodium selenite and combinations thereof. These components can be included in a salt solution such as, but not limited to, Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids, however, some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine.

Hormones also can be advantageously used in the cell cultures of the present invention and include, but are not limited to, D-aldosterone, diethylstilbestrol (DES), dexamethasone, beta-estradiol, hydrocortisone, insulin, prolactin, progesterone, somatostatin/human growth hormone (HGH), thyrotropin, thyroxine and L-thyronine.

Lipids and lipid carriers also can be used to supplement cell culture media, depending on the type of cell and the fate of the differentiated cell. Such lipids and carriers can include, but are not limited to, cyclodextrin (alpha, beta, gamma), cholesterol, linoleic acid conjugated to albumin, linoleic acid and oleic acid conjugated to albumin, unconjugated linoleic acid, linoleic-oleic-arachidonic acid conjugated to albumin and oleic acid unconjugated and conjugated to albumin, among others.

Vascular cells (e.g. EC and SMC) may also be cultured in low-serum or serum-free culture medium. Serum-free medium used to culture cells is described in, for example, U.S. Pat. No. 7,015,037.

The inventors have uncovered that culturing of vascular epithelial cells (EC cells) in growth medium+serum without additional growth factors is often equivalent, in the effect on cell proliferation, to growth in medium with added growth factors (see Example 1). In particular, removal of factors including hydrocortisone, hEGF, VEGF, hFGF-B, R3-IGF-1, ascorbic acid and heparin form the growth medium did not significantly negatively affect EC cells growth. Thus, in some embodiments, vascular cells can be cultured in medium lacking at least one added growth factor selected from the group consisting of hydrocortisone, hEGF, VEGF, hFGF-B, R3-IGF-1, ascorbic acid and heparin. In some embodiments, the vascular epithelial cells are cultured in medium comprising EGM and FBS and lacking at least one, at least two, at least three added growth factors selected from the group consisting of hydrocortisone, hEGF, VEGF, hFGF-B, R3-IGF-1, ascorbic acid and heparin. In some embodiments the EC cells are cultured in a medium comprising EGM and lacking all added growth factors selected from the group consisting of hydrocortisone, hEGF, VEGF, hFGF-B, R3-IGF-1, ascorbic acid and heparin.

According to some embodiments of the present invention, the vascular cells are cultured following isolation and prior to transduction in growth medium. In specific embodiments, prior to transduction, the isolated EC cells are cultured in EGM-2™ BulletKit™ medium supplemented with 10% FBS. In specific embodiments, prior to transduction, the isolated SMC cells are cultured in SmGM-2™ BulletKit™ medium supplemented with 15% FBS.

According to some embodiments, the vascular cells of the invention, by virtue of the preconditioning and/or culturing conditions, are characterized by at least one of increased transduction rate and increased proliferation following transduction, as compared to similar vascular cells isolated and preconditioned without the indicated conditions. In particular, EC cells of the invention are characterized by at least one of increased transduction rate and increased proliferation following transduction, as compared to similar EC cells isolated and/or preconditioned without Endothelial Growth Medium (EGM)™-2 Bullet Kit medium, and SMC cells of the invention are characterized by at least one of increased transduction rate and increased proliferation following transduction, as compared to similar SM cells preconditioned with 1.0 mg/ml DEAE-Dextran or greater.

As used herein, the term "proliferation" is defined as the growth or increase in cell number of a population of cells. Cell proliferation assays are mainly designed based on the concepts of quantifying the increase/decrease in number of cells per volume of medium, measuring rate of DNA replication, analysis of metabolic activity and/or cell surface antigen recognition. Increase or decrease in the number of cells per volume medium can be evaluated by a cell or particle counter, such as a Coulter counter, which counts and sizes particles suspended in electrolytes by electrical zone sensing. In addition, suitable assays of DNA replication rate include, but are not limited to incorporation of radioactive or labelled nucleotide analogues, that is, $^3$H-thymidine- and BrdU-based assays. Suitable metabolic activity assays include, but are not limited to 3-(4,5-dimethylthiazol-2-yl)-2,5-diphenyltetrazolium bromide (MTT) assay, (2,3-Bis-(2-Methoxy-4-Nitro-5-Sulfophenyl)-2H-Tetrazolium-5-Carboxanilide)(XTT) assay, water soluble tetrazolium (WST) salts assay, resazurin assay and assays of ATP. Suitable assays of targets antigens present in proliferating cells include, but are not limited to assays of markers such as Ki-67, topoisomerase IIB, phosphohistone H3 and PCNA. In some embodiments, vascular cell proliferation is assessed by measuring the cell density in a sample, for example, after harvest at one of the passages of the cell culture, by coulter counter, and comparing the number of cells (e.g. total number of cells in the culture vessel, number of cells per volume of cell culture, etc.) to a previous value of the same or another cell culture. In some embodiments, the growth rate or proliferation rate of cells in a culture is expressed as the number of cell divisions (number of cells at time "t" minus number of cells at time "0" divided by number of cells at time "0") per unit time, e.g. divisions per day. In other embodiments, the growth rate is expressed as a fraction or percentage of the growth rate of the cells under standard or predetermined conditions (e.g. "Difference from Growth Rate in EGM+15% FBS, FIG. 11). Proliferation of cultured vascular cells can also be expressed as the fold increase, (e.g., expansion or fold expansion) of vascular cells, as compared to the original vascular cell fraction before culture or before harvesting and reseeding.

In one embodiment, cell proliferation of populations of cultured vascular cells according to the present invention is measured at a predetermined time after seeding the vascular cells in culture (for example, about 10 hours, 12 hours, about 1, 2, 3, 4, 5, 6, 7, 8, 9, 10 days, about 1, 2, 3, 4 weeks or more).

As used herein, the term "transduction rate" is defined as the efficiency of transfer of the retroviral vector and the DNA comprised therein into cells in the transduction process. It will be appreciated that the apparent transduction rate can be affected not only by the number of cells which actually undergo transduction, but also by the viability of the transduced cells and their ability to continue to proliferate in culture. In some embodiments, transduction rate of the claimed vascular cells is assayed by a metabolic or other reporter reaction of the transduced cells, such as reaction of the beta-galactosidase in Lac-Z expressing cells with bromochloroindoxyl galactoside (X-Gal) (galactose-indole compound), resulting in characteristic blue-hued stain in the presence of the beta-galactosidase. Such an assay can be carried out on a sample of the cells deposited on a slide, for ease of detection and counting microscopically. Assay of transduction rate can also be performed based on detection of vector DNA, or its expression, in the transduced cells and/or the progeny thereof. For example, a sample of the cells from the culture can be seeded onto slides, and recombinant products detected in the cells by, for example, immunohistochemistry (IHC).

The proportion of cells comprising the vector DNA can be the basis for assessment of transduction rate. Transduction rate may also include a calculation of the proportion of cells comprising the retroviral vector relative to the total number of cells exposed to the transduction process (cell number pre-transduction). In other embodiments, transduction rate can be evaluated by quantifying the proportion of cells detected having the expression product of the transduced vector, for example, using anti-Ang-1 or anti VEGF antibodies. In yet other embodiments, the transduction rate is assessed by the detection in the medium of a recombinant expression product targeted for secretion from the transduced vascular cell, such as by enzyme linked immunosorbent assay (ELISA) of the culture medium with an Ang-1 or VEGF-specific antibody.

Assessment of the cultured vascular cells can include assessment of vitality. The term "vitality" of vascular cells in culture is commonly directed to determining whether cells are alive or dead, and, for a population of cells, providing a good estimate of the proportion of live cells in the specific population being studied. Methods for such measurement suitable for use with the vascular cells of the present invention include, but are not limited to metabolic viability and dye exclusion viability assays. Dye exclusion assays are based on the ability of the cell membrane to exclude a particular stain ("vital stain"). A non-limiting list of suitable dye exclusion assays includes trypan blue staining, propidium iodide staining, 7-aminoactinomycin-D ("7-AAD") and acridine orange. Metabolic assays include, but are not limited to tetrazolium reduction, resazurin reduction, protease markers, and ATP detection.

According to some embodiments of the present invention, the human smooth muscle cells are transduced with a retroviral nucleic acid construct or lentivirus nucleic acid construct comprising a polynucleotide sequence encoding a vascular endothelial growth factor 165 (VEGF$_{165}$) polypeptide. Suitable VEGF$_{165}$ polypeptides include, but are not limited to GenBank Accession numbers BAG70136.1, AAM03108.1, BAA78418.1 and BAG70265.1. According to other embodiments of the present invention, the human endothelial cells are transduced with a retroviral nucleic acid construct or lentivirus nucleic acid construct comprising a polynucleotide sequence encoding an angiopoietin-1 (Ang-1) polypeptide. Suitable Ang-1 polypeptides include, but are not limited to GenBank Accession numbers AAM92271.1 and NP-00130980. As used herein, the term "retroviral nucleic acid construct or lentivirus nucleic acid construct" refers to a nucleic acid expression construct. To express exogenous polypeptides in the mammalian cells, a polynucleotide sequence encoding a VEGF-A family growth factor VEGF$_{165}$ (for example, GenBank Accession number AF486837, GenBank Accession number AB021221, GenBank Accession number FLJ08203AAAN) or an Ang-1 polypeptide (for example, GenBank Accession number AY124380.1, BC152419.1, AB084454.1) is ligated into a nucleic acid construct suitable for mammalian cell expression. Such a nucleic acid construct includes a promoter sequence for directing transcription of the polynucleotide sequence in the cell in a constitutive or inducible manner.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vector may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. In some embodiments, the signal sequence for this purpose is a mammalian signal sequence or a signal sequence specific to the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated. Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long terminal repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

The promoter and enhancer elements utilized by the nucleic acid construct of some embodiments of the invention are active in the specific cell population transformed, e.g. SC and/or EC cells. Examples of suitable promoters/enhancers which can be utilized by the nucleic acid construct of the present invention include the endothelial-specific promoters: see US Patent Publication 2014/0155467 to Harats et al, the preproendothelin-1, PPE-1 promoter (Harats D, J Clin Invest. 1995 March; 95(3):1335-44), the PPE-1-3x promoter [PCT/IL01/01059; Varda-Bloom N, Gene Ther 2001 June; 8(11):819-27], the TIE-1 (S79347, S79346) and the TIE-2 (U53603) promoters [Sato T N, Proc Natl Acad Sci USA 1993 Oct. 15; 90(20):9355-8], the Endoglin promoter [Y11653; Rius C, Blood 1998 Dec. 15; 92(12):4677-90], the von Willebrand factor [AF152417; Collins C J Proc Natl Acad Sci USA 1987 July; 84(13):4393-7], the KDR/flk-1 promoter [X89777, X89776; Ronicke V, Circ Res 1996 August; 79(2):277-85], The FLT-1 promoter [D64016 AJ224863; Morishita K: J Biol Chem 1995 Nov. 17; 270 (46):27948-53], the Egr-1 promoter [AJ245926; Sukhatme V P, Oncogene Res 1987 September-October; 1(4):343-55], the E-selectin promoter [Y12462; Collins T J Biol Chem 1991 Feb. 5; 266(4):2466-73], The endothelial adhesion molecules promoters: ICAM-1 [X84737; Horley K J EMBO J 1989 October; 8(10):2889-96], VCAM-1 [M92431; Iademarco M F, J Biol Chem 1992 Aug. 15; 267(23):16323-9], PECAM-1 [AJ313330 X96849; CD31, Newman P J, Science 1990 Mar. 9; 247(4947):1219-22], the vascular smooth-muscle-specific elements: CArG box X53154 and aortic carboxypeptidase-like protein (ACLP) promoter [AF332596; Layne M D, Circ Res. 2002; 90: 728-736] and Aortic Preferentially Expressed Gene-1 [Yen-Hsu Chen J. Biol. Chem., Vol. 276, Issue 50, 47658-47663, Dec. 14, 2001], a synthetic promoter containing the aortic preferentially expressed gene-1 (APEG-1) E box motif (Hsieh et al., J Biol Chem 274(20):14344-14351 (1999), which is hereby incorporated by reference in its entirety) can be utilized. Also, a promoter specific for microvascular endothelial cells can be used, such as the promoter of calcitonin receptor-like receptor (CRLR) (Nikitenko et al., FASEB J. 17(11):1499-501 (2003), which is hereby incorporated by reference in its entirety). Other suitable vascular specific promoters are well known in the art, such as, for example, the EPCR promoter (U.S. Pat. No. 6,200,751 to Gu et al) and the VEGF promoter (U.S. Pat. No. 5,916,763 to Williams et al).

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide coding sequence(s) can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Suitable vectors include viral expression vectors such as retrovirus, lentivirus, or herpes virus. In some specific embodiments the nucleic acid construct is a retroviral nucleic acid construct or lentivirus nucleic acid construct. As used herein, the term "retroviral nucleic acid expression construct" refers to a nucleic acid construct for expression of the polynucleotide sequence comprising portions of the retroviral genome providing viral packaging, cell attachment and coding sequence transcription, and, optionally, other retroviral regulatory elements. The vector system is used to infect autologous or exogenous vascular cells with the nucleic acid constructs that, in turn, express the angiogenic proliferating and maturation factors.

A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence.

Retroviral vectors which have been modified to form suitable nucleic acid constructs for delivering a recombinant gene encoding a VEGF$_{165}$ or Ang-1 polypeptide into SC or EC cells are disclosed in U.S. Pat. No. 7,524,493 to Flugelman et al, which is hereby incorporated by reference in its entirety.

In specific embodiments, the retroviral vector comprising a polynucleotide sequence encoding a VEGF 165 polypeptide is as set forth in SEQ ID NO: 1.

In other specific embodiments, the retroviral vector comprising a polynucleotide encoding an angiogenin-1 polypeptide is as set forth in SEQ ID NO: 2.

Illustrative retroviruses include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), Spumavirus, Friend murine leukemia virus, Murine Stem Cell Virus (MSCV) and Rous Sarcoma Virus (RSV)) and lentivirus. As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred. Retroviral vectors and more particularly lentiviral vectors may be used in practicing the present invention. Accordingly, the term "retrovirus" or "retroviral vector," as used herein is meant to include "lentivirus" and "lentiviral vectors" respectively. Additional lentivirus vectors also include those described in U.S. Pat. No. 6,790,657 to Arya, U.S. Patent Application Publication No. 2004/0170962 to Kafri et al., and U.S. Patent Application Publication No. 2004/0147026 to Arya, which are hereby incorporated by reference in their entirety. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

The present invention envisions preparing vascular cells for transduction and/or transducing the cells with retroviral nucleic acid construct or lentivirus nucleic acid constructs. In-vitro, cells commonly suffer from prolonged recovery and impaired viability following transduction, negatively affecting efficiency and efficacy of therapeutic methods employing the transduced cells. Vascular cells provided according to the methods of the present invention afford an effective way to enhance the therapeutic potential of the cells following transduction. Alternatively or additionally, vascular cell transduction according to the methods of the present invention provides an effective way to enhance the therapeutic potential of the transduced cells.

The delivery of a gene(s) or other polynucleotide sequences using a retroviral or lentiviral vector by means of viral infection rather than by transfection is referred to as transduction. In one embodiment, retroviral vectors are transduced into a cell through infection and provirus integration. In certain embodiments, a cell, e.g., a target cell, is "transduced" if it comprises a gene or other polynucleotide sequence delivered to the cell by infection using a viral or retroviral vector. In particular embodiments, a transduced cell comprises one or more genes or other polynucleotide sequences delivered by a retroviral or lentiviral vector in its cellular genome.

Retroviruses may be used to infect cells ex vivo, or in vitro using techniques well known in the art. For example, when cells, for instance smooth muscle cells or endothelial cells are transduced ex vivo or in vitro, the retroviral vector particles may be incubated with the cells using a dose generally in the order of between 1 to 50 multiplicities of infection (MOI) which also corresponds to $1\times10^5$ to $50\times10^5$ transducing units of the viral vector per $1\times10^5$ cells. This, of course, includes amount of vector corresponding to 1, 2, 3, 4, 5, 6, 7, 8, 9, 10, 15, 20, 25, 30, 35, 40, 45, and 50 MOL.

Virus concentration may also be expressed and provided according to viral titer (TU/mL), which can be measured, for example, by using a commercially available coat protein titer assay, which is an ELISA against a viral coat protein. The following formula can be used to calculate the pg/mL of coat protein: there are approximately n molecules of coat protein per physical particle (PP) of lentivirus: (n)×(mol mass of coat protein per PP)=Y, Y/Avogadro=(Y)/($6\times10^{23}$) =Z g of coat protein per PP, or 1/Z PP per gram coat protein. A reasonably well packaged, VSV-G pseudotyped lentiviral vector will have an infectivity index in the range of 1 TU per 1000 physical particles (PP) to 1 TU per 100 PP (or less), which can be converted to TU/mass of coat protein.

According to the present invention, transducing human smooth muscle cells with the retroviral nucleic acid construct or lentivirus nucleic acid construct comprises (a) preconditioning the human smooth muscle cells with DEAE Dextran and (b) contacting the human smooth muscle cells with the retroviral nucleic acid construct or lentivirus nucleic acid construct in a transduction medium comprising the construct.

According to some aspects of the present invention, preparing the human vascular endothelial and smooth muscle cells for transduction with the retroviral nucleic acid construct or lentivirus nucleic acid construct comprises, inter alia, preconditioning the human vascular endothelial and smooth muscle cells with DEAE Dextran before contacting the human vascular endothelial and smooth muscle cells with the retroviral nucleic acid construct or lentivirus nucleic acid construct in a transduction medium comprising the construct.

The same teachings can be used for the transduction itself.

According to the present invention, transducing human smooth muscle cells with the retroviral nucleic acid construct or lentivirus nucleic acid construct comprises (a) preconditioning the human smooth muscle cells with DEAE Dextran and (b) contacting the human smooth muscle cells with the retroviral nucleic acid construct or lentivirus nucleic acid construct in a transduction medium comprising the construct.

As used herein, the term "DEAE-Dextran" refers to the cationic polymer diethylaminoethyl-dextran, or O,O'-Bis[2-(N-Succinimidyl-succinylamino)ethyl] polyethylene glycol. DEAE-Dextran is available in range of average molecular weights from 1000 kDa to 500,000 kDa or more. In specific embodiments, the DEAE-Dextran has an average molecular weight of >500,000 kDaltons. DEAE-Dextran complexes with DNA, facilitates adhesion to membranes and promotes entry of DNA into cells. However, exposure to DEAE-Dextran can damage cells and compromise their vitality following transduction. The inventors have identified specific concentrations and durations of preconditioning with DEAE-Dextran effective in enhancing vascular cell transduction without impairing vitality and therapeutic value of the transduced vascular cells.

Thus, in some embodiments, smooth muscle cells are pre-conditioned with DEAE-Dextran concentration in a range between 0.10 mg/ml and 0.9 mg/ml DEAE-Dextran. In some embodiments, preconditioning is performed with a range of DEAE-Dextran between 0.125-0.8 mg/ml DEAE-Dextran, between 0.25-0.75 mg/ml DEAE-Dextran, between 0.30-0.72 mg/ml DEAE-Dextran, between 0.42-0.67 mg/ml DEAE-Dextran, between 0.48-0.62 mg/ml DEAE-Dextran, between 0.125-0.5 mg/ml DEAE-Dextran or between 0.125-0.75 mg/ml DEAE-Dextran. In some embodiments, the preconditioning is performed with 0.125 mg/ml DEAE-Dextran, 0.20 mg/ml DEAE-Dextran, 0.25 mg/ml DEAE-Dextran, 0.40 mg/ml DEAE-Dextran, 0.50 mg/ml DEAE-Dextran or 0.75 mg/ml DEAE-Dextran. In specific embodiments, the preconditioning is performed with 0.125 mg/ml DEAE-Dextran.

The duration of preconditioning is also ultimately a factor in the efficacy of smooth muscle cell transduction with retrovirus constructs. Thus, according to some embodiments, preconditioning of smooth muscle cells with DEAE-Dextran is performed for between 0.5 and 5 minutes. In some embodiments, preconditioning is performed for between 0.5 and 5 minutes, for between 1 and 5 minutes, for between 1 and 4 minutes, for between 1.5 and 3.5 minutes, for between 2 and 3 minutes, for between 1.7 and 3.2 minutes, for between 0.8 and 2 minutes. In some embodiments, the preconditioning is performed for 0.5, 0.75, 1.0, 1.5, 2.0, 2.5, 3.0, 3.5 or 4.0 minutes. In specific embodiments, the preconditioning with DEAE-Dextran is performed for 1 minute. In specific embodiments, the preconditioning with DEAE-Dextran is performed with 0.125 mg/ml DEAE-Dextran for 1 minute.

In some embodiments of the invention, vascular endothelial cells are preconditioned with DEAE-Dextran prior to transduction. Preconditioning of endothelial cells with DEAE-Dextran is performed with DEAE-Dextran concentration in a range between 0.5 mg/ml and 1.5 mg/ml DEAE-Dextran. In some embodiments, preconditioning of EC is performed with a range of DEAE-Dextran between 0.75-1.25 mg/ml DEAE-Dextran or between 0.8-1.2 mg/ml DEAE-Dextran. In some embodiments, preconditioning of EC is performed with 0.5 mg/ml DEAE-Dextran, 0.75 mg/ml DEAE-Dextran, 0.9 mg/ml DEAE-Dextran, 1.0 mg/ml DEAE-Dextran, 1.2 mg/ml DEAE-Dextran or 1.4 mg/ml DEAE-Dextran. In specific embodiments, the preconditioning of EC is performed with 1.0 mg/ml DEAE-Dextran.

According to some embodiments, preconditioning of endothelial cells (EC) with DEAE-Dextran is performed for between 0.5 and 5 minutes. In specific embodiments, preconditioning is performed for between 1 to 3 minutes. In specific embodiments, the preconditioning with DEAE-Dextran is performed for 1 minute. In specific embodiments, the preconditioning of EC with DEAE-Dextran is performed with 1.0 mg/ml DEAE-Dextran for 1 minute.

Preconditioning with DEAE-Dextran can be performed with the DEAE-Dextran provided in any suitable medium for EC cells and SM cells. In specific embodiments, preconditioning of SM cells and EC cells is performed in the transduction medium w/o FBS. In other embodiments, when preconditioning is employed, it is performed in incubation medium (M199+Glutamine w/o Serum).

Following the preconditioning, in preparation for transduction, the vascular cells are washed free of the preconditioning medium and are ready for transduction with the retroviral nucleic acid constructor lentivirus nucleic acid construct. Suitable transduction media for vascular cells include, but are not limited to M199, DMEM and MCB131. According to specific embodiments, vascular cells transduction medium comprises M199 medium. According to further embodiments, vascular cell transduction medium comprises Glutamine. In some embodiments, the transduction medium comprises Glutamine in a range between 1 and 10 mM. In some embodiments the transduction medium comprises Glutamine in a range between 1 and 10 mM, 2 and 8.0 mM, 2.5 and 7.5 mM, 3 and 6.5 mM, 4 and 6 mM, or 4-5 mM. In some embodiments the transduction medium comprises 1 mM, 2 mM, 3 mM, 4 mM, 5 mM, 6 mM, 7 mM, 8 mM, 9 mM or 10 mM Glutamine. In specific embodiments, the transduction medium comprises 2 mM Glutamine. In other specific embodiments the vascular cell transduction medium comprises M199 medium and 2 mM Glutamine. In specific embodiments, the transduction medium comprising M199 medium and 2 mM Glutamine is a serum-free medium.

The vascular cells of the invention can be transduced in suitable vessels, including but not limited to tubes, capillaries, cell culture vessels, cell culture plates and the like. The instant inventors have found that the volume of transduction medium during vascular cell transduction can affect transduction efficacy and viability of the transduced vascular cells.

According to some embodiments, transduction comprises contacting human vascular cells (SM or EC) in a transduction medium comprising the retroviral nucleic acid construct or lentivirus nucleic acid construct in a volume of 0.5-2.0 ml transduction medium. In some embodiments, contacting is performed in a volume of 0.5, 0.60, 0.70, 0.80, 1.0, 1.5 or 2.0 ml transduction medium. In a specific embodiment, pre-conditioned human SM cells of the invention are contacted with the retroviral nucleic acid construct or lentivirus nucleic acid construct in a volume of 1 ml transduction medium. In specific embodiments, pre-conditioned human EC cells of the invention can be contacted with the retroviral nucleic acid construct or lentivirus nucleic acid construct in a volume of 0.70 ml transduction medium.

Proper timing of the duration of retroviral transduction of vascular cells can have an important contribution to the efficacy of the transduction (e.g. transduction rate), on the one hand, but also affects the viability and therapeutic usefulness of the transduced cells, on the other. According to some embodiments of the invention, a streamlined transduction process provides good transduction efficiency while maintaining high levels of viability in the transduced vascular cells.

Thus, according to some embodiments, transduction of the vascular cell of the invention comprises contacting human vascular cells (SM or EC) with the retroviral nucleic acid construct or lentivirus nucleic acid construct in a transduction medium comprising the retroviral nucleic acid construct or lentivirus nucleic acid construct for a duration of at least 2.5 and no more than 3.5 contiguous hours. In some embodiments, the duration is in the range of 2.6-3.3 contiguous hours, 2.8-3.2 contiguous hours or 2.9-3.1 contiguous hours. In some embodiments, the duration of contacting is 2.5, 2.75, 3.0, 3.25 or 3.5 contiguous hours, 2.8-3.2 contiguous hours or 2.9-3.1 contiguous hours. In a specific embodiment, the duration of contacting of EC and SM cells is 2.5 contiguous hours.

Efficacy (rate) of transduction can be assessed by measuring phenotypic changes of the transduced vascular cells, such as retroviral markers or recombinant proteins encoded by the constructs, as detailed hereinabove. In some embodiments the rate of transduction is assessed both for intracellular recombinant protein (e.g. Ang-1 in transduced EC cells) in the transduced cells by immunohistochemistry, as well as for secreted protein levels, which can be assayed by ELISA of the cell medium during culture of the cells following transduction. According to the present invention, shorter transduction times (e.g. 2.5 contiguous hours) have been found to be equally effective as longer (e.g. 4 hours) duration, when measuring both levels of intracellular recombinant protein and secreted recombinant protein.

According to the present invention, vascular cells (SM or EC cells) can be cultured in a growth medium following transduction, typically in the presence of a selection agent, e.g. G418, neomycin or the like, depending on the selectable marker borne on the retroviral nucleic acid construct or lentivirus nucleic acid construct used for transduction, for at least a duration of culturing sufficient to allow effective selection of cells resistant to the negative effects of the selection agent. Some suitable medium for culturing vascular cell are detailed hereinabove. In some embodiments, the human smooth muscle cells are cultured in growth medium comprising Smooth Muscle Growth Medium (SmGm)-2 Bullet Kit Medium™ (Clonetics™, Lonza, Basel) following transduction. In brief, Smooth Muscle Growth Medium (SmGm)-2 Bullet Kit Medium™ comprises basal smooth muscle growth medium plus supplements and growth factors (e.g. hEGF, insulin, hFGF-B, fetal bovine serum FBS, gentamicin/amphotericin B). In some embodiments, the growth medium further comprises fetal bovine serum (FBS). In some embodiments the growth medium comprises FBS in a range between 5 and 25%, 10 and 20% and 10-15%. In some embodiments the growth medium comprises 5%, 8%, 10%, 12%, 15%, 18%, 20%, 22% or 25% FBS. In specific embodiments transduced smooth muscle cells are cultured in growth medium comprising the growth medium and 15% FBS following transduction. In other specific embodiments smooth muscle cells are cultured in growth medium comprising Smooth Muscle Growth Medium (SmGm)-2 Bullet Kit Medium™ and 15% FBS following transduction.

In some embodiments, the human EC cells are cultured in growth medium comprising Endothelial Cell Growth Medium (EGM)-2 Bullet Kit Medium™ (Clonetics™, Lonza, Basel) following transduction. In brief, Endothelial Growth Medium (EGM)-2 Bullet Kit Medium™ comprises basal endothelial growth medium plus supplements and growth factors (e.g. hEGF, hydrocortisone, VEGF, hFGF-B, R3-IGF-1, heparin, fetal bovine serum FBS, gentamicin/ amphotericin B). In other embodiments, endothelial growth medium is devoid or at least one, at least two, or all of the recited growth factors. In some embodiments, the growth medium further comprises fetal bovine serum (FBS). In some embodiments the growth medium comprises FBS in a range between 5 and 25%, 10 and 20% and 10-15%. In some embodiments the growth medium comprises 5%, 8%, 10%, 12%, 15%, 18%, 20%, 22% or 25% FBS. In specific embodiments transduced EC cells are cultured in growth medium comprising the growth medium and 10% FBS following transduction. In other specific embodiments EC cells are cultured in growth medium comprising Endothelial Growth Medium (EGM)-2 Bullet Kit Medium™ and 10% FBS following transduction.

II. Methods of Cell Transduction

The instant inventors have uncovered methods enabling effective retroviral transduction of vascular cells (e.g. SM and EC cells) with constructs encoding pro-angiogenic factors, producing highly viable, proliferating vascular cells expressing the pro-angiogenic factors which can be prepared for use, inter alia, in transplantation for inducing neovascularization to treat vascular diseases.

Thus, according to one aspect, the present invention relates to methods for transducing smooth muscle (SM) cells with a retroviral nucleic acid construct or lentivirus nucleic acid construct comprising a polynucleotide sequence encoding a $VEGF_{165}$ polypeptide, the method comprising (a) preconditioning the human SM cells with between 0.125 and 0.9 mg/ml DEAE-Dextran, and (b) contacting the SM cells with the retroviral nucleic acid construct or lentivirus nucleic acid construct in a transduction medium comprising the nucleic acid construct.

According to some embodiments, the retroviral nucleic acid construct or lentivirus nucleic acid construct comprises the nucleic acid sequence of SEQ ID NO: 1.

According to some embodiments, the preconditioning is performed with 0.125 mg/ml-0.5 mg/ml DEAE-Dextran.

According to some embodiments, the preconditioning is performed with 0.125 mg/ml DEAE-Dextran.

According to some embodiments, the preconditioning is performed for between 1 and 4 minutes.

According to some embodiments, the preconditioning is performed for between 2 and 3 minutes.

According to some embodiments, the preconditioning is performed for 1 minute.

According to some embodiments, the human smooth muscle cells are freshly isolated smooth muscle cells from venous tissue.

According to some embodiments, the human smooth muscle cells are isolated in an isolation medium comprising Smooth muscle Growth Medium (SmGM)-2 Bullet Kit medium and 20% Fetal Bovine Serum.

According to some embodiments, the human smooth muscle cells are cryopreserved and thawed smooth muscle cells from venous tissue.

According to some embodiments, the human smooth muscle cells are cultured prior to transduction.

According to some embodiments, the contacting of step (b) is performed in a volume of 1 ml transduction medium.

According to some embodiments, the human smooth muscle cells are cultured in medium comprising Smooth muscle Growth Medium (SmGM)-2 Bullet Kit medium prior to and following said transduction.

According to some embodiments, the growth medium further comprises 5-25% fetal bovine serum (FBS).

According to some embodiments, the growth medium further comprises 10-20% fetal bovine serum (FBS).

According to some embodiments, the growth medium further comprises 15% fetal bovine serum (FBS).

According to another aspect, the present invention relates to methods for transducing endothelial cells (EC) with a retroviral nucleic acid construct or lentivirus nucleic acid construct comprising a polynucleotide sequence encoding an Angiopoietin-1 (Ang-1) polypeptide, the method comprising (a) preconditioning the human EC cells with 1.0 mg/ml DEAE-Dextran, and (b) contacting the endothelial cells in a transduction medium comprising the nucleic acid construct for a duration of at least 2.5 and no more than 3.5 contiguous hours.

According to some embodiments, the nucleic acid construct comprises the nucleic acid sequence of SEQ ID NO: 2.

According to some embodiments, the duration is 2.8-3.2 contiguous hours.

According to some embodiments, the duration is 2.5-3.0 contiguous hours.

According to some embodiments, the duration is 2.5 contiguous hours.

According to some embodiments, the said human endothelial cells are freshly isolated endothelial cells from venous tissue.

According to some embodiments, the human endothelial cells are isolated in an isolation medium comprising Endothelial Growth Medium (EGM)™-2 Bullet Kit medium and 10% Fetal Bovine Serum.

According to some embodiments, the human endothelial cells are cryopreserved and thawed endothelial cells from venous tissue.

According to some embodiments, the human endothelial cells are cultured prior to transduction.

According to some embodiments, the human endothelial cells are cultured in growth medium comprising Endothelial Growth Medium (EGM)™-2 Bullet Kit medium prior to and following said transduction.

According to some embodiments, the growth medium further comprises 5-25% fetal bovine serum (FBS).

According to some embodiments, the growth medium further comprises 10-20% fetal bovine serum (FBS).

According to some embodiments, the growth medium further comprises 10% fetal bovine serum (FBS).

According to some embodiments, the transduction medium comprises M199 medium.

According to some embodiments, the transduction medium further comprises 1-10 mM Glutamine.

According to some embodiments, the transduction medium further comprises 2-8 mM Glutamine.

According to some embodiments, the transduction medium further comprises 2 mM Glutamine.

According to some embodiments, the transduction medium is a serum-free medium.

Vascular cells (SM and EC) suitable for use with the methods of the present invention include vascular cells freshly isolated from vascular tissue as well as preserved vascular cells and cultured vascular cells. Methods for smooth muscle cell isolation from vascular tissue are well known in the art.

Details on the teachings of transduction according to the transduction aspects are provided hereinabove in section (I).

III. Methods for Hypothermal Preservation of Transduced Cells

The present invention relates in some embodiments thereof to methods and compositions for effective preservation of retroviral transduced vascular tissue cells (e.g endothelial cells-EC and/or smooth muscle cells-SM). Transduced vascular tissue cells, expressing pro-angiogenic factors such as VEGF and Ang-1, can be prepared for hypothermal preservation in manner prolonging the effective shelf life of the transduced cells, increasing the utility of their use in pro-angiogenic therapy.

The instant inventors have uncovered that retrovirally transduced vascular cells (e.g. SM and EC cells) differ characteristically in their response to incubation, at lowered temperatures, in different preservation solutions, affecting their viability as well as proliferative capability and transgene expression, ultimately affecting their suitability for transplantation for treating vascular diseases.

Careful monitoring of the fate of retrovirally transduced smooth muscle and endothelial cells following incubation at between 2° C. and 8° C. for up to 48 hours in either an intracellular-type hypothermal preservation solution comprising lactobionate, sucrose, dextran, glucose, mannitol, HEPES buffer and energy substrates, or an isotonic-type hypothermal preservation solution comprising an isotonic multiple electrolytes solution supplemented with dextrose, heparin and albumin indicated that the transduced smooth muscle cell proliferation (see FIG. 21B), cell viability (see FIG. 22B), cell condition in culture (see FIGS. 23C, 23D and 24C and 24D) and transgene expression (see Tables 10 and 11) were superior in smooth muscle cells incubated in the cold with the intracellular-type hypothermic preservation solution comprising lactobionate, sucrose, dextran, glucose, mannitol, HEPES buffer and energy substrates, while the transduced smooth muscle cell proliferation (see FIG. 21A), cell viability (see FIG. 22A), cell condition in culture (see FIGS. 23A, 23B and 24A and 24B) and transgene expression (see Tables 10 and 11) were superior in the isotonic-type hypothermal preservation solution comprising an isotonic multiple electrolytes solution supplemented with dextrose, heparin and albumin (see Example 4 hereinbelow).

Thus, according to one aspect, the present invention relates to methods for hypothermal preservation of human smooth muscle cells transduced with a retroviral nucleic acid construct or lentivirus nucleic acid construct comprising a polynucleotide sequence encoding a $VEGF_{165}$ polypeptide, the method comprising incubating the transduced human smooth muscle cells in an intracellular-type hypothermal preservation solution comprising lactobionate, sucrose, dextran, glucose, mannitol, HEPES buffer and energy substrates at between 2° C. and 8° C.

According to another aspect, the present invention relates to methods for hypothermal preservation of human endothelial cells transduced with a retroviral nucleic acid construct or lentivirus nucleic acid construct comprising a polynucleotide sequence encoding a Angiopoietin-1 (Ang-1) polypeptide, the method comprising incubating the transduced human endothelial cells in an isotonic-type hypothermal preservation solution comprising an isotonic multiple electrolytes solution supplemented with dextrose, heparin and albumin at between 2° C. and 8° C.

As used herein, the term "hypothermal" is defined as relating to mean temperatures below room temperature. For example, "hypothermal" temperatures include, but are not limited to, temperatures between about 0° C. to about 15° C., temperatures between about 2° C. to about 8° C., temperatures between about 3° C. to about 5° C., and the like. In specific embodiments, "hypothermal" relates to temperatures between 4° C. and 8° C. In other embodiments, "hypothermal" relates to temperatures of 4° C. It will be noted that the terms "hypothermal" and "hypothermic" are used herein interchangeably.

Apparatus for cooling cells and other biological material down to hypothermal temperatures are well known in the art. Cooling blocks, refrigerators, ice baths, chemical cooling (endothermic reactions), Peltier effect coolers and the like abound, in numerous configurations. Accurate regulation of temperature is critical, though, for protection of the cells (or other samples) from the undesirable consequences of freezing, and freezing and thawing, on the one hand, and cytotoxic responses to warming in culture on the other. Fluctuation of no more than 2-3 degrees during the hypothermal preservation of the transduced vascular cells is desirable, and temperature regulation within an even narrower range is more desirable.

Transduced vascular cells for hypothermal preservation, in a specific embodiment, are destined for administration, by injection, to a patient in need thereof, such as a patient suffering from peripheral vascular disease, ischemia or a vascular complication of diabetes. Thus, it will be appreciated that the hypothermal preservation solutions must comprise components which are suitable for injection into a patient.

According to one aspect of the invention, human smooth muscle cells transduced with a retroviral nucleic acid construct or lentivirus nucleic acid construct comprising a polynucleotide sequence encoding a $VEGF_{165}$ polypeptide are hypothermally preserved by incubation in an intracellular-type hypothermic preservation solution comprising lactobionate, sucrose, dextran, glucose, mannitol, HEPES buffer and energy substrates.

As used herein, the term "intracellular-type" hypothermic preservation solution refers to a preservation solution which is designed to balance the altered cellular ionic concentrations that result from incubation of cells at hypothermic temperatures and under nutrient-deprived conditions. In some embodiments, such "intracellular-type" hypothermic preservation solutions comprise, in addition to electrolytes (mostly monovalent cations) required to maintain ionic balance, components designed to counteract irregular sodium and chlorine ion concentrations resulting from decreased sodium pump activity, to counteract cell swelling from increased intracellular osmotic pressure from water influx, to counteract intracellular colloid-osmotic pressure, to remedy the energy deficit expected during hypothermic preservation, to provide pH stability and to provide substrates for ATP synthesis for increased metabolic demands on the cells upon recovery from hypothermic preservation.

In some embodiments, the "intracellular-type" hypothermic preservation solutions comprises lactobionate to replace extra-cellular chloride ions ($Cl^-$); impermeant molecules such as lactobionate, sucrose and mannitol to counteract cell swelling from intracellular osmotic pressure; Dextran-40 to balance colloid-osmotic pressure; low levels of glucose as an energy source; HEPES as a buffer active in cold temperatures and large enough to contribute to osmotic support, and energy substrates (such as adenosine and glutathione). Exemplary "intracellular-type" hypothermic preservation solutions are described in detail by Taylor in U.S. Pat. No. 6,492,103.

In specific embodiments the "intracellular-type" hypothermic preservation solution comprises vitamin E or 6-hydroxy-2,5,7,8-tetramethylchroman-2-carboxylic acid (Trolox), Na ions, calcium ions, K ions and Mg ions. In other specific embodiments, the "intracellular-type" hypothermic preservation solution comprises adenosine and glutathione. In particular embodiments the "intracellular-type" hypothermic preservation solution is HypoThermosol®, or HypoThermosol®-FRS. HypoThermosol®, or HypoThermosol®-FRS (HTS) is available commercially and is manufactured by BioLife Solutions, Inc (Bothell, WA). HTS is suitable for storage at hypothermic temperatures and can be administered directly to a patient in need of vascular cells without requiring further processing or testing.

According to another aspect of the invention human endothelial cells transduced with a retroviral nucleic acid construct or lentivirus nucleic acid construct comprising a polynucleotide sequence encoding an Angiopoietein-1 (Ang-1) polypeptide are hypothermally preserved by incubation in an isotonic-type hypothermic preservation solution comprising an isotonic multiple electrolytes solution supplemented with dextrose, heparin and albumin.

As used herein, the term "isotonic-type" hypothermic preservation solution refers to an injectable preservation solution which is formulated to provide a source of fluids (e.g. water), electrolytes and calories, in order to maintain electrolyte balance for the cells during hypothermic preservation. Added albumin (e.g. human albumin) can act as a radical-scavenging antioxidant, counteracting free radical damage to the preserved cells, regulate colloidal osmotic pressure and stabilize the cells in suspension, function as a ligand binder and transition-metal ion-binder to enhance cell survival, and in general enhancing viability and survival of cells in suspension. Added heparin can function to counteract cell coagulation and enhance angiogenic efficacy of the injected endothelial cells. Both heparin and the added dextrose, due to their molecular mass act as impermeants to counteract cell swelling from intracellular colloid osmotic pressure.

In some embodiments, the isotonic-type hypothermic preservation solution comprises Na ions, K ions, Mg ions, Cl ions, acetate ions and gluconate ions, and is adjusted to pH 7.4-77 with sodium bicarbonate. In other embodiments, the isotonic hypothermic preservation solution comprises Na ions, K ions, Mg ions, acetate ions, gluconate ions, dextrose, heparin and human albumin, and is adjusted to pH 7.4-7.7 with sodium bicarbonate.

In particular embodiments the "isotonic-type" hypothermic preservation solution comprises Plasma-Lyte A® isotonic solution supplemented with 0.1% dextrose, 100 U/ml heparin and 1% human albumin, adjusted to pH 7.4-7.7 with sodium bicarbonate. One liter of Plasma-Lyte A® dissolved in water has an ionic concentration of 140 mEq sodium, 5 mEq potassium, 3 mEq magnesium, 98 mEq chloride, 27 mEq acetate, and 23 mEq gluconate. The osmolarity is 294 mOsmol/L (calc). Normal physiologic osmolarity range is 280 to 310 mOsmol/L. The caloric content is 21 kcal/L. Plasma-Lyte A® (PL) is available commercially and is manufactured by Baxter Heathcare Corp (Deerfield, IL).

PL is suitable for storage at hypothermic temperatures and can be administered directly to a patient in need of vascular cells without requiring further processing or testing.

Cryopreservation solutions often comprise dipolar aprotic solvents (e.g. DMSO) for vitrification during freeze-thaw cycles. However, it is important to stress that such dipolar aprotic solvents are incompatible with injectable preservation solutions. Thus, in specific embodiments of the invention, the hypothermal preservation solution is devoid of dipolar aprotic solvents.

As noted, transduced smooth muscle cells hypothermally preserved in "intracellular-type" hypothermal preservation solution (HTS) exhibited favorable viability, cell proliferation and VEGF$_{165}$ transgene expression following hypothermal preservation, compared to that of transduced smooth muscle cells hypothermally preserved in an "isotonic-type" hypotonic preservation solution. Thus, according to some embodiments of the invention, the transduced smooth muscle cells are characterized by at least one of enhanced viability after hypothermic preservation, enhanced cell proliferation after hypothermic preservation or enhanced transgene expression following hypothermic preservation, as compared to identical transduced smooth muscle cells preserved in an isotonic multiple electrolytes solution supplemented with dextrose, heparin and albumin.

Likewise, transduced endothelial cells hypothermally preserved in "isotonic-type" hypothermal preservation solution (PL) exhibited favorable viability, cell proliferation and Ang-1 transgene expression following hypothermal preservation, compared to that of transduced endothelial cells hypothermally preserved in an "intracellular-type" preservation solution. Thus, according to some embodiments of the invention, transduced endothelial cells are characterized by at least one of enhanced viability after hypothermic preservation, enhanced cell proliferation after hypothermic preservation or enhanced transgene expression following hypothermic preservation, as compared to identical transduced endothelial cells preserved in an "intracellular-type" hypothermic preservation solution comprising lactobionate, sucrose, dextran, glucose, mannitol, HEPES buffer and energy substrates.

Thus embodiments of the invention refer to the following.

According to an aspect of the invention, there is provided a method for hypothermal preservation of human smooth muscle cells transduced with a retroviral nucleic acid construct or lentivirus nucleic acid construct comprising a polynucleotide sequence encoding a VEGF$_{165}$ polypeptide, the method comprising incubating the transduced human smooth muscle cells in an intracellular-type hypothermic preservation solution at between 2° C. and 8° C.

According to some embodiments, the retroviral nucleic acid construct or lentivirus nucleic acid construct comprises the nucleic acid sequence of SEQ ID NO: 1.

According to some embodiments, the intracellular-type hypothermic preservation solution comprising lactobionate, sucrose, dextran, glucose, mannitol, HEPES buffer and energy substrates.

According to some embodiments, the hypothermic preservation solution further comprises Trolox, Na ions, K ions, calcium ions and Mg ions.

According to some embodiments, the energy substrates comprise adenosine and glutathione.

According to some embodiments, the hypothermic preservation solution comprises lactobionate, sucrose, dextran-40, glucose, mannitol, HEPES buffer, Trolox, Na ions, K ions, calcium ions, Mg ions, adenosine and glutathione.

According to some embodiments, the hypothermic preservation solution is HypoThermosol® FRS.

According to some embodiments, the human smooth muscle cells are freshly isolated smooth muscle cells from venous tissue.

According to some embodiments, the transduced human smooth muscle cells are cultured in medium comprising Smooth muscle Growth Medium (SmGM)-2 Bullet Kit medium prior to the hypothermic preservation.

According to some embodiments, the growth medium further comprises 15% fetal bovine serum (FBS).

According to some embodiments, the transduced smooth muscle cells are characterized by at least one of enhanced viability after hypothermic preservation, enhanced cell proliferation after hypothermic preservation or enhanced transgene expression following hypothermic preservation, as compared to identical transduced smooth muscle cells preserved in an isotonic multiple electrolytes solution.

According to an aspect of the invention there is provided a method for hypothermal preservation of human endothelial cells transduced with a retroviral nucleic acid construct or lentivirus nucleic acid construct comprising a polynucleotide sequence encoding a Angiopoietein-1 (Ang-1) polypeptide, the method comprising incubating the transduced human endothelial cells in an isotonic-type hypothermic preservation solution comprising an isotonic multiple electrolytes solution at between 2° C. and 8° C.

According to some embodiments, the isotonic multiple electrolytes solution is supplemented with dextrose, heparin and albumin.

According to some embodiments, the isotonic multiple electrolytes solution comprises Na ions, K ions, Mg ions, acetate ions and gluconate ions.

According to some embodiments, the pH of the isotonic-type hypothermic preservation solution is adjusted to 7.4-7.7 with sodium bicarbonate.

According to some embodiments, the isotonic hypothermic preservation solution comprises Na ions, K ions, Mg ions, acetate ions, gluconate ions, dextrose, heparin.

According to some embodiments, the hypothermic preservation solution comprises Plasma-Lyte A® supplemented with 0.1% dextrose, 100 U/ml heparin and 1% human albumin and is adjusted to pH 7.4-7.7 with sodium bicarbonate.

According to some embodiments, the human endothelial cells are freshly isolated endothelial cells from venous tissue.

According to some embodiments, the transduced human endothelial cells are cultured in medium comprising Endothelial Growth Medium (EGM)™-2 Bullet Kit medium and 10% Fetal Bovine Serum prior to the hypothermic preservation.

According to some embodiments, the transduced endothelial cells are characterized by at least one of enhanced viability after hypothermic preservation, enhanced cell proliferation after hypothermic preservation or enhanced transgene expression following hypothermic preservation, as compared to identical transduced endothelial cells preserved in an intracellular-type hypothermic preservation solution.

According to some embodiments, the incubation is performed for up to 96 hours.

According to some embodiments, the incubation is performed for 12-72 hours.

According to some embodiments, the incubation is performed for 24-48 hours.

According to some embodiments, the incubation is performed between 4° C. and 6° C.

According to some embodiments, the incubation is performed at 4° C.

IV. Hypothermally Preserved Transduced Vascular Cells

The present invention relates to methods and compositions for effective preservation of retroviral transduced vascular tissue cells (e.g endothelial cells-EC and/or smooth muscle cells-SM). Transduced vascular tissue cells, expressing pro-angiogenic factors such as VEGF and Ang-1, can be prepared for hypothermal preservation in manner prolonging the effective shelf life of the transduced cells, increasing the utility of their use in pro-angiogenic therapy.

The instant inventors have uncovered that retrovirally transduced vascular cells (e.g. SM and EC cells) differ characteristically in their response to incubation, at lowered temperatures, in different preservation solutions, affecting their viability as well as proliferative capability and transgene expression, ultimately affecting their suitability for transplantation for treating vascular diseases.

Careful monitoring of the fate of retrovirally transduced smooth muscle and endothelial cells following incubation at between 2° C. and 8° C. for up to 48 hours in either an intracellular-type hypothermal preservation solution comprising lactobionate, sucrose, dextran, glucose, mannitol, HEPES buffer and energy substrates, or an isotonic-type hypothermal preservation solution comprising an isotonic multiple electrolytes solution supplemented with dextrose, heparin and albumin indicated that the transduced smooth muscle cell proliferation (see FIG. 21B), cell viability (see FIG. 22B), cell condition in culture (see FIGS. 23C, 23D and 24C and 24D) and transgene expression (see Tables 10 and 11) were superior in smooth muscle cells incubated in the cold with the intracellular-type hypothermic preservation solution comprising lactobionate, sucrose, dextran, glucose, mannitol, HEPES buffer and energy substrates, while the transduced smooth muscle cell proliferation (see FIG. 21A), cell viability (see FIG. 22A), cell condition in culture (see FIGS. 23A, 23B and 24A and 24B) and transgene expression (see Tables 10 and 11) were superior in the isotonic-type hypothermal preservation solution comprising an isotonic multiple electrolytes solution supplemented with dextrose, heparin and albumin (see Example 4 hereinbelow).

Thus, according to one aspect, the present invention provides an injectable composition comprising human smooth muscle (SM) cells transduced with a retroviral nucleic acid construct or lentivirus nucleic acid construct comprising a polynucleotide sequence encoding a $VEGF_{165}$ polypeptide suspended in an intracellular-type hypothermic preservation solution. In some embodiments, the intracellular-type hypothermic preservation solution comprises lactobionate, sucrose, dextran, glucose, mannitol, HEPES buffer and energy substrates.

According to another aspect, the present invention provides an injectable composition comprising human endothelial cells transduced with a retroviral nucleic acid construct or lentivirus nucleic acid construct comprising a polynucleotide sequence encoding an Angiopoietein-1 (Ang-1) polypeptide, suspended in an isotonic-type hypothermic preservation solution. In some embodiments, the isotonic-type hypothermic preservation solution is supplemented with dextrose, heparin and albumin.

The injectable composition comprising transduced vascular cells for hypothermal preservation, in a specific embodiment, are destined for administration, by injection, to a patient in need thereof, such as a patient suffering from a vascular disease, such as but not limited to peripheral vascular disease, ischemia or a vascular complication of diabetes. Thus, it will be appreciated that the hypothermal preservation solutions must comprise components which are suitable for injection into a patient.

The hypothermally preserved retrovirally transduced human vascular cell composition of the invention can be used for treatment of vascular disease or vascular-related conditions. Common vascular conditions include but are not limited to, acute thrombotic occlusion, aneurysm, aortoiliac and lower occlusive arterial disease, arterial occlusion, arteriosclerosis, atherosclerosis, brachiocephalic and upper extremity occlusive disease, Behcet's Syndrome, carotid artery disease, chronic rejection, vasculopathy associated with diabetes, clogged arteries, degos, dementia, early embolic stroke, headaches, hemorrhoids, heparin overdose, hereditary angioedema, intracoronary thrombus, intimal hyperplasia, ischemia, lymphedema, myoamoya, myocardial infarction, myointimal hyperplasia, peripheral arterial disease (PAD), pseudoxanthoma elasticum, restenosis sclerosis, scleroderma, stenosis thoracic outlet syndrome, thromboangiitis obliterans, thrombosis, varicose veins, vasculitis, and venous and lymphatic disease.

In some embodiments, the hypothermally preserved injectable human vascular cell compositions of the invention can be used for preventing or treating blood vessel failure in transplanted organs. Currently, the largest single unresolved problem in organ transplantation and organ reperfusion is failure of the blood vessels. Administration of the injectable human vascular cell compositions of the invention can extend the period of time that an organ remains viable for transplant after it is removed from a donor, and help prevent deterioration post-operatively to decrease the likelihood of post-operative vascular conditions, including but not limited to, atherosclerosis, restenosis, transplant arteriosclerosis, stenosis, and ischemia.

When used for treating blood vessels of organs for transplant, the hypothermic preservation solutions of the hypothermally preserved transduced human vascular cells can optionally comprise one or more additional agents. Such agents can, for example, reduce post-operative restenosis or atherosclerosis, or reduce cell atrophy after harvesting but before transplant. Examples of additional agents include, but are not limited to hypoxanthine, a glucocorticoid, a nonglucocorticoid lazaroid, tetracycline, pentoxyphyline, penicillin, insulin, dexamethasone, allopurinol, dbcyclic AMP, trehalose, nitroglycerin or any other agents known in the art of preparation for preservation solutions. The perfusate solutions herein may be administered to the vasculature of an organ before harvesting, during transport, or after transplant. Thus the transported perfusate solutions may be applied both in vivo and ex vivo to organs being transplanted.

In other embodiments, the invention herein also contemplates the use of hypothermally preserved injectable human vascular cell compositions for the treatment of chronic rejection, vasculopathy, or other complications associated with type-1 diabetes. Type-1 diabetes often results in vascular complications and/or nerve damage that can affect any organ in the body, including, but not limited to the eyes, kidneys, and heart.

Vascular complications associated with type-1 diabetes include stenosis, angiopathy (including microangiopathy), high blood pressure, heart attacks, strokes, heart failure, hypertension, and kidney damage. Nerve damage, or neuropathy, associated with type-1 diabetes also causes major complications that can affect the entire body. For example, nerves that connect the spinal cord, muscles, skin, blood vessels, and other organs may become damaged due to diabetes. Particularly severe is nerve damage affecting the heart. Other vascular and neurological conditions that affect diabetics include foot problems and foot pain that develops from complications in blood vessels and in the peripheral nervous system. Such complications may result in changes to both bone structure and soft tissue structure in the feet of diabetics. It may also cause foot ulcers that are difficult to cure.

Type 1 diabetes is also the leading cause of new cases of blindness in adults, usually the result of retinopathy. Other eye disorders that affect diabetics and which may result in blindness include cataracts and glaucoma.

Thus, the present invention contemplates the use of hypothermally preserved injectable human vascular cell compositions of the invention for the treatment of vasculopathy and/or other complications associated with type-1 diabetes. Such conditions include, but are not limited to, glaucoma, foot ulcers, angina, myocardial infarction, and post ischemia. The hypothermally preserved injectable human vascular cell compositions of the invention are preferably delivered locally to a site of stenosis or microangiopathy (e.g., in kidney arteries, coronary arteries, foot ulcers, etc.). Delivery may be made by catheter (e.g., a Dispatch™. or Thrulumen™ catheter), microinjection, or other localized delivery system. The compositions are formulated according to the route of administration and may include additional therapeutic agents.

The present invention also contemplates the use of hypothermally preserved injectable human vascular cell compositions of the invention for the treatment and prevention of vascular conditions associated with vein grafting, e.g., graft coronary artery disease and graft peripheral artery disease. The terms "graft," "vessel," "conduit," and "segment" are used interchangeably herein to refer to any full-length or partial segment of a conduit, whether naturally occurring or synthetic that that may be grafted to bypass an obstruction in the vascular system or to increase blood flow to a particular region in the vascular system. Exemplary uses of vein grafting include: coronary artery bypass grafting (CABG), peripheral artery bypass grafting (PABG), and venous-arterial grafting (VAG).

The injectable vascular cell compositions herein are suspended in sterile, physiologically suitable preservation solution.

In some particular embodiments, the hypothermally preserved injectable human vascular cell compositions of the invention herein can also be used to treat peripheral arterial disease (PAD). PAD refers to damage to the peripheral arteries, which is caused by arterial hypertension and/or formation of plaques. Generally, where the arteries are blocked by cholesterol deposits the PAD condition is also known as atherosclerosis, and where the arteries are blocked by mineral deposits, the condition is known as arteriosclerosis.

PAD is a common disorder that occurs when an artery segment, which normally has smooth lining, becomes narrow and rough allowing clots to form on the walls, thus further narrowing the artery. As a result of the arteries narrowing, organs (e.g., brain, heart, legs, kidney) receive inadequate amounts of blood. This can result in cramping of the organs and/or muscles surrounding the organs. PAD is often diagnosed using any one of the following means: medical history and physical examination, ankle-brachial index (ABI), treadmill exercise test, reactive hyperemia test, segmental pressure measurements, PVR waveform analysis, duplex arterial imaging or ultrasound imaging, photoplethysmography, and arteriogram. Once diagnosed, PAD is often treated by life style changes (quit smoking), exercise, drugs (e.g., Clopidogrel, cilostazol, aspirin and cholesterol lowering drugs), or surgery. Surgery can involve endarterectomy, which is the opening of the artery, cleaning it, and suturing it back together. Endarterectomy works best for pelvis (iliac arteries) or groin (femoral arteries) blockage. Other blockages may be bypassed using a bypass surgery. Bypass surgeries to treat PAD include, but are not limited to, aortobifemoral (wherein blood routed from the abdominal aortic artery to both femoral arteries), femoropopliteal (wherein blood routed from the femoral to the popliteal artery), and femorotibial (wherein blood routed from the femoral to a tibial artery).

For smaller arteries, angioplasty or stenting may be more effective. Angioplasty is widely used for treatment coronary and peripheral arterial disease due to blockage. However, in many cases, stenting is preferable to angioplasty. Stents are scaffolds that can be inserted into an artery either prior to, during, or post angioplasty procedure, or as an alternative to an angioplasty procedure. The present invention contemplates the use of a stent for opening of an artery or a vein in conjunction with the administering of hypothermally preserved injectable human vascular cell compositions of the invention to the stent area. In some embodiments, the hypothermally preserved injectable human vascular cell compositions of the invention are administered locally. Local administration can be accomplished by any means known in the art, including preferably, the use of a Dispatch™ catheter, such as the one made by Sci Med, Maple Grove, Minn. The hypothermally preserved injectable human vascular cell compositions of the invention can be administered in vivo and locally prior to, during, or post stenting or angioplasty.

The hypothermally preserved injectable human vascular cell compositions of the invention can be administered independently or in combination with one or more additional agents. Additional agents that may be administered include, but are not limited to, paclitaxel, ascomycin, etc.

The hypothermally preserved injectable human vascular cell compositions of the invention can also be used to treat renal vascular conditions such as malignant nephroangiosclerosis, infarction from occlusion of major renal vessels, scleroderma, atheromatous embolization, renal cortical necrosis, renal vein thrombosis, necrotizing arteritis, and Wegener's granulomatosis.

Thus, the present invention contemplates the use of the hypothermally preserved injectable human vascular cell compositions of the invention to treat or prevent renal vascular conditions. For example, the hypothermally preserved injectable human vascular cell compositions of the invention can be administered in vivo to kidney vasculature.

The present invention also contemplates the use of the compositions herein to treat or prevent pulmonary vascular conditions. Such conditions include, but are not limited to, atelectasis, acidosis, acute bronchitis, acute mountain sickness, acute pulmonary edema, acute pulmonary thrombolism, adult respiratory distress syndrome, bronchial asthma, emphysema, fat embolism in the lung, heparin protamine reactions, hypertension, hypoxia, hyaline membrane disease, inflammation of the lung, Kartaagener's syndrome, Legionnaire's disease, panacinar emphysema, persistent pulmonary hypertension of newborn, post cardiac surgery acute pulmonary pneumonia, prenatal aspiration syndrome, pulmonary arterial hypertension, and chronic obstructive pulmonary disease.

It is also contemplated by the present invention that vascular conditions associated with sexual dysfunction may be treated and/or prevented with the compositions herein. Vascular conditions associated with sexual dysfunction include, but are not limited to, erectile dysfunction, Peyronie's syndrome, priapism, premature ejaculation, female sexual dysfunction, vaginal lubrication, vaginal engorgement, pain during intercourse (e.g., dyspareunia or vulvodynia), preeclampsia, urologenital infections, vulvodynia and estrogen depletion conditions such as menopause, post-menopause, and hot flashes.

Ocular vascular conditions that can be treated and/or prevented with the compositions herein include, but are not limited to, cataract, intraocular pressure, dry eye, diabetic retinopathy, and glaucoma. Glaucoma is an ocular vascular conditions associated with vasoconstriction causing a particular pattern of optic nerve damage. While this pattern of damage usually occurs as a result of increased intraocular pressure, it may also occur with normal or even below-normal ocular pressure.

It is also contemplated that the compositions herein may be used to treat dermal vascular conditions including, but are not limited to, skin aging, necrotizing fascitis, decubitus ulcers, anal fissures, Raynaud's phenomenon, scleroderma, hair loss (e.g., Alopecia Areata, hair loss in patches believed to be an immunologic disorder, Alopecia Totalis, hair loss over the entire scalp, Alopecia Universalis, loss of all hair, all over the body, Anagen Effluvium, sudden loss of growing hairs which is often caused by chemotherapy, Telogen Effluvium, sudden hair loss when large numbers of follicles enter the resting phase which is usually temporary and may be caused by severe stress, medications, etc.), diffused cutaneous systemic sclerosis, frostbites, and wound healing.

In some embodiments, preparation of the transduced SMC and EC cells for formulation into the transduced vascular cell composition of the invention involves washing the cells of the previous medium (typically transduction or growth) (e.g. gentle washing and centrifugation to remove traces of growth medium) with injection solution or hypothermal preservation solution, and suspending the newly transduced cells in the appropriate hypothermal preservation solution, preferable under Good Manufacturing Practice (GMP) conditions.

In some embodiments, following washing and resuspension, the injectable composition, comprising the vascular cell pellet re-suspended in the hypothermal preservation solution can then be transferred for use in a sterile container at 4-8° C. In some embodiments, the injectable composition is formulated in two separate vials (e.g. polypropylene vials), each vial containing a pre-determined number of ECs or SMCs suspended in 5-50, 10-40, 10-20 or 5-15 ml hypothermal preservation solution (depending on the dose group; Table 2). In some embodiments, the transduced vascular cells are suspended in 10-20 ml hypothermal preservation solution.

The number of vascular cells per vial of the injectable composition depends, of course, on the condition or disease to be treated, on the individual state, size and history of the subject, and on additional, individual considerations of management of the particular case. In some embodiments, vials can be prepared containing vascular cells in the range of 0.5 to $100\times10^6$, 1 to $80\times10^6$, 3 to $70\times10^6$, 5 to $65\times10^6$, 5 to $50\times10^6$, 5 to $45\times10^6$, 5 to $40\times10^6$, 5 to $35\times10^6$, 5 to $25\times10^6$, 5 to $15\times10^6$ cells per vial. In some specific embodiments, the hypothermally preserved retrovirally transduced vascular cells are prepared in vials of 5 to $35\times10^6$ cells per vial.

The injectable vascular cell compositions of the invention, having improved stability under hypothermal preservation, can be hypothermally preserved until needed for delivery to the vascular condition, occlusion or disease to be treated. In some embodiments, the injectable vascular cell compositions are hypothermically preserved, before delivery, for a range of 6-96 hours, between 12 and 72 hours, between 12 and 48 hours, between 24-48 or up to 24 hours. In particular embodiments, the injectable transduced vascular cell composition is hypothermally preserved for 24 or 48 hours before administration. In some embodiments, the injectable transduced vascular cell composition of the invention is hypothermally preserved for between 24-48 hours, for example, at 2-4° C. Thus, in some embodiments, the use of the transduced vascular cell compositions follows hypothermal preservation at 6-96, 12-72 or 2-4° C.

The injectable transduced vascular cell compositions or pharmaceutical compositions of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound or combination of compounds to an organism.

Herein the term "active ingredient" refers to the compounds or combinations thereof accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions of the injectable compositions comprising transduced vascular cells for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

Pharmaceutical compositions suitable for use in context of some embodiments of the invention include compositions wherein the active ingredients are contained in an amount effective to achieve the intended purpose. More specifically, a therapeutically effective amount means an amount of active ingredients (hypothermally preserved transduced vascular cells) effective to prevent, alleviate or ameliorate symptoms of a disorder or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

As noted, the injectable transduced vascular cell composition of the invention can be administered to a subject directly to the site of the vascular occlusion, condition or disease, for example, by catheter, such as the Dispatch™. or Thrulumen™ catheter. Following confirmation of the proper location of the catheter, in some embodiments the transduced vascular cell composition of the invention can be delivered at a predetermined rate (e.g. in the range of 0.5-10, 1-10, 2-5 or 2.0 ml per minute. In some embodiments, the transduced vascular cell composition is delivered at a rate of 2.0 ml/min.

Application of compositions and methods of the invention to vascular tissue in need thereof (e.g. ischemia) can result in revascularization or neovascularization within few weeks from application. In some instances, a single application of the transduced vascular cell compositions of the invention can be sufficient to enable recovery in a period of months to years. In other embodiments, recovery can proceed more slowly due to environmental factors (e.g. oxygen supply). Thus, in some cases, some treatments may require sequential (repeated) application of the transduced vascular cell compositions of the invention, and optionally additional factors as well.

It will be appreciated that repeated applications of the transduced vascular cell compositions of the invention may be required, depending on outcome, size of affected vasculature or tissue, need for addition of factors, etc.

Depending on the severity and responsiveness of the condition to be treated, dosing can be of a single or a plurality of administrations, with course of treatment lasting from several days to several weeks or until cure is effected or diminution of the disease state is achieved.

The amount of a transduced vascular cell compositions of the invention to be administered will, of course, be dependent on the subject being treated, the severity of the affliction, the manner of administration, the judgment of the prescribing physician, etc.

Transduced vascular cell compositions of the invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the phrase "treatment regimen" refers to a treatment plan that specifies the type of treatment, dosage, schedule and/or duration of a treatment provided to a subject in need thereof (e.g., a subject diagnosed with a vascular pathology). The selected treatment regimen can be an aggressive one which is expected to result in the best clinical outcome (e.g., complete cure of the pathology) or a more moderate one which may relief symptoms of the pathology yet results in incomplete cure of the pathology. It will be appreciated that in certain cases the more aggressive treatment regimen may be associated with some discomfort to the subject or adverse side effects (e.g., damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skills in the art are capable of adjusting the type of treatment with the dosage, schedule and duration of treatment.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate the invention in a non-limiting fashion.

Example 1: Smooth Muscle and Endothelial Cell Isolation and Culture

An angiogenic composition for transplantation is comprised of modified endothelial (EC) and smooth muscle cells (SMC) isolated from a human-derived vein segment. Cells are isolated from the vein in two steps of enzymatic reaction, the EC isolated first, and the remainder of the vein is used to isolate SMC. The viability of the cells and the number of Smooth Muscle cells isolated during this initial step appear to be bottle-necks in the entire process. New media formulations with multiple growth factors were tested to assess effect on cell isolation efficacy and cell yield, specifically, to shorten production time of the angiogenic composition.

Methods:

Cells

Endothelial (EC) and Smooth Muscle cells (SMC) were isolated from human-derived vein segments stripped from the patient and transferred to the cell processing unit. Cells were isolated from the vein in two steps of enzymatic reaction: EC are isolated first, and the remainder of the vein is used to isolate SMC.

EC and SMC isolation from different human donors (5 donors for EC and 6 donors for SMC) was performed no more than 48 hours after vein stripping. Briefly, EC were isolated by enzymatic digestion and aggressive washing, while SMC were isolated by enzymatic digestion and seeding of the tissue explants.

EC cell cultures were seeded onto fibronectin-coated 6-well tissue plates (passage 0, p0) and cultured in growth medium until formation of large colonies covering ¼ to ½ of the plate surface ("monolayers") and harvested by trypsinization.

SMC cell cultures for SMC isolation were initiated in growth medium under standard conditions until sprouting of smooth muscle cells from the explants into colonies covering ¼ to ½ of the plate surface and harvested by trypsinization.

Following harvesting the isolated EC and the SMC cells were reseeded onto gelatin-coated 6-well tissue culture vessels or 25 $cm^3$ flasks (passage 1, "p1").

Growth Medium

Isolated cells and explants were grown in either standard growth medium or in an enriched medium (Lonza, Ltd., Basel, Switzerland). Standard growth medium for EC (EC-G) was MCDB 131 medium (Thermo-Fisher Scientific, Waltham, MA) supplemented with L-Glutamine, Heparin, basic FGF and 20% fetal bovine serum (FBS). Standard growth medium for SMC (SMC-G) was DMEM medium (Thermo-Fisher Scientific, Waltham, MA) supplemented with L-Glutamine, basic FGF and 20% FBS. Enriched growth medium for EC (EGM) was EGM™-2 BulletKit™ (Cat #CC-3162, Lonza, Ltd, Basel, Switzerland), supplemented with FBS (EGM %). Enriched growth medium for SMC (SMGM) was SmGM-2™ Bulletkit™ (Cat #CC-3182, Lonza, Ltd, Basel, Switzerland), supplemented with FBS (SMGM %).

Culturine

EC and SMC were cultured until passage 1 (p1) or passage 2 (p2). Cells were counted (Coulter counter) during harvests.

For some comparisons of growth medium, EC and SMC were cultured from passage 4, passage 5 or passage 9 after isolation.

Transduction:

Vascular cells intended for transduction were transferred to transduction medium (M199 medium supplemented with 2 mM Glutamine, at 37° C., 5% $CO_2$) and pre-exposed to DEAE-dextran. The cells were then washed 3 times with PBS and incubated with the retroviral vector suspended in up to 1 ml/well of transduction medium for up to 4 hours at 37° C., 5% $CO_2$. The amount and volume of retroviral vector to be used was calculated according to the cell number and multiplicity of infection (MOI) of 8. From 48 hr after transduction the cells were maintained with G418 (0.35 mg/ml) selection for ten days. Each 2-3 days the cells were harvested and counted using a hemacytometer and their viability, cell proliferation rate and/or transduction rate assessed.

Monitoring

EC identity was verified by flow cytometry of CD31$^+$ cells or by immunohistochemistry (IHC). EC purity (for fibroblast contamination) was tested by IHC for a smooth muscle actin (αSMA).

Results:

EC Isolation Medium

Isolated EC monolayers were divided equally into four wells of a 6-well tissue culture plate. Two wells were cultured in EC-G medium and two wells were cultured in EGM medium, supplemented with 10% FBS (EGM 10%). Media were changed every 48-72 hours, until cells were ready for harvest. FIG. 1 shows EC numbers after the first post-isolation cell harvest. As can be seen in FIG. 1, EC cultured in EGM 10% medium proliferated at a significantly greater rate than EC cultured in EC-G medium.

In order to evaluate the influence of the new medium on EC marker expression and purity, cultured and harvested EC were tested for CD31 and αSMA by either immunohisto-chemistry or FACS. The results are summarized in Tables 1 and 2 below.

TABLE 1

| | EC identity of EC grown in EGM 10%. |
| --- | --- |
| Donor | EC Marker (% CD31$^+$) |
| H1081B | Not done |
| H1082 | 97% |
| H1085 | 98% |
| H1086A | 99% |
| H1086B | 99% |

* Acceptance criteria: >85%

TABLE 2

| | EC PURITY | |
| --- | --- | --- |
| Donor | Treatment | Purity (% αSMA) |
| H1081B | EC-Q | 14.4% |
| | EGM 10% | 6.9% |
| H1082 | EC-G | 8.5% |
| | EGM 10% | 5.1% |
| H1085 | EC-G | 4.4% |
| | EGM 10% | 0.7% |
| H1086A | EC-G | 0.0% |
| | EGM 10% | 0.0% |
| H1086B | EC-G | 0.5% |
| | EGM 10% | 0.6% |

* Acceptance criteria: <15%

As can be seen in Table 1, all of the cultured cells tested had a very high percentage of CD31$^+$ expression, indicating that culturing the EC with EGM 10% does not decrease the efficiency of EC isolation. Table 2 further shows that cul-turing with EGM 10% actually confers an advantage, low-ering the percentage of fibroblasts in the EC population, as compared to that of ECs isolated using EC-G medium.

SMC Isolation Medium

Following EC isolation, vein segments were digested with collagenase, cut into 1-2 mm explants and placed onto 6-well tissue culture plates. Two wells were cultured in SMC-G medium and two wells were cultured in SMGM medium, supplemented with 20% FBS (SMGM 20%).

Growth medium was changed every 48-72 hours, until the cells were ready for harvest. As can be seen in FIG. 2, when measured after the first post-isolation cell harvest (passage 1, p1), SMC cultured in SMGM 20% medium sprouted from the explants and proliferated at a significantly greater rate than SMC cultured in SMC-G medium.

In order to further evaluate the influence of the new medium on SMC growth, a comparison was conducted between SMC isolation in SMGM supplemented with 15% FBS and SMGM supplemented with 20% FBS. As is evident from FIG. 3, culture of SMC in SMGM 20% is clearly advantageous to the SMC isolation procedure.

EC Growth Medium

Following isolation in isolation medium, the vascular cells are cultured in a medium designed for growth and proliferation of cells, as well as maintaining their vitality and robustness, in preparation for retroviral transduction.

Proliferation rate of low passage (passage 4) human EC cells grown in EGM+FBS was consistently superior to that of the same cells cultured in standard medium (EC-G, MCB131 supplemented with FBS 20%, penicillin, strepto-mycin, Glutamine, Amphotericin B and Heparin). Average growth rate for EC cells from three donors, expressed as cell divisions per day, over a 7 day period (with harvest and reseeding at day 4) was significantly accelerated by culture in EGM with 20% FBS (see FIG. 4).

Comparison of EC growth rate with EGM comprising different amounts of FBS supplementation indicated that even though the FBS content of standard medium (EC-G) is high (20%), EGM supplemented with anywhere from 5% to 20% FBS facilitated EC cell proliferation significantly better than the EC-G medium (data not shown). Best results were obtained with EGM and higher FBS supplementation.

In order to establish whether the difference in growth rate (proliferation rate) observed in relatively low passage EC cells (passage 4) is also characteristic for older cells, having characteristically slower growth rates and poorer cell health than the earlier passage cells, passage 9 EC cells were subjected to the same proliferation test with EGM supple-mented with FBS. Evaluation of the average proliferation rates over a 6 day period (with harvest and reseeding at day 4) revealed that the higher passage EC cell proliferation was accelerated by culture in EGM with FBS in the same manner as observed for the passage 4 cells (data not shown).

Since significant improvement in EC proliferation rate was achieved with EGM supplemented with 10-20% FBS, EGM with 10% FBS was selected for EC growth.

SMC Growth Medium

Proliferation rate of low passage (passage 4) human SMC cells grown in SMGM+FBS was consistently superior to that of the same cells cultured in standard medium (SMC-G, DMEM supplemented with FBS 5%, penicillin, streptomy-cin, Glutamine, Amphotericin B and Heparin) or 231G (Gibco base medium supplemented with FBS 5%, rhbFGF, rhEGF and insulin). Average growth rate for SMC cells from three donors, expressed as cell divisions per day, over a 7 day period (with harvest and reseeding at day 4) was significantly accelerated by culture in SMGM with 20% FBS (see FIG. 5). Since significant improvement in SMC proliferation rate was achieved with SMGM supplemented with 15-20% FBS (results not shown), SMGM with 15% FBS was selected for SMC growth.

Growth Medium Potency

Tests of the potency of EGM+FBS and SMCM+FBS for facilitating proliferation after month long storage indicated that their proliferation-promoting effects with vascular cell culture were preserved over the lengthy storage period (results not shown).

Effect of Growth Medium on Proliferation and Transduction

In order to insure the greatest viability of the vascular cells during and following transduction, the ability of media components to facilitate vascular cell transduction and subsequent proliferation was assessed.

SMC medium and transduction: Initial assessment was performed using SMC cells transduced with the TGA-LacZ retrovirus vector. FIG. 6 shows the average growth rates, in divisions per day, for SMC from two donors seeded for a proliferation assay immediately following the retroviral transduction, cultured for four days in various medium, harvested and counted, and then half of the harvested cells re-seeded and grown for four more days, harvested and counted. Average growth rates of the SMCs grown in SMGM 20% FBS in the 8 days following transduction excelled over those of cells grown in either 231G medium with 20% FBS or SMC-G.

The transduction rate of SMCs transduced with TGA-LacZ and grown in different media was also assessed. X-Gal staining of human SMC cells transduced with TGA-LacZ and cultured for three days revealed a significant advantage in transduction rate of cells grown in SMGM 20% FBS over 231G with 20% FBS and SMC-G media (see FIG. 7).

When assessing the SMC medium's effect on growth rate of SMCs transduced with retroviral VEGF vector, the effect on the growth rate of the transduced cells was monitored at step 3 (3-4 days following transduction, when the cell's condition is usually poor) and step 3 b (end of G418 selection, when cells are typically recovering). FIGS. 8A-8B show the average daily growth rate of cells from 3 donors four days after transduction (step 3, FIG. 8A), and after G418 selection (step 3b, FIG. 8B), indicating a clear advantage of SMGM 20% and 15% FBS over SMC-G medium for growth rate following SMC transduction.

EC medium and transduction: In an effort to streamline the EC transduction procedure, the effect of adding growth factors to vascular cell transduction medium was assessed, using the TGA-LacZ retrovirus system. When EC were transduced in serum-free medium with or without added growth factors (hydrocortisone, hEGF, VEGF, hFGF-B, R3-IGF-1, ascorbic acid and heparin), X-Gal staining two days later revealed that adding the growth factors did not provide any significant advantage in transduction rates with the TGA-LacZ vector (FIG. 9). Growth rate of the transduced EC cells, four days post-transduction, likewise remained substantially unchanged by the presence or absence of the growth factors (FIG. 10). Thus, addition of supplements to the transduction medium was deemed optional.

Further investigation of conditions for effective growth following EC cell transduction revealed that for both naïve (untransduced) and TGA-LacZ-transduced EC cells, EGM medium with added 10% FBS provides superior cell proliferation following transduction (FIG. 11) as well as significantly improved LacZ expression (transduction rate) of the transduced cells (FIG. 12).

When assessing the EC medium's effect on growth rate of ECs transduced with retroviral Ang-1 vector, the effect on the growth rate of the transduced cells in the presence of a selection agent (neomycin) was monitored at early passages (step 2 and 3, passages 3 and 4), passage 5 and step 3b (passage 6, end of neomycin selection). FIG. 13 shows the average daily growth rate of cells from 3 donors four days after transduction (step 3, FIG. 13), during (step 3, passage 5) and after neomycin selection (step 3b, FIG. 13), indicating a clear advantage of EGM 10% FBS over EC-G medium for growth rate following EC transduction.

When assessing the effect of EC medium on EC transduction rates with retroviral Ang-1 vector, the effect was monitored by evaluating both Ang-1 expression (immunohistochemistry) and Ang-1 secretion (ELISA) in the transduced EC cells. While cells grown with EGM 10% FBS appeared were in good condition microscopically, cells grown in EC-G were in poor condition when seeded onto IHC slides, either in low or high passage. This difference was also borne out when assessing transduction rates by immunohistochemistry (IHC)-detection of Ang-1 expression (FIGS. 14A and 14B) reveals significantly lower transduction in EC cells grown in EC-G medium (in the case of donors H1069A and H1070B much lower) than that of EC cells grown with EGM 10% FBS. Despite the fact that, in some cases cell growth rate following 10 days G418 selection (step 3b, FIG. 14B) was similar for the EGM 10% and EC-G media, cell condition, when viewed on IHC slides was quite different. In fact, cells grown in EC-G were in such poor condition that they showed a completely different staining pattern than the healthy-looking EGM 10% FBS treated cells.

Figure 14A:
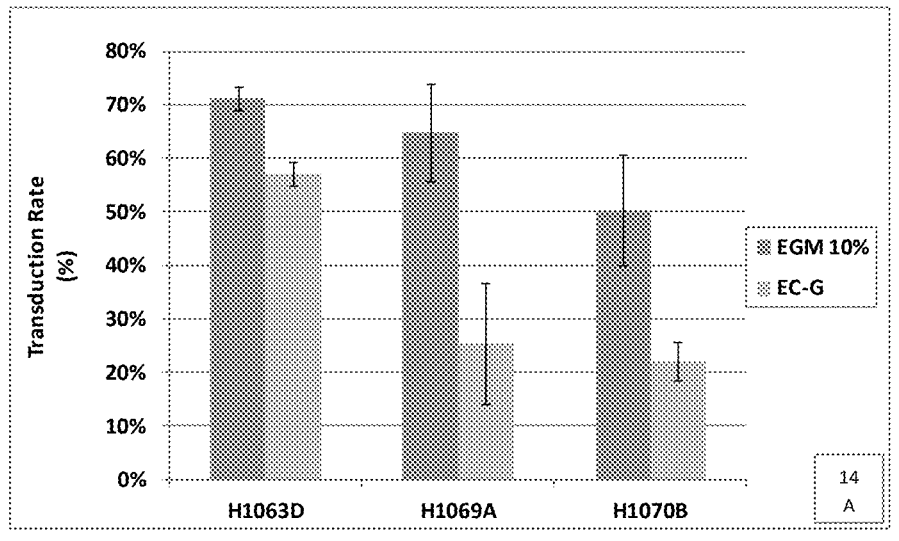
Figure 14B:
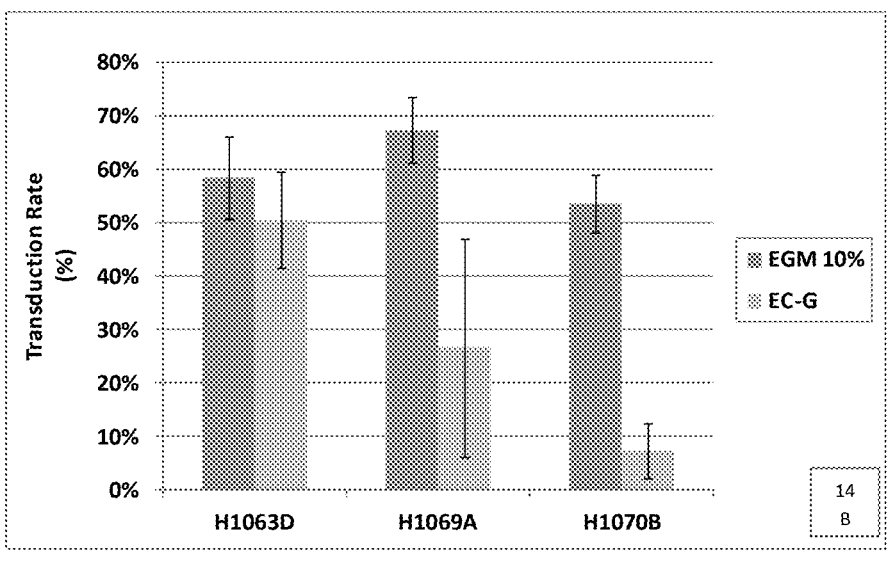
Figure 14C:
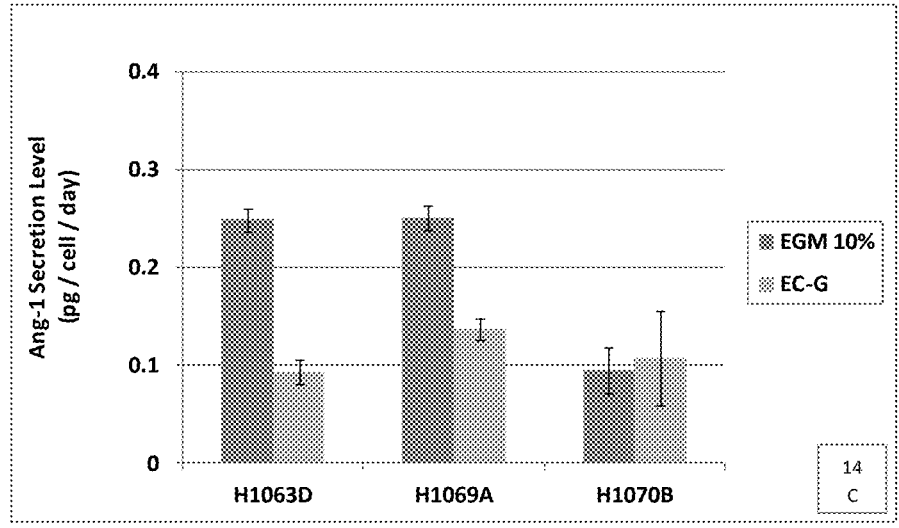
Figure 14D:
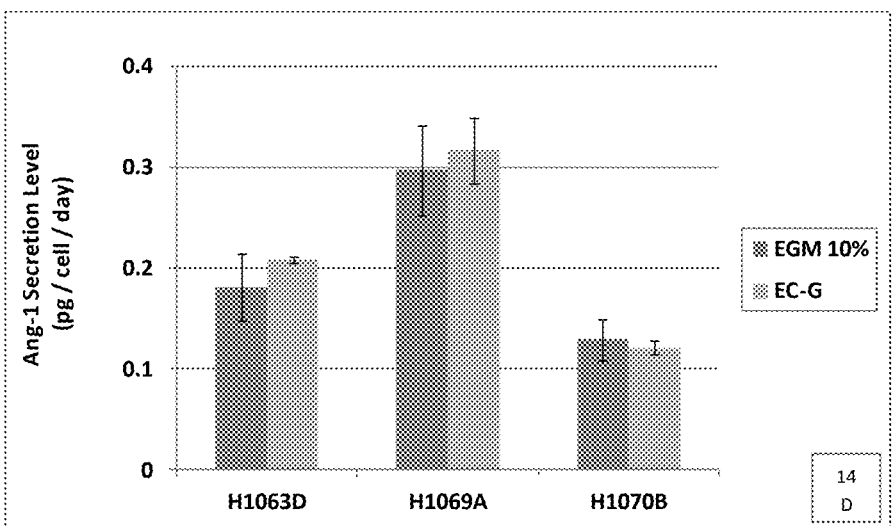

Measurement of secretion of Ang-1 from the transduced EC cells (ELISA) (FIGS. 14C and 14D) also revealed differences between cells grown in different media. FIGS. 14C and 14D show that EC-G-treated cells are much more dependent upon G418 selection than EGM-treated cells. In fact, EGM-treated cells showed little or no difference in Ang-1 secretion before (FIG. 14C) and after (FIG. 14D) 10 days G418 selection.

Example 2: Effect of DEAE-Dextran Concentration on Recovery Rate of SMC Following Transduction Cell Number & Viability (Table 3)

Reducing the DEAE-dextran concentration prior to transduction resulted in better recovery of the SMC in one of the cell donors. 48 hr after transduction (start of selection) the SMC pre-treated with 0.25 mg/ml of DEAE-dextran (1 min exposure), were less impaired than cells pre-treated with 1 mg/ml of DEAE-dextran. As can be seen in Table 3, on the first split (partial depletion) after transduction (S.O.S.) the number of cells in wells comprising cells pre-treated with 0.25 mg/ml of DEAE-dextran for 1 min was significantly higher when compared to cell number in the wells of cells pre-treated with 1 mg/ml of DEAE-dextran for the same time (see Donor A, wells no. 3 and 4 compared to wells nos. 1, 2, 5 and 6). Although this effect was not reflected in cells from Donor B following pre-transduction incubation with the different concentrations of DEAE-dextran (see Table 3), enhanced proliferation has been observed following transduction of cells preconditioned with 0.25 mg/ml DEAE Dextran and during the selection (e.g. G418) step in additional, representative transduced smooth muscle cultures.

Changing the volume of transduction medium from 0.7 ml to 1 ml during the 4 hr incubation with the virus had no effect on cell recovery or final cell number of both donors. Smooth muscle cell response to the increase in volume, however, was reflected in an increase in cell proliferation upon exposure to the selection agent (G418), during the first split (start of selection—see Table 3, Donor A, wells 3 and 4). The viability of the transduced SMC was >95% in all treatments and in all time points that were tested following the transduction procedure.

TABLE 3

| Cell number and viability of human SMC under selection | | | | | | | |
|---|---|---|---|---|---|---|---|

| | Cell split after transduction: | | $1^{st}$ (S.O.S) | | $2^{nd}$ | | $3^{rd}$ |
|---|---|---|---|---|---|---|---|

| DONOR A | | | | | | | |
|---|---|---|---|---|---|---|---|
| Well No. | DEAE-dextran | TM (ml) | Cell No. $(\times 10)^5$ | Viability | Cell # $(\times 10)^5$ | Viability | Cell # $(\times 10)^5$ |
| 1 | 1 mg/ml; 1 min | 0.7 | 2.6 | 98 | 1.15 | 96 | 2.5 |
| 2 | 1 mg/ml; 1 min | 1 | 2.5 | 99 | 1.75 | 96 | 1.9 |
| 3 | 0.25 mg/ml; 1 min | 0.7 | 3.21 | 96 | 2.11 | 98 | 2.5 |
| 4 | 0.25 mg/ml; 1 min | 1 | 4.05 | 99 | 1.72 | 97 | 2.5 |
| 5 | 0.25 mg/ml; 5 min | 0.7 | 2.73 | 98 | 2.19 | 100 | 2.9 |
| 6 | 0.25 mg/ml; 5 min | 1 | 2.7 | 99 | 1.77 | 97 | 2.5 |

| Donor B: | | | | | | | |
|---|---|---|---|---|---|---|---|
| Well No. | DEAE-dextran | TM (ml) | Cell No. $(\times 10)^5$ | Viability | Cell No. $(\times 10)^5$ | Viability | Cell No. $(\times 10)^5$ | Viability |
| 1 | 1 mg/ml; 1 min | 0.7 | 1.97 | 97 | 1.9 | 97 | 4.06 | 96 |
| 2 | 1 mg/ml; 1 min | 1 | 1.78 | 100 | 1.8 | 97 | 3.08 | 99 |
| 3 | 0.25 mg/ml; 1 min | 0.7 | 1.85 | 99 | 1.88 | 100 | 4.0 | 95 |
| 4 | 0.25 mg/ml; 1 min | 1 | 1.89 | 98 | 1.9 | 100 | 4.44 | 97 |
| 5 | 0.25 mg/ml; 5 min | 0.7 | 1.71 | 99 | 1.71 | 96 | 3.94 | 98 |
| 6 | 0.25 mg/ml; 5 min | 1 | 1.81 | 99 | 2.0 | 96 | 3.74 | 98 |

**S.O.S.—start of selection(G418)

Transduction Efficacy (See TABLE 4)

Changing the DEAE-dextran concentration or the volume of transduction medium did not impair the VEGF transduction rate in the two donors:

1. The percent of VEGF-expressing SMC at the beginning of selection was similar for all the transduction conditions.
2. At the end of selection both VEGF expression [IHC (>60%)] and secretion [ELISA (>0.05 pg/cell/day)] were found to be above the acceptance criteria.

TABLE 4

| Summary of IHC of human smooth muscle cells transduced with viral vectors encoding VEGF | | | | |
|---|---|---|---|---|

| Donor A: | | | | |
|---|---|---|---|---|
| Well | | TM | VEGF IHC results (%) | |
| No. | DEAE-dextran | (ml) | S.O.S | EDS |
| 1 | 1 mg/ml; 1 min | 0.7 | 31% | 79% |
| 2 | 1 mg/ml; 1 min | 1 | 39% | 77% |
| 3 | 0.25 mg/ml; 1 min | 0.7 | 32% | 82% |
| 4 | 0.25 mg/ml; 1 min | 1 | 35% | 70% |
| 5 | 0.25 mg/ml; 5 min | 0.7 | NA | 74% |
| 6 | 0.25 mg/ml; 5 min | 1 | 38% | 71% |

| Donor B: | | | | |
|---|---|---|---|---|
| Well | | TM | VEGF IHC results (%) | | ELISA VEGF (pg/cell/day) |
| No. | DEAE-dextran | (ml) | S.O.S | E.O.S | E.O.S |
| 1 | 1 mg/ml; 1 min | 0.7 | 86% | 93% | 0.12 |
| 2 | 1 mg/ml; 1 min | 1 | 86% | 94% | 0.12 |
| 3 | 0.25 mg/ml; 1 min | 0.7 | 88% | 89% | 0.11 |
| 4 | 0.25 mg/ml; 1 min | 1 | 92% | 93% | 0.15 |
| 5 | 0.25 mg/ml; 5 min | 0.7 | 83% | 93% | 0.13 |
| 6 | 0.25 mg/ml; 5 min | 1 | 80% | 93% | 0.14 |

**S.O.S = Start of selection; E.O.S = End of selection
**TM = Transduction medium Potency Assay for DEAE Dextran Pre-Treatment In order to further determine the effect of altering DEAE Dextran pre-treatment parameters on the outcome of viral transduction of SMC cells, experimental transduction with a TGA-LacZ retroviral vector in place of the VEGF retrovirus was performed.

While transducing cells with VEGF requires a one-week selection process followed by immunohistochemical assay, the Lac operon system allows transduction rate to be determined within 3-4 days from transduction using a simple enzymatic procedure followed by count of LacZ-positive cells.

Methods:

Cells from two human donors were seeded in duplicates onto 6-well plates (130,000 cells/well). Prior to transduction, cells were incubated for 1 minute in 1 ml transduction medium (M199 base medium supplemented with 2 mM Glutamine, serum-free) containing either 0.25 mg/ml or 0.125 mg/ml DEAE Dextran (DD).

Two days after transduction cells were harvested and counted by Coulter counter. $0.6\text{-}1 \times 10^4$ cells of each well were then re-seeded onto 12-well plates for proliferation assay using standard protocol. In brief, $0.6\text{-}1 \times 10^4$ cells were incubated in SMCG media and seeded in 12-well plates. 5 days later, cells were harvested and counted by Coulter counter.

$2 \times 10^5$ cells of each well were re-seeded onto 6-well plates, fixed and stained for LacZ using a standard X-Gal protocol. 10-15 representative fields of the culture plates were photographed and cells were counted.

Growth rate of SMC was determined according to the formula below:

$$\frac{Log_2[(\text{number of cells harvested})/(\text{number of cells seeded})]}{(\text{number of days in culture})}$$

Results:

Cell Condition:

Cells were photographed during transduction and 2.5 hours after medium was changed to regular growth medium. FIG. 15A shows that all cells treated with DEAE Dextran and transduced with TGA retrovirus suffered during the transduction process. However, while cells treated with 0.25 mg/ml DD showed clear morphological signs of stress (FIG. 15B), cells treated with 0.125 mg/ml DD appear more robust and healthy (FIG. 15C).

Cell Proliferation:

FIGS. 16 and 17 show the effects of DD concentration on proliferation rate of TGA retrovirus-transduced SMC 2 or 5 days after transduction, respectively. No significant advantage is discernible in proliferation of SMCs pre-treated with 0.25 mg/ml DD compared with that of SMCs pre-treated with 0.25 mg/ml DD at both 2 and 5 days post-transduction.

Transduction Efficiency

Two days after transduction, transduced SMC were fixed and stained for LacZ. FIG. 18 shows a representative photograph of stained cells (LacZ-positive cells are stained blue). Quantification of Lac-Z positive cells (Lac-Z positive as percent of total cells observed, FIG. 19) clearly shows that pretreatment of the SMC with 0.125 mg/ml DD resulted in TGA-LacZ transduction efficiency similar to that of pre-treatment with 0.25 mg/ml DD.

Conclusions:

Taken together, the above results indicate that vascular cells (endothelial cells and smooth muscle cells) isolated in EGM 10% (EC cells) or SMGM 20% (SMC cells), and then grown in EGM 10% (EC cells) or SMGM 15% (SMC cells), and preconditioned with DEAE-Dextran are endowed with increased transduction rate and/or enhanced proliferation in culture following transduction angiogenic factors, compared to that of similar vascular cells isolated and/or cultured without EGM or SMGM medium. Further, smooth muscle cells pre-conditioned with DEAE-dextran at a concentration of 0.25 mg/ml, or even lower, 0.125 mg/ml exhibit increased transduction rate and/or enhanced proliferation in culture following transduction with angiogenic factors, compared to that of similar smooth muscle cells pre-conditioned with 1.0 mM or greater DEAE-Dextran.

Example 3: Efficient Smooth Muscle and Endothelial Cell Transduction Protocol Reduction in the length and number of ex-vivo manipulations of cells intended for readministration to patients can be critical to the success of cellular therapy methods. Reduction of ex-vivo retroviral transduction time for endothelial and smooth muscle cells, as well as improvements in the transduction medium were examined.

Methods:

Cells: Endothelial cells (EC) from two human donors (H1065A and H1066), and smooth muscle cells (SMC) from two human donors (H1058A and H1057C) prepared and cryopreserved were thawed at passage 2, grown to confluence, harvested and seeded for transduction in 6-well tissue culture plates.

Transduction: The following day, EC cells were transduced with an Angiopoietin-1 (Ang-1) retroviral vector for either 3.5 or 4 hours, or 2.5 hours, in duplicates. SMC cells were transduced with the $VEGF_{165}$ vector for 3.5 or 2.5 hours. Following transduction, the medium was changed to growth medium and the cells were incubated for 3 days at 37° C., 5% $CO_2$.

Assay: Two days after transduction, cells were harvested and counted. Slides were seeded in order to assess the Ang-1 (AC) or VEGF (SMC) transduction rate by immunohistochemistry (IHC), and by ELISA assay for the presence of the angiogenic factor in supernatants (secreted) or cell lysates.

Growth: The cells were re-seeded to tissue culture dishes and grown in the presence of 0.5 mg/ml G418 for 10 days.

Assessment: After the 10-days selection period, cells were harvested and counted. Results were reported from the immunohistochemistry slides and ELISA tests. Proliferation rate (divisions per day) was calculated according to the following formulas:

For step 3 (Transduction plus 2 days): $Log_2$ (cell number at step $3/1.3 \times 10^5$ (number of cells seeded for transduction))/3 (number of days from transduction).

For step 3b (Transduction plus 13 days, including 10 days in G418 selection medium): $Log_2$ (cell number at step 3b/number of cells seeded)/3 or 6 (number of days from last harvest).

SMC Transduction Medium:

In some experiments, the effect of DEAE-dextran concentration on SMC transduction was investigated. Smooth muscle cells (SMC) from two human donors were prepared for transduction ($1.3 \times 10^5$ cells/well of 6-well plate) as described hereinabove. On the following day the cells intended for transduction were transferred to transduction medium (M199 medium supplemented with 2 mM Glutamine, at 37° C., 5% $CO_2$) and pre-exposed to DEAE-dextran at either 1 mg/ml for 1 min, or 0.25 mg/ml for 1 or 5 min. The cells were then washed 3 times with PBS and incubated with the retroviral vector suspended in either 0.7 ml/well or iml/well of transduction medium for 4 hours at 37° C., 5% $CO_2$. The amount and volume of retroviral vector to be used was calculated according to the cell number and multiplicity of infection (MOI) of 8. From 48 hr after transduction the cells were maintained with G418 (0.35 mg/ml) selection for ten days. Each 2-3 days the cells were harvested and counted using a hemacytometer and their viability was determined. After each cell split (semi-depletion), $1.0-1.3 \times 10^5$ cells from each treatment were seeded in wells of 6-well tissue culture plate. To evaluate VEGF transgene expression Immunohistochemistry (IHC) assay was performed at the beginning and in the end of the G418 selection period. Evaluation of VEGF levels in the supernatants was performed with ELISA for the samples of Donor B.

Results:

Proliferation rate—Cell growth/proliferation rates (Growth/proliferation rate=divisions/day) of cells transduced with the Ang-1 or VEGF vector for 2.5 hours were similar to those of cells transduced with the vectors for 3.5 or 4 hours, regardless of when the proliferation rate was assayed (FIGS. 20A and 20B: Step 3=transduction+2 days; Step 3b=transduction+13 days, including 10 days of G418 selection).

Transduction rate-Transduction rate of endothelial cells with the Ang-1 retroviral vector, or smooth muscle cells with the VEGF vector was assessed by immunohistochemistry for intracellular protein levels and by ELISA for secreted protein levels. Transduction rate (Percent transduced cells from total) for EC cells transduced with the Ang-1 vector for 2.5 hours was similar to, and even higher than that of cells transduced with the vector for 4 or 3.5 hours, regardless of when the transduction rate was assayed (Tables 5, 6, 7 and 8, +2 days—Step 3 or +3 or +6 days-Step 3b).

Transduction rate for SMC cells transduced with the VEGF vector for 2.5 hours was similar to, if not higher than that of cells transduced with the same vector for 3.5 hours, regardless of when the assay was performed or type of assay.

Ang-1 Transduction rate results are summarized in Tables 5 (subject H1065A) and

TABLE 5

| Transduction rate in H1065A: | | | |
| --- | --- | --- | --- |
| Transduction | Step 3 | Step 3b | |
| time (hours) | IHC | IHC | ELISA |
| 2.5 | 69% | 69% | 0.433 |
| 4 | 68% | 69% | 0.337 |

TABLE 6

| Transduction rate in H1057C: | | | |
| --- | --- | --- | --- |
| Transduction | Step 3 | Step 3b | |
| time (hours) | IHC | IHC | ELISA |
| 2.5 | 63% | 68% | 0.249 |
| 3.5 | 62% | 64% | 0.189 |

Note:
* IHC results are presented as % of Ang-1-positive stained cells.
** ELISA results are presented in pg Ang secreted/cell/day.
*** Each value in the table represents an average of two duplicates.

VEGF Transduction rate results are summarized in Tables 7 (subject H1058A) and 8 (subject H1057C) below:

TABLE 7

| SMC Transduction rate in H1058A: | | | |
| --- | --- | --- | --- |
| Transduction | Step 3 | Step 3b | |
| time (hours) | IHC | IHC | ELISA |
| 2.5 | 79% | 80% | 0.157 |
| 3.5 | 68% | 82% | 0.163 |

TABLE 8

| SMC Transduction rate in H1057C: | | | |
| --- | --- | --- | --- |
| Transduction | Step 3 | Step 3b | |
| time (hours) | IHC | IHC | ELISA |
| 2.5 | 73% | 88% | 0.226 |
| 3.5 | 70% | 85% | 0.113 |

Note:
* IHC results are presented as % of VEGF-positive stained cells.
** ELISA results are presented in pg VEGF secreted/cell/day.
*** Each value in the table represents an average of two duplicates.

Example 4: Hypothermic Preservation of Transduced Isolated Vascular Cells

Materials and Methods

Primary Culture of Human Endothelial and Smooth Muscle Cells

Endothelial (EC) and Smooth Muscle cells (SMC) were isolated from human-derived vein segments stripped from the patient and transferred to the cell processing unit. Cells were isolated from the vein in two steps of enzymatic reaction: EC are isolated first, and the remainder of the vein is used to isolate SMC.

EC and SMC isolation from different human donors was performed no more than 48 hours after vein stripping. Briefly, EC were isolated by enzymatic digestion and aggressive washing, while SMC were isolated by enzymatic digestion and seeding of the tissue explants.

EC cell cultures were seeded onto fibronectin-coated 6-well tissue plates and cultured in growth medium until formation of large colonies covering % to % of the plate surface ("monolayers") and harvested by trypsinization.

SMC cell cultures for SMC isolation were initiated in growth medium under standard conditions until sprouting of smooth muscle cells from the explants into colonies covering ¼ to ½ of the plate surface and harvested by trypsinization.

Following harvesting the isolated EC and the SMC cells were reseeded onto gelatin-coated 6-well tissue culture vessels or 25 cm$^3$ flasks.

Viral Transduction

Endothelial and smooth muscle cells are transduced separately using retroviral vectors. Endothelial cells are transduced by a retroviral vector encoding Ang-1 and smooth muscle cells are transduced by a retroviral vector encoding VEGF$_{165}$.

Vascular cells intended for transduction were transferred to transduction medium (M199 medium supplemented with 2 mM Glutamine, at 37° C., 5% CO$_2$) and pre-exposed to DEAE-dextran. The cells were then washed 3 times with PBS and incubated with the retroviral vector suspended in up to 1 ml/well of transduction medium for up to 4 hours at 37° C., 5% CO$_2$. The amount and volume of retroviral vector to be used was calculated according to the cell number and multiplicity of infection (MOI) of 8. From 48 hr after transduction the cells were maintained with G418 (0.35 mg/ml) selection for ten days. Each 2-3 days the cells were harvested and counted using a hemacytometer and their viability, cell proliferation rate and/or transduction rate assessed.

Transduced Vascular Cell Formulation & Release

EC cells and SMC cells were processed similarly and separately from one another. A sufficient amount of each cell type is harvested, washed (three times) in order to eliminate residual culture medium reagents, the cells of each type are counted in a Coulter counter and re-suspended in 10 ml of hypothermic preservation solution (see more details below). In preparation for injection, the final transduced vascular cell composition is formulated in two separate 20 ml latex-free polypropylene syringes sealed with syringe injection caps. The syringes are stored in a sterile re-closable polybag at 4-8° C. immediately after composition formulation until injection, up to 48 hours after in the present experiments.

Hypothermic Preservation Solutions

Isotonic bicarbonate-buffered solution [Plasma-lyte A® (Baxter, USA), 1% Human Albumin solution (ZE-NALB 20, BPL, UK), 0.1% dextrose, 100 U/ml heparin. pH is adjusted to 7.4-7.7 with 8.4% sodium bicarbonate]. All solutions are sterile, and approved for I.V injection (PlasmaLyte)(PL).

Intracellular-HEPES-buffered [HypoThermosol®-FRS (BioLife, cat #80093-710) (HTS)].

Assay Preparation

In order to evaluate the viability of the cells suspended in the hypothermic preservation solutions, endothelial and smooth muscle cells from three human donors were tested. The cells were harvested and divided into two tubes, each for one of the hypothermic preservation solutions. The cells were washed three times with the hypothermic preservation solution. After the final wash, the cells were counted by Coulter counter and assessed for viability using trypan blue and a counting chamber. Cells were diluted in hypothermic preservation solution to 0.5-1×10⁶ cells/ml, in duplicates. The cells were kept at 4-6° C. Cell counts and viability tests were performed after 24 and 48 hours. After the final count (at 48 h), the cells were seeded onto 25 cm² flasks or 6-well plates, depending on the number of cells remaining.

Viability Assay

Cell culture viability after incubation in hypothermic preservation solution was tested using two parameters—The number of whole cells in the suspension and viability of surviving cells. The number of whole cells in each sample was assessed by Coulter counter at each time point. The viability of whole cells was assessed by sampling the cell suspension 1:1 with 0.04% Trypan blue reagent (Sigma). Live and dead cells were counted using a counting chamber under inverted light microscope. Cell viability is expressed as the ratio of live (Trypan blue-excluding cells) and total cell number. Viability was determined at 0, 24 and 48 hours following cells incubation in hypothermic preservation solution at 4° C., starting from final product formulation (time 0).

Cell Condition and Proliferation Post Incubation in Injection Solution

Cells incubated for 24 and 48 hours in the cold injection solutions were plated (Cells were seeded onto either 6-well plates or 25 cm² flasks in the same number based on the lowest number of cells) in their growth media. Twenty-four and 72 hours post seeding, the cells were photographed and their status was evaluated. Seventy-two hours post seeding the cells were harvested and counted by a Coulter counter (Beckman Z series).

Gene Expression and Cell Identity Post Incubation in Hypothermic Preservation Solution After counting cells were seeded for gene expression by ELISA and immunohistochemistry (IHC) assays, and for cells' identity assay by FACS. IHC allows visualization of individual gene-expressing cells (Ang-1 or VEGF) using specific antibodies for either Ang-1 or VEGF. ELISA allows a quantitative measurement of transgene expression levels. Ang-1 levels were measured using an R&D® Angiopoietin-1 ELISA Kit (R&D Systems, Quantikine Human Angiopoietin-1 Immunoassay, cat: DANG10) and VEGF$_{165}$ protein levels were determined using a VEGF ELISA kit (R&D Systems, Quantikine Human VEGF Immunoassay, cat: DVE00), according to the manufacturer's instructions. The identity of EC was determined by the specific cell surface marker CD31 using flow cytometry assay, and the identity of SMC was determined by the specific cell surface marker α-smooth muscle actin (α-SMA), also using flow cytometry.

Results

Effect of Hypothermic Preservation Solution Type on Number and Viability of EC and SMC:

Comparison of cell number in samples of vascular cells stored in isotonic bicarbonate-buffered hypothermic preservation solution (PL) and intracellular-HEPES-buffered hypothermic preservation solution (HTS) revealed little change in EC (FIG. 21A) or SMC (FIG. 21B) cell number after 24 hours incubation. However, after 48 hours, a small but significant decrease in cell number of EC cells in the HTS samples was discerned, while cell numbers of the EC cells in the PL samples remained unchanged.

In contrast, FIG. 21B shows that while no significant change was discerned in the number of SMC cells in suspension after 24 hours, after a 48 hour incubation in PL (FIG. 21B), there is a small but significant decrease in SMC cell number, while cell numbers of SMC incubated with HTS remained unchanged.

Cell viability (assessed by Trypan-blue exclusion) following incubation in isotonic bicarbonate-buffered hypothermic preservation solution (PL) and intracellular-HEPES-buffered hypothermic preservation solution (HTS) reflected similar trends.

In EC cells, viability was significantly decreased after 24 hour incubation in HTS and remained substantially unchanged in PL (FIG. 22A). EC cell viability after 48 hour incubation in hypothermic preservation solutions decreased in both HTS and PL, but significantly more in HTS (Average of 80% viability vs. 88% in PL). The viability of all EC tested (3 donors) was no less than 83% after a 48 hour incubation in the PL solution.

FIG. 22B shows that both solutions can effectively maintain SMC viability over a 24 hour incubation period. After 48 hours incubation, there is a significant decrease in cell viability of SMC cells incubated in the PL hypothermic preservation solution, while the viability of SMC incubated in HTS hypothermic preservation solution remained unchanged (FIG. 22B). The viability of all stored SMC cells samples (3 donors) was no less than 89% after a 48 hour incubation in the HTS hypothermic preservation solution.

Effect of Hypothermic Preservation Solution Type on Cell Condition in Culture

Attachment of seeded vascular cells to the culture plate substrate is an indication of functional integrity of the isolated cells, and a good predictor of robustness of the isolated cells. Monitoring in-situ in the culture also provides an indication of the proliferation rate in culture.

Observation of the vascular cells following incubation for 24 or 48 hours in either isotonic bicarbonate-buffered hypothermic preservation solution (PL) or an intracellular-HEPES-buffered hypothermic preservation solution (HST) revealed that EC cells treated and incubated for 24 (FIG. 23A) and 48 hours (FIG. 24A) in the PL hypothermic preservation solution, adhere better to the plate surface, have a higher cell concentration and superior proliferation capabilities than EC cells incubated in the HTS hypothermic preservation solution (FIG. 23B and FIG. 24B) for a similar duration.

On the other hand, SMC cells incubated for 24 hours (FIG. 23D) or 48 hours (FIG. 24D) with intracellular-HEPES-buffered hypothermic preservation solution (HST), adhere better to the plate surface, have a higher concentration and display better proliferation capabilities than SMC cells incubated for 24 hours (FIG. 23C) or 48 hours (FIG. 24C) with PL hypothermic preservation solution.

Effect of Hypothermic Preservation Solution Type on Cell Proliferation Rate:

Cell proliferation rates (divisions/day), 72 hours post seeding of EC cells and SMC cells, following 24 or 48 hours incubation in hypothermic preservation solutions, are detailed in FIGS. 25A (EC cells), 25B (SMC cells) and Table 9 below.

Compare to the proliferation rate of EC cells incubated with HTS solution, a significant increase in EC cell proliferation rate (divisions/day) was detected in EC cells incubated 24 and 48 hour incubation in the hypothermic preservation solution (FIG. 25A).

In SMC, a significant increase was detected in the SMC cells' capability to proliferate with both 24 and 48 hours incubation in the HTS solution (FIG. 25A).

TABLE 9

| | | | | | | | | |
|---|---|---|---|---|---|---|---|---|
| EC and SMC growth rate 72 hours post seeding, after a 24 and 48 hour incubation in hypothermic preservation solutions. Results are shown as average of two repeats of each experimental condition. | | | | | | | | |
| EC growth rate (Divisions/Day) | | | | SMC growth rate (Divisions/Day) | | | | |
| EC Donor | Hypothermic preseravation solution type | Following 24 h incubation | Following 48 h incubation | SMC Donor | Hypothermic preservation solution type | Following 24 h incubation | Following 48 h incubation |
| 204-006-YM | PL | 0.18 | 0.16 | 206-001-MAN | PL | 0.34 | −0.09 |
| | HTS | 0.14 | 0.02 | | HTS | 0.46 | 0.43 |
| 204-004-DI | PL | 0.32 | 0.17 | 205-001-NR | PL | 0.28 | −0.01 |
| | HTS | 0.21 | 0.00 | | HTS | 0.37 | 0.31 |
| 204-003-DH | PL | 0.54 | 0.52 | 204-001-AE | PL | 0.28 | −0.01 |
| | HTS | 0.49 | 0.04 | | HTS | 0.35 | 0.23 |

Gene Expression and Cell Identity Post Incubation in Hypothermic Preservation Solution:

Transgene expression levels post incubation in the tested solutions were evaluated by IHC and ELISA, using specific antibodies.

As presented in tables 10 (24 hours incubation) and 11 (48 hours incubation) below, both endothelial and smooth muscle transduced vascular cells had similar transgene expression levels (tested by IHC) post-incubation in both hypothermic preservation solutions. Incubation of the SMC cells in PL hypothermic preservation solution resulted in more abundant transgene protein (VEGF) secretion than that of SMC cells incubated in the HTS hypothermic preservation solution. However, the secretion levels for all tested conditions were above predetermined acceptance criteria (>0.05 pg/cell/day). In EC, transgene protein secretion level was similar for cells incubated in both PL and HTS hypothermic preservation solutions.

Post-incubation flow cytometry results of culture purity and cell characterization for all samples of both EC and SMC in the tested solutions, were above predetermined acceptance criteria (>85% CD31-positive cells for EC; >60% α-SMA-positive cells for SMC).

TABLE 10

| | | | | | | | |
|---|---|---|---|---|---|---|---|
| EC and SMC transgene expression after 24 hours incubation in hypothermic preservation solutions. Results are shown as average of two repeats of each experimental condition. | | | | | | | |
| Ang-1 Expression by Endothelial Cells | | | | VEGF Expression by Smooth Muscle Cells | | | |
| EC Donor | Hypothermic preservation solution type | IHC (%) | ELISA (pg/cell/day) | SMC Donor | Hypothermic preservation solution type | IHC (%) | ELISA (pg/cell/day) |
| 204-006-YM | PL | 46% | 0.207 | 206-001-MAN | PL | 90% | 0.206 |
| | HTS | 33% | 0.206 | | HTS | 86% | 0.150 |
| 204-004-DI | PL | 69% | 0.327 | 205-001-NR | PL | 97% | 0.356 |
| | HTS | 63% | 0.333 | | HTS | 97% | 0.235 |
| 204-003-DH | PL | 56% | 0.183 | 204-001-AE | PL | 95% | 0.247 |
| | HTS | 61% | 0.168 | | HTS | 95% | 0.192 |

TABLE 11

| | | | | | | | |
|---|---|---|---|---|---|---|---|
| EC and SMC transgene expression after a 48 h incubation in injection solutions. Results are shown as average of two repeats of each experimental condition. | | | | | | | |
| Ang-1 Expression by Endothelial Cells | | | | VEGF Expression by Smooth Muscle Cells | | | |
| EC Donor | Hypothermic preservation solution type | IHC (%) | ELISA (pg/cell/day) | SMC Donor | Hypothermic preservation solution type | IHC (%) | ELISA (pg/cell/day) |
| 204-006-YM | PL | 64% | 0.218 | 206-001-MAN | PL | 90% | 0.225 |
| | HTS | 62% | 0.166 | | HTS | 86% | 0.185 |
| 204-004-DI | PL | 76% | 0.315 | 205-001-NR | PL | 95% | 0.396 |
| | HTS | 60% | 0.270 | | HTS | 94% | 0.280 |
| 204-003-DH | PL | 63% | 0.215 | 204-001-AE | PL | 92% | 0.243 |
| | HTS | 59% | 0.222 | | HTS | 89% | 0.205 |

Taken together, these data strongly indicate that specific formulation is effective in obtaining improved hypothermic preservation of the different vascular cell types, supporting the use of custom hypothermic preservation solution formulations for transplantable transduced vascular cells for cell therapy.

The data presented herein illustrates that preserving human SMC over 48 hours at 4° C. is best achieved using intracellular-HEPES-buffered hypothermic preservation solution (HST). In comparison, isotonic bicarbonate-buffered hypothermic preservation solution (PL) (supplemented with 1% Human Albumin solution, 0.1% dextrose, 100 U/ml heparin, pH adjusted to 7.4-7.7 with 8.4% sodium bicarbonate) was best for preserving human EC cells over 48 hours at 4° C.

Without ascribing to a single hypothesis, one possible interpretation of the varying levels of cell protection uncovered by each of the hypothermic preservation solutions is that the cellular response and death cascades launched during and subsequent to preservation in vascular SMC cells may be different from that of vascular EC cells.

FIG. 26 shows:
Retroviral Vector Map
Molecule Definition:
    Molecule: LXSN_Ang1, 7389 bps DNA Circular
    Description: Ligation of Ang_BglII into cut bamHI
Molecule Features:

| Type | Start | End | Name |
|---|---|---|---|
| REGION | 1 | 588 | 5'LTR |
| GENE | 1480 | 2995 | Ang-1 |
| REGION | 2995 | 3360 | Psv40 |
| GENE | 3406 | 4200 | Neo |
| REGION | 4260 | 4853 | 3'LTR |
| GENE | 6998 | 6155 | C Amp |

Molecule Definition:
    Molecule: LXSN_Ang1, 7389 bps DNA Circular
    File Name: LXSN_Ang1.cm5, dated 28 Feb. 2005
    Description: Ligation of Ang_BglII into cut bamHI
Molecule Features:

| Type | Start | End | Name |
|---|---|---|---|
| REGION | 1 | 588 | 5'LTR |
| GENE | 1480 | 2995 | Ang-1 |
| REGION | 2995 | 3360 | Psv40 |
| GENE | 3406 | 4200 | Neo |

-continued

| Type | Start | End | Name |
|---|---|---|---|
| REGION | 4260 | 4853 | 3'LTR |
| GENE | 6998 | 6155 | C Amp |

SEQ ID NO: 1: VEGF 165 nucleic acid construct LXSN_VEGF165 map
Molecule Definition:
    Molecule: product1, 6473 bps DNA Circular
    File Name: LXSN_VEGF165
    Description: Ligation of Fragment 2 into cut BamHI
Molecule Features:

| Type | Start | End | Name |
|---|---|---|---|
| REGION | 1 | 588 | 5'LTR |
| GENE | 1480 | 2079 | VEGF |
| REGION | 2079 | 2444 | Psv40 |
| GENE | 2490 | 3284 | Neo |
| REGION | 3344 | 3937 | 3'LTR |
| GENE | 6082 | 5239 | C Amp |

Molecule Definition:
    Molecule: product1, 6473 bps DNA Circular
    File Name: LXSN_VEGF165_2.cm5, dated 24 Feb. 2005
    Description: Ligation of Fragment 2 into cut BamHI
Molecule Features:

| Type | Start | End | Name |
|---|---|---|---|
| REGION | 1 | 588 | 5'LTR |
| GENE | 1480 | 2079 | VEGF |
| REGION | 2079 | 2444 | Psv40 |
| GENE | 2490 | 3284 | Neo |
| REGION | 3344 | 3937 | 3'LTR |
| GENE | 6082 | 5239 | C Amp |

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for transducing human smooth muscle (SM) cells comprising:

(a) preconditioning said human smooth muscle cells with between 0.125 mg/ml and 0.5 mg/ml DEAE-Dextran for 1-4 minutes, so as to obtain preconditioned human smooth muscle cells, (b) washing said preconditioned SM cells so as to remove said DEAE-Dextran, and (c) contacting the preconditioned human smooth muscle cells with a viral vector comprising a retroviral nucleic acid construct or a lentivirus nucleic acid construct in a DEAE-Dextran-free transduction medium comprising the viral vector comprising the retroviral or lentiviral nucleic acid construct, wherein the construct comprises a polynucleotide sequence encoding a VEGF$_{165}$ polypeptide, wherein said transduction medium comprises M199 medium, and wherein following step (c) said SM cells are characterized by at least one of increased transduction rate and increased proliferation following transduction, as compared to similar SM cells preconditioned with 1.0 mg/ml DEAE-Dextran or greater.

2. The method of claim 1, wherein said preconditioning is performed with 0.25 mg/ml DEAE-Dextran.

3. The method of claim 1, wherein said preconditioning is performed with 0.125 mg/ml DEAE-Dextran and for 1 minute.

4. The method of claim 1, wherein said transduction medium further comprises 2 mM Glutamine.

5. The method of claim 1, wherein said transduction medium is a serum-free medium.

6. The method of claim 1, wherein said human smooth muscle cells are selected from the group consisting of freshly isolated smooth muscle cells from venous tissue, cryopreserved and thawed smooth muscle cells from venous tissue and cultured human smooth muscle cells.

7. The method of claim 1, wherein said human smooth muscle cells are cultured in medium comprising Smooth muscle basal medium (SmBM), Fetal Bovine Serum, Insulin, Human Epidermal Growth Factor (hEGF), Human Fibroblast Growth Factor-B (hFGF-B) and Gentamicin plus Amphotericin B prior to and following said transduction.

8. The method of claim 7, wherein said culture medium further comprises 5-25% fetal bovine serum (FBS).

9. The method of claim 7, wherein said culture medium further comprises 10-20% fetal bovine serum (FBS).

10. The method of claim 7, wherein said culture medium further comprises 15% fetal bovine serum (FBS).

11. The method of claim 1, wherein said human smooth muscle cells are smooth muscle cells isolated from venous tissue in isolation medium comprising Smooth muscle basal medium (SmBM), Fetal Bovine Serum, Insulin, Human Epidermal Growth Factor (hEGF), Human Fibroblast Growth Factor-B (hFGF-B) and Gentamicin plus Amphotericin B.

12. The method of claim 11, wherein said isolation medium comprises 20% fetal bovine serum.

13. A method for transducing human smooth muscle (SM) cells comprising:

(a) preconditioning said human smooth muscle cells with between 0.125 mg/ml and 0.5 mg/ml DEAE-Dextran for 1-4 minutes, so as to obtain preconditioned human smooth muscle cells, (b) washing said preconditioned SM cells so as to remove said DEAE-Dextran, and (c) contacting the preconditioned human smooth muscle cells with a viral vector comprising a retroviral nucleic acid construct or a lentivirus nucleic acid construct in a DEAE-Dextran-free transduction medium comprising the viral vector comprising the retroviral or lentiviral nucleic acid construct, wherein said transduction medium comprises M199 medium, and wherein the construct comprises a polynucleotide sequence encoding a VEGF$_{165}$ polypeptide, wherein said polynucleotide sequence is as set forth in SEQ ID NO: 1, and wherein following step (c) said SM cells are characterized by at least one of increased transduction rate and increased proliferation following transduction, as compared to similar SM cells preconditioned with 1.0 mg/ml DEAE-Dextran or greater.

* * * * *